US008609691B2

(12) United States Patent
Plettenburg et al.

(10) Patent No.: US 8,609,691 B2
(45) Date of Patent: Dec. 17, 2013

(54) CYCLOHEXYLAMIN ISOQUINOLONE DERIVATIVES

(75) Inventors: Oliver Plettenburg, Frankfurt (DE); Armin Hofmeister, Frankfurt (DE); Dieter Kadereit, Frankfurt (DE); Joachim Brendel, Bad Vilbel (DE); Matthias Loehn, Frankfurt (DE); Jean-Michel Altenburger, Paris (FR)

(73) Assignee: Sanofi, Paris (FR)

( * ) Notice: Subject to any disclaimer, the term of this patent is extended or adjusted under 35 U.S.C. 154(b) by 1415 days.

(21) Appl. No.: 12/019,799

(22) Filed: Jan. 25, 2008

(65) Prior Publication Data

US 2008/0242699 A1    Oct. 2, 2008

Related U.S. Application Data

(63) Continuation of application No. PCT/EP2006/007140, filed on Jul. 20, 2006.

(30) Foreign Application Priority Data

Jul. 26, 2005 (EP) .................................. 05016153

(51) Int. Cl.
C07D 217/24 (2006.01)
A61K 31/472 (2006.01)

(52) U.S. Cl.
USPC .......................................... 514/309; 546/141

(58) Field of Classification Search
None
See application file for complete search history.

(56) References Cited

U.S. PATENT DOCUMENTS

| 5,480,883 | A | 1/1996 | Spada et al. |
| 6,903,107 | B1 | 6/2005 | Timmers et al. |
| 7,217,722 | B2 | 5/2007 | Takami et al. |
| 7,618,985 | B2 | 11/2009 | Ray et al. |
| 2003/0220368 | A1 | 11/2003 | Ozaki et al. |
| 2004/0138286 | A1 | 7/2004 | Imazaki et al. |
| 2006/0079556 | A1 | 4/2006 | Sher et al. |
| 2007/0060595 | A1 | 3/2007 | Yoshizawa et al. |
| 2008/0045566 | A1 | 2/2008 | Ray et al. |

FOREIGN PATENT DOCUMENTS

| EP | 1403255 | 3/2004 |
| EP | 1541559 | 6/2005 |
| EP | 1550660 | 7/2005 |
| FR | 2485537 | 6/1980 |
| JP | 10087629 | 4/1998 |
| WO | 9202476 | 2/1992 |
| WO | 9706802 | 2/1997 |
| WO | 9723214 | 7/1997 |
| WO | 9806433 | 2/1998 |
| WO | 9911642 | 3/1999 |
| WO | 0024718 | 5/2000 |
| WO | 200703299 | 12/2000 |
| WO | 0139726 | 6/2001 |
| WO | 0153288 | 7/2001 |
| WO | 0156988 | 8/2001 |
| WO | 0164238 | 9/2001 |
| WO | 0164656 | 9/2001 |
| WO | 0177101 | 10/2001 |
| WO | 0192227 | 12/2001 |
| WO | 0234712 | 5/2002 |
| WO | 02055496 | 7/2002 |
| WO | 02076457 | 10/2002 |
| WO | 02088101 | 11/2002 |
| WO | 03018556 | 3/2003 |
| WO | 03024450 | 3/2003 |
| WO | 03053330 | 7/2003 |
| WO | 2004106325 | 12/2004 |
| WO | 2004113297 | 12/2004 |
| WO | 2005035933 | 2/2005 |
| WO | 2005030130 | 4/2005 |
| WO | 2005030791 | 4/2005 |
| WO | 2005035516 | 4/2005 |

(Continued)

OTHER PUBLICATIONS

U.S. Appl. No. 11/961,193, filed Dec. 20, 2007, Plettenburg, et al.

(Continued)

Primary Examiner — Zinna Northington Davis
(74) Attorney, Agent, or Firm — Scully, Scott, Murphy & Presser, P.C.

(57) ABSTRACT

The invention relates to 6-cyclohexylamine-substituted isoquinolone derivatives of the formula (I)

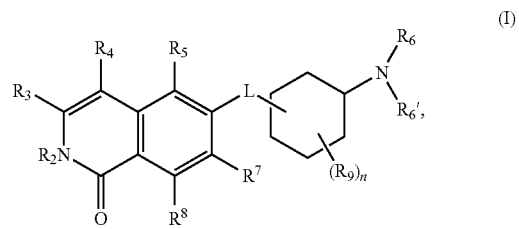

or isoquinoline derivatives of the formula (I')

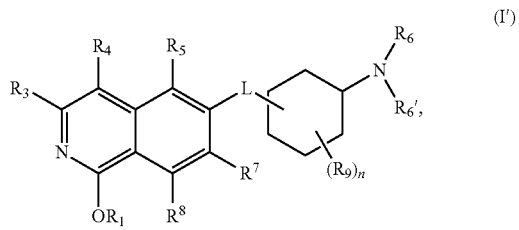

useful for the treatment and/or prevention of diseases associated with Rho-kinase and/or Rho-kinase mediated phosphorylation of myosin light chain phosphatase, and compositions containing such compounds.

54 Claims, No Drawings

(56) References Cited

FOREIGN PATENT DOCUMENTS

| WO | 2005054202 | 6/2005 |
|---|---|---|
| WO | 2005074535 | 8/2005 |
| WO | 2005087226 | 9/2005 |
| WO | 2005095362 | 10/2005 |
| WO | 2007012421 | 2/2007 |
| WO | 2007012422 | 2/2007 |
| WO | 2007039563 | 4/2007 |
| WO | 2007063916 | 6/2007 |
| WO | WO 2007/065916 | 6/2007 |
| WO | 2005020081 | 2/2008 |
| WO | 2008020081 | 2/2008 |
| WO | WO 2008/020081 | 2/2008 |
| WO | 2008077555 | 7/2008 |
| WO | 2008077556 | 7/2008 |

OTHER PUBLICATIONS

U.S. Appl. No. 12/019,866, filed Jan. 25, 2008, Plettenburg, et al.
U.S. Appl. No. 12/487,403, filed Jun. 18, 2009, Plettenburg, et al.
U.S. Appl. No. 12/487,479, filed Jun. 18, 2009, Plettenburg, et al.
U.S. Appl. No. 12/487,455, filed Jun. 18, 2009, Plettenburg, et al.
U.S. Appl. No. 12/487,525, filed Jun. 18, 2009, Plettenburg, et al.
U.S. Appl. No. 12/487,386, filed Jun. 18, 2009, Plettenburg, et al.
U.S. Appl. No. 12/487,409, filed Jun. 18, 2009, Plettenburg, et al.
U.S. Appl. No. 12/487,503, filed Jun. 18, 2009, Plettenburg, et al.
Alvarez, M. et al., "Product Class 5: Isoquinolines," Science of Synthesis (2005), vol. 15, pp. 661-838.
Alvarez, M. et al., "Product Class 6: Isoquinolines," Science of Synthesis (2005), vol. 15, pp. 839-906.
Al, Shingo et al., "Rho-Rho kinase is involved in smooth muscle cell migration through myosin light chain phosphorylation-dependent and independent pathways," Atherosclerosis (2001), vol. 155, pp. 321-327.
Bauer, Markus et al., "Dichotomous Regulation of Myosin Phosphorylation and Shape Change by Rho-Kinase and Calcium in Intact Human Platelets," Blood (1999), vol. 94, pp. 1665-1672.
Chellaiah, Meenakshi et al., "Rho-dependent Rho Kinase Activation Increases CD44 Surface Expression and Bone Resorption in Osteoclasts," The Journal of Biological Chemistry (2003), vol. 278, pp. 29086-29097.
Chitaley, Kanchan et al., "Antagonism of Rho-kinase stimulates rat penile erection via a nitric oxide-independent pathway," Nature Medicine (2001), vol. 7, pp. 119-122.
Maruoka, Shuichiro et al., "Elastase Anti-elastase imbalance in the Pathogens of COPD," Nippon Rinsho (1999), vol. 57, pp. 1982-1987.
Demiryürek, Seniz et al., "Effects of fasudil, a Rho-kinase inhibitor, on myocardial preconditioning in anesthetized rats," European Journal of Pharmacology (2005), vol. 527, pp. 129-140.
Retzer, Michaela et al., "Mildly oxidised low density lipoprotein induces platelet shape change via Rho-kinase-dependent phosphorylation of myosin light chain and moesin," FEBS Letters (2000), vol. 466, pp. 70-74.
Kimura, Kazushi et al., "Regulation of the Association of Adducin with Actin Filaments by Rho-associated Kinase (Rho-kinase) and Myosin Phosphatase," The Journal of Biological Chemistry (1998), vol. 273, pp. 5542-5548.
Fukumoto, Y. et al., "Acute vasodilator effects of a Rho-kinase inhibitor, fasudil, in patients with severe pulmonary hypertension," Heart (2005), vol. 91, pp. 391-392.
Gingras, Denis et al., "Tyrosine phosphorylation of the vascular endothelial-growth-factor receptor-2 (VEGFR-2) is modulated by Rho proteins," Biochemical Journal (2000), vol. 348, pp. 273-280.
Gokina, Natalia I. et al., "Effects of Rho kinase inhibition on cerebral artery myogenic tone and reactivity," Journal of Applied Physiology (2005), vol. 98, pp. 1940-1948.
Yoshida, Yoshiki et al., "Studies on Anti-Helicobacter pylori Agents. Part 1: Benzyloxyisoquinoline Derivatives," Bioorganic and Medicinal Chemistry (1999), vol. 7, pp. 2647-2666.

Hara, Masahito et al., "Protein kinase inhibition by fasudil hydrochloride promotes neurological recovery after spinal cord injury in rats," Journal of Neurosurgery: Spine 1 (2000), vol. 93, pp. 94-101.
Hattori, Tsuyoshi et al., "Long-Term Inhibition of Rho-Kinase Suppresses Left Ventricular Remodeling After Myocardial Infarction in Mice," Circulation (2004), vol. 109, pp. 2234-2239.
Hitomi, Asako et al., "Hemorheological abnormalities in experimental cerebral ischemia and effects of protein kinase inhibitor on blood fluidity," Life Sciences (2000), vol. 67, pp. 1929-1939.
Honjo, Megumi et al., "Effects of Rho-Associated Protein Kinase Inhibitor Y-27632 on Intraocular Pressure and Outflow Facility," Investigative Ophthalmology and Visual Science (2001), vol. 42, pp. 137-144.
Inoue, Makoto et al., "Initiation of neuropathic pain requires lysophosphatidic acid receptor signaling," Nature Medicine (2004), vol. 10, pp. 712-718.
Itoh, Kazuyuki et al., "An essential part for Rho-associated kinase in the transcellular invasion of tumor cells," Nature Medicine (1999), vol. 5, pp. 221-225.
Kawaguchi, Atsuhiro et al., "The effect of a Rho kinase inhibitor Y-27632 on superoxide production, aggregation and adhesion in human polymorphonuclear leukocytes, " European Journal of Pharmacology (2000), vol. 403, pp. 203-208.
Kim, Inkyeom et al., "Thin and Thick Filament Regulation of Contractility in Experimental Cerebral Vasospasm," Neurosurgery (2000), vol. 46, pp. 440-447.
Amano, Mutsuki et al., "Formation of Actin Stress Fibers and Focal Adhesions Enhanced by Rho-Kinase," Science (1997), vol. 275, pp. 1308-1311.
Kishi, Takuya et al., "Rho-Kinase Inhibitor Improves Increased Vascular Resistance and Impaired Vasodilation of the Forearm in Patients with Heart Failure," Circulation (2005), vol. 111, pp. 2741-2747.
Klages, Birgit et al., "Activation of G12/G13 Results in Shape Change and Rho/Rho-Kinase-mediated Myosin Light Chain Phosphorylation in Mouse Platelets," The Journal of Cell Biology (1999), vol. 144, pp. 745-754.
Noma, Kensuke et al., "Physiological role of ROCKs in the cardiovascular systems," American Journal of Physiology: Cell Physiology (2006), vol. 290, pp. C661-668.
Lin, Tong et al., "Rho-ROCK-LIMK-Cofilin Pathway Regulates Shear Stress Activation of Sterol Regulatory Element Binding Proteins," Circulation Research (2003), vol. 92, pp. 1296-1304.
Furukawa, Noboru et al., "Role of Rho-kinase in regulation of insulin action and glucose homeostasis," Cell Metabolism (2005), vol. 2, pp. 119-129.
Masumoto, Akihiro et al., "Suppression of Coronary Artery Spasm by the Rho-Kinase Inhibitor Fasudil in Patients with Vasospastic Angina," Circulation (2002), vol. 105, pp. 1545-1547.
Nakahara, Tsutomu et al., "Y-27632 potentiates relaxant effects of β2—adrenoceptor agonists in bovine tracheal smooth muscle," European Journal of Pharmacology (2000), vol. 389, pp. 103-106.
Pacaud, P. et al., "Rho proteins and vascular diseases," Archives des Maladies du Coeur et des Vaisseaux (2005), vol. 98, pp. 249-254.
Pommereau, Antje et al., "Two Simple and Generic Antibody-Independent Kinase Assays: Comparison of a Bioluminescent and a Microfluidic Assay Format," Journal Biomedical Screening (2004), vol. 9, pp. 409-416.
Remington's Pharmaceutical Sciences 17th Edition (1985), p. 1418.
Retzer, Michaela et al., "Lysophosphatidic acid-induced platelet shape change proceeds via Rho/Rho kinase-mediated myosin light-chain and moesin phosphorylation," Cellular Signalling (2000), vol. 12, pp. 645-648.
Vicente-Manzanares, Miguel et al., "A Role for the Rho-p160 Rho Coiled-Coil Kinase Axis in the Chemokine Stromal Cell-Derived Factor-1α-Induced Lymphocyte Actomyosin and Microtubular Organization and Chemotaxis," The Journal of Immunology (2002), vol. 168, pp. 400-410.
Vicente-Manzanares, Miguel et al., "The RhoA Effector mDia Is Induced During T Cell Activation and Regulates Actin Polymerization and Cell Migration in T Lymphocytes," The Journal of Immunology (2003), vol. 171, pp. 1023-1034.

(56) References Cited

OTHER PUBLICATIONS

Sandu, Oana A. et al., "Diabetes in the Goto-Kakizaki Rat is Accompanied by Impaired Insulin-Mediated Myosin-Bound Phosphatase Activation and Vascular Smooth Muscle Cell Relaxation," Diabetes (2000), vol. 49, pp. 2178-2189.

Sato, Motohiko et al., "Involvement of Rho-Kinase-Mediated Phosphorylation of Myosin Light Chain in Enhancement of Cerebral Vasospasm," Circulation Research (2000), vol. 87, pp. 195-200.

Satoh, Shin-Ichi et al., "Pharmacological profile of hydroxy fasudil as a selective rho kinase inhibitor on ischemic brain damage," Life Sciences (2001), vol. 69, pp. 1441-1453.

Setoguchi, Hidekazu et al., "Leukotriene C4 enhances the contraction of porcine tracheal smooth muscle through the activation of Y-27632, a rho kinase inhibitor, sensitive pathway," British Journal of Pharmacology (2001), vol. 132, pp. 111-118.

Shimokawa, Hiroaki et al., "Anti-anginal Effect of Fasudil, a Rho-Kinase Inhibitor, in Patients With Stable Effort Angina: A Multicenter Study," Journal of Cardiovascular Pharmacology (2002), vol. 40, pp. 751-761.

Steioff, Kerstin et al., "Long term Rho-kinase inhibition ameliorates endothelial dysfunction in LDL-Receptor deficient mice," European Journal of Pharmacology (2005), vol. 512, pp. 247-249.

Seasholtz, Tammy M. et al., "Rho and Rho Kinase Mediate Thrombin-Stimulated Vascular Smooth Muscle Cell DNA Synthesis and Migration," Circulation Research (1999), vol. 84, pp. 1186-1193.

Tatsumi, S. et al., "Involvement of Rho-Kinase in Inflammatory and Neuropathic Pain Through Phosphorylation of Myristoylated Alanine-Rich C-Kinase Substrate (Marcks)," Neuroscience (2005), vol. 131, pp. 491-498.

Forzato, Cristina et al., "Baker's yeast reduction of 4-hetero-2-(2-nitroethyl)cyclohexanones," Tetrahedron: Asymmetry (1997), vol. 8, pp. 1811-1820.

Uehata, Masayoshi et al., "Calcium sensitization of smooth muscle mediated by a Rho-associated protein kinase in hypertension," Nature (1997), vol. 389, pp. 990-994.

Yamakawa, Tadashi et al., "Involvement of Rho-Kinase in Angiotensin II-Induced Hypertrophy of Rat Vascular Smooth Muscle Cells," Hypertension (2000), vol. 35, pp. 313-318.

Yamamoto, Yasuhiro et al., "The Protein Kinase Inhibitor Fasudil Protects Against Ischemic Myocardial Injury Induced by Endothelin-1 in the Rabbit," Journal of Cardiovascular Pharmacology (2000), vol. 35, pp. 203-211.

Totsukawa, Go et al., "Distinct Roles of ROCK (Rho-kinase) and MLCK in Spatial Regulation of MLC Phosphorylation for Assembly of Stress Fibers and Focal Adhesions in 3T3 Fibroblasts," The Journal of Cell Biology (2000), vol. 150, pp. 797-806.

Yoshii, Akihiro et al., "Relaxation of Contracted Rabbit Tracheal and Human Bronchial Smooth Muscle by Y-27632 through Inhibition of Ca2+ Sensitization," American Journal of Respiratory Cell and Molecular Biology (1999), vol. 20, pp. 1190-1200.

Zhou, Yan et al., "Nonsteroidal Anti-Inflammatory Drugs Can Lower Amyloidogenic Aβ42 by Inhibiting Rho," Science (2003), vol. 302, pp. 1215-1217.

Okada, Hiroshi et al., "Synthesis and Antitumor Activities of Prodrugs of Benzoylphenylureas," Chemical and Pharmaceutical Bulletin (1994), vol. 42, pp. 57-61.

Negoro, Nobuyuki et al., "The Kinase Inhibitor Fasudil (HA-1077) Reduces Intimal Hyperplasia through Inhibiting Migration and Enhancing Cell Loss of Vascular Smooth Muscle Cells," Biochemical and Biophysical Research Communications (1999), vol. 262, pp. 211-215.

Somlyo, Avril V. et al., "Rho-Kinase Inhibitor Retards Migration and in Vivo Dissemination of Human Prostate Cancer Cells," Biochemical and Biophysical Research Communications (2000), vol. 269, pp. 652-659.

Uchida, Shigeki et al., "The Suppression of Small GTPase Rho Signal Transduction Pathway Inhibits Angiogenesis in Vitro and in Vivo," Biochemical and Biophysical Research Communications (2000), vol. 269, pp. 633-640.

Wakino, Shu et al., "Rho/Rho Kinase as a Potential Target for the Treatment of Renal Disease," Drug News and Perspectives (2005), vol. 18, pp. 639-643.

J. Bonjoch, et al., Tetrahedron Letter., 2003, 44, 8387.

Iwakubo, M., et al., Design and Synthesis of Rho Kinase Inhibitors (III), Bioorganic & Medicinal Chemistry, vol. 15, (2007), pp. 1022-1033.

Iwakubo, M, et al. Design and Synthesis of Rho Kinase Inhibitors (II), Bioorganic & Medicinal Chemistry, vol. 15, (2007), pp. 350-364.

Curran, T.T., et al., The preparation of Optically Active 2-Cyclopenten-1-4-Diol Derivatives from Furfuryl Alcohol, Tetrahedron, vol. 53, No. 6, p. 1983-2004., 1997.

Tamura, M., et al., Development of Specific Rho-Kinase Inhibitors and Their Clinical Application, Biochimica et Biophysica Acta. (2005), vol. 1754, pp. 245-252.

Becker, Daniel P., et al., "A Short Synthesis of 1-Azaadamantan-4-one and the 4r and 4s Isomers of 4-Amino-1-azadamantane", Synthesis (1992) vol., 11, pp. 1080-1082.

Degraffenreid, Michael R., et al., "An Efficient and Scalable One-Pot Double Michael Addition-Diectramann Condensation for the Synthesis of 4,4-Disubstituted Cyclohexane B-ketosis", Journal of Organic Chemistry (2007), vol. 72, pp. 7455-7458.

Lednicer, Daniel, et al., "4-amino-4-aryl cyclohexanones and their derivatives, A Novel Class of Analgesics-1 Modification of the Aryl Ring". Journal of Medicinal Chemistry (1980), vol. 23, pp. 424-430.

Caron, Stephane, et al., "The Synthesis of a Selective PDE/TnFa Inhibitor", Organic Process Research and Development (2001), vol. 5, pp. 587-592.

U.S. Appl. No. 12/970,376 to Plettenburg, et al., filed Dec. 16, 2010.
U.S. Appl. No. 13/000,754 to Plettenburg, et al., filed Apr. 20, 2011.
U.S. Appl. No. 13/000,202 to Plettenburg, et al., filed Dec. 20, 2010.
U.S. Appl. No. 11/961,197 to Plettenburg, et al, filed Dec. 20, 2007.
U.S. Appl. No. 12/019,866 to Plettenburg, et al., filed Jan. 25, 2008.
U.S. Appl. No. 12/069,799 to Plettenburg, et. al., filed Jan. 25, 2008.
U.S. Appl. No.. 12/487,479 to Plettenburg, et al., filed Jun. 18, 2009.
U.S. Appl. No. 12/467,455 to Plettenburg, et al., filed Jun. 18, 2009.
U.S. Appl. No. 12/487,403 to Plettenburg, et al., filed Jun. 18, 2009.
U.S. Appl. No. 12/487,409 to Plettenburg, et al. filed Jun. 18, 2009.
U.S. Appl. No. 12/467,386 to Plettenburg, et al., filed Jun. 18, 2009.
U.S. Appl. No. 12/487,503 to Plettenburg, et al., filed Jun. 18, 2009.
U.S. Appl. No. 12/487,525 to Plettenburg, et al., filed Jun. 18, 2009.

Daviglus, Martha L., et al., National Institutes of Health State-of-the-Science Conference Statement: Preventing Alzheimer Disease and Cognitive Decline, Annals of Internal Medicine, (Aug. 3, 2010), vol. 153, No. 3, pp. 176-186.

Michel Goedert, et al., A Century of Alzheimer's Disease, Science, (Nov. 2, 2006), vol. 314, pp. 777-781.

Office Action dated Jul. 17, 2013 received in a related U.S. Patent Application, namely U.S. Appl. No. 13/161,003.

CYCLOHEXYLAMIN ISOQUINOLONE DERIVATIVES

This application is a CON of PCT/EP2006/007140 filed Jul. 20, 2006.

The present invention relates to novel isoquinolone and isoquinoline derivatives as described in the claims, their preparation and their use in the treatment and/or prevention of diseases related to the inhibition of Rho-kinase and/or of Rho-kinase mediated phosphorylation of myosin light chain phosphatase.

Activation of a small GTPase RhoA upon agonist stimulation results in conversion of RhoA from the inactive GDP-bound form to the active GTP-bound form with a subsequent binding to and activation of Rho-kinase. Two isoforms, Rho-kinase 1 and Rho-kinase 2, are known. Rho-kinase 2 is expressed in vascular smooth muscle cells and endothelial cells. Activation of Rho-kinase 2 by the active GTP-bound RhoA leads to calcium sensitization of smooth muscle cells through phosphorylation-mediated inhibition of the myosin light chain phosphatase activity and thereby up-regulation of the activity of myosin regulatory light chain (Uehata et al., Nature 1997, 389, 990-994).

It is known that Rho-kinase is involved in vasoconstriction, including the development of myogenic tone and smooth muscle hypercontractility (Gokina et al. J. Appl. Physiol. 2005, 98, 1940-8), bronchial smooth muscle contraction (Yoshii et al. Am. J. Resp. Cell Mol. Biol. 20, 1190-1200), asthma (Setoguchi et al. Br J. Pharmacol. 2001, 132,111-8; Nakahara, et al. Eur J 2000, 389, 103) and chronic obstructive pulmonary disease (COPD, Maruoka, Nippon Rinsho, 1999, 57, 1982-7), hypertension, pulmonary hypertension (Fukumoto et al. Heart, 91, 391-2, 2005, Mukai et al. Nature 1997, 389, 990-4) and ocular hypertension and regulation of intraocular pressure (Honjo et al. Invest. Ophthalmol. Visual Sci. 2001, 42, 137-144), endothelial dysfunction (Steioff et al. Eur. J. Pharmacol. 2005, 512, 247-249), angina (Masumoto et al. Circ 2002, 105, 1545-47, Shimokawa et al. JCP, 2002, 40, 751-761), nephropathy, including hypertension-induced, non-hypertension-induced, and diabetic nephropathies, renal failure and peripheral occlusive arterial disease (PAOD) (Wakino et al. Drug News Perspect. 2005, 18, 639-43), myocardial infarction (Demiryurek et al. Eur J. Pharmacol. 2005, 527, 129-40, Hattori et al. Circulation, 2004, 109, 2234-9), cardiac hypertrophy and failure (Yamakawa, et al. Hypertension 2000, 35, 313-318, Liao et al. Am J Physiol Cell Physiol. 2006, 290, C661-8, Kishi et al. Circ 2005, 111, 2741-2747), coronary heart disease, artherosclerosis, restenosis (Pacaud et al. Arch. Mal. Coeur 2005, 98, 249-254, Retzer, et al. FEBS Lett 2000, 466, 70, Negoro, et al. Biochem Biophys Res Commun 1999, 262, 211), diabetes, diabetic complications, glucose utilization and metabolic syndrome (Sandu, et al. Diabetes 2000, 49, 2178, Maeda et al. Cell Metab. 2005, 2, 119-29), sexual dysfunction, e.g., penile erectile dysfunction (Chitaley et al. Nature Medicine 2001, 7, 119-122), retinopathy, inflammation, immune diseases, AIDS, osteoporosis, endocrine dysfunctions, e.g. hyperaldosteronism, central nervous system disorders such as neuronal degeneration and spinal cord injury (Hara, et al. JNeurosurg 2000, 93, 94), cerebral ischemia (Uehata, et al. Nature 1997, 389, 990; Satoh et al. Life Sci. 2001, 69, 1441-53; Hitomi, et al. Life Sci 2000, 67, 1929; Yamamoto, et al. J Cardiovasc Pharmacol. 2000, 35, 203-11), cerebral vasospasm (Sato, et al. Circ Res 2000, 87, 195; Kim, et al. Neurosurgery 2000, 46, 440), pain, e.g. neuropathic pain (Tatsumi, et al. Neuroscience 2005, 131, 491, Inoue, et al. Nature medicine 2004, 10, 712), infection of digestive tracts with bacteria (WO 98/06433), cancer development and progression, neoplasia where inhibition of Rho kinase has been shown to inhibit tumor cell growth and metastasis (Itoh, et al. Nature Medicine 1999, 5, 221; Somlyo, et al. Res Commun 2000, 269, 652), angiogenesis (Uchida, et al. Biochem Biophys Res 2000, 269, 633-40; Gingras, et al. Biochem J 2000, 348, 273), vascular smooth muscle cell proliferation and motility (Tammy et al. Circ. Res. 1999, 84, 1186-1193; Tangkijvanich et al. Atherosclerosis 2001, 155, 321-327), endothelial cell proliferation, endothelial cell retraction and motility (Oikawa et al. Biochem. Biophys. Res. Commun. 2000, 269, 633-640), stress fiber formation (Kimura et al. Science 1997, 275, 1308-1311; Yamashiro et al. J. Cell Biol. 2000, 150, 797-806), thrombotic disorders (Kikkawa, et al. FEBS Lett. 2000, 466, 70-74; Bauer et al. Blood 1999, 94, 1665-1672, Klages, et al. J Cell Biol 1999, 144, 745; Retzer, et al. Cell Signal 2000, 12, 645) and leukocyte aggregation (Kawaguchi, et al. Eur J. Pharmacol. 2000, 403:203-8; Sanchez-Madrid, et al. J. Immunol. 2003, 171:1023-34, Sanchez-Madrid, et al. J. Immunol. 2002, 168:400-10), and bone resorption (Chellaiah, et al. J Biol. Chem. 2003, 278:29086-97). Na/H exchange transport system activation (Kawaguchi, et al. Eur J. Pharmacol. 2000, 403:203-8), Alzheimer's disease (Zhou et al. Science 2003, 302, 1215-1217), adducin activation (Fukata et al. J. Biol. Chem., 1998, 273, 5542-5548), and in SREB (Sterol response binding element) signalling and its effects on lipid metabolism (Lin et al. Circ. Res., 92, 1296-304, 2003).

Therefore, a compound having inhibitory effect on Rho-kinase and/or on Rho-kinase mediated phosphorylation of myosin light chain phosphatase is useful for the treatment and/or prevention of cardiovascular and non-cardiovascular diseases involving Rho-kinase as the primary or secondary disease cause, like hypertension, pulmonary hypertension, ocular hypertension, retinopathy, and glaucoma, peripheral circulatory disorder, peripheral occlusive arterial disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

WO 01/64238 describes isoquinoline-5-sulfonamide derivatives optionally substituted by a $-(CH_2)_{1-6}-O-(CH_2)_{0-6}-$, a $-(CH_2)_{0-6}-S-(CH_2)_{0-6}-$ or a $-(CH_2)_{0-6}-$ linked heterocyclic group useful as neuroprotective agents.

WO 2004/106325 (Schering AG) describes prodrugs of the Rho-kinase inhibitor fasudil carrying an ether or ester group in the 1-position of the isoquinoline ring.

WO 2001/039726 generically describes $-O-(C_0-C_{10})$ alkyl-heteroaryl substituted cyclohexyl derivatives useful for the treatment of microbial infections.

JP 10087629 A describes isoquinoline derivatives useful for the treatment of diseases caused by *Heliobacter pylori* such as for example gastritis cancer or ulcer; the isoquinoline derivatives may be substituted by OH in the 1-position and are preferably 5-substituted by X—[($C_1$-$C_6$)alkylene)]$_{0-1}$-Y wherein X may be oxygen and Y may be an aryl or a heterocyclic group.

Yoshida et al. (Bioorg. Med. Chem. 1999, 7, 2647-2666) disclose 6-benzyloxy-isoquinoline for the treatment of infections caused by *Heliobacter pylori*.

U.S. Pat. No. 5,480,883 generically discloses as EGF and/or PDGF receptor inhibitors useful for inhibiting cell proliferation compounds of the formula "Ar I-X—Ar II" wherein X may be $(CHR_1)_m$—Z—$(CHR_1)_n$, e.g. Z—$CH_2$, wherein Z may be O, $R_1$ is hydrogen or alkyl, Ar I may be among others an optionally substituted isoquinolone and Ar II may be among others optionally substituted cyclohexyl.

WO 2005/030791 (Merck & Co.) generically describes as potassium channel inhibitors for the treatment of cardiac arrhythmias, stroke, congestive heart failure etc. isoquinolone derivatives which are optionally substituted in 6-position by a group $(CR^eR^f)_pOR^{43}$ wherein p may be zero, and $R^{43}$ is e.g. a ($C_3$-$C_{10}$)cycloalkyl residue optionally substituted by $NR^{51}\beta^{52}$, wherein $R^{51}$ and $R^{52}$ may be hydrogen, ($C_1$-$C_6$) alkyl etc.; or $R^{43}$ is a group $R^{81}$ defined as a 4-6 membered unsaturated or saturated monocyclic heterolylic ring with 1, 2, 3 or 4 heteroatoms; and are substituted by a directly bound optionally substituted aryl or heteroaryl ring in the 4-position.

WO 2005/030130 (Merck & Co.) generically describes as potassium channel inhibitors for the treatment of cardiac arrhythmias, stroke, congestive heart failure etc. isoquinoline derivatives which may be substituted by hydroxyl in the 1-position and are optionally substituted in 6-position by a group $(CR^eR^f)_pOR^{43}$ wherein p may be zero, and $R^{43}$ is e.g. a ($C_3$-$C_{10}$)cycloalkyl residue optionally substituted by $NR^{51}\beta^{52}$, wherein $R^{51}$ and $R^{52}$ may be hydrogen, ($C_1$-$C_6$)alkyl etc.; or $R^{43}$ is a group $R^{81}$ defined as a 4-6 membered unsaturated or saturated monocyclic heterocyclic ring with 1, 2, 3 or 4 heteroatoms; and are substituted by a directly bound optionally substituted aryl or heteroaryl ring in the 4-position.

WO 03/053330 (Ube) describes isoquinolone derivatives of the formula

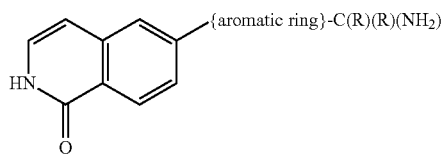

as Rho-kinase inhibitors.

An embodiment of the present invention is a compound of the formula (I)

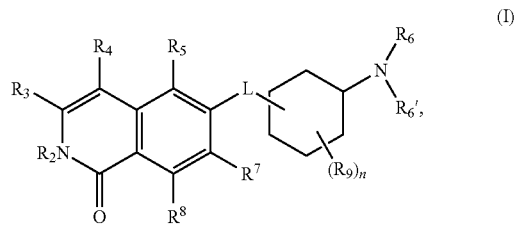

wherein $R_2$ is H, ($C_1$-$C_6$)alkyl, [($C_1$-$C_6$)alkylene]$_{0-1}$-R', [($C_1$-$C_6$)alkylene]$_{0-1}$-O—($C_1$-$C_6$)alkyl, [($C_1$-$C_6$)alkylene]$_{0-1}$-O—R', [($C_1$-$C_6$)alkylene]$_{0-1}$-$NH_2$, [($C_1$-$C_6$)alkylene]$_{0-1}$-NH($C_1$-$C_6$) alkyl, [($C_1$-$C_6$)alkylene]$_{0-1}$-N[($C_1$-$C_6$)alkyl]$_2$, [($C_1$-$C_6$)alkylene]$_{0-1}$-CH[R']$_2$, [($C_1$-$C_6$)alkylene]$_{0-1}$-C(O)—R', [($C_1$-$C_6$) alkylene]$_{0-1}$—C(O)$NH_2$, [($C_1$-$C_6$)alkylene]$_{0-1}$-C(O)NH—R', or [($C_1$-$C_6$)alkylene]$_{0-1}$-C(O)N[R']$_2$;

$R_3$ is H, halogen, CN, ($C_1$-$C_6$)alkyl, ($C_1$-$C_6$)alkylene-R', OH, O—R", $NH_2$, NHR", NR"R" or NH—C(O)—R", $R_4$ is H, halogen, hydroxy, CN, ($C_1$-$C_6$)alkyl, ($C_3$-$C_8$)cycloalkyl, ($C_1$-$C_6$)alkylene-R';

$R_5$ is H, halogen, CN, $NO_2$, ($C_1$-$C_6$)alkyl, ($C_2$-$C_6$)alkenyl, R', ($C_1$-$C_6$)alkylene-($C_6$-$C_{10}$)aryl, ($C_2$-$C_6$)alkenylene-($C_6$-$C_{10}$) aryl, ($C_1$-$C_6$)alkylene-($C_5$-$C_{10}$)heterocyclyl, $NH_2$, NH—R', NH—$SO_2$H, NH—$SO_2$—($C_1$-$C_6$)alkyl, NH—$SO_2$—R', NH—C(O)—($C_1$-$C_6$)alkyl, NH—C(O)—R', C(O)N[($C_1$-$C_6$) alkyl]$_2$, C(O)OH or C(O)O—($C_1$-$C_6$)alkyl;

$R_6$ and $R_6$' are independently of each other H, R', ($C_1$-$C_8$) alkyl, ($C_1$-$C_6$)alkylene-R', ($C_1$-$C_6$)alkylene-O—($C_1$-$C_6$) alkyl, ($C_1$-$C_6$)alkylene-O—R', ($C_1$-$C_6$)alkylene-CH[R']$_2$, ($C_1$-$C_6$)alkylene-C(O)—R', ($C_1$-$C_6$)alkylene-C(O)$NH_2$, ($C_1$-$C_6$)alkylene-C(O)NH—R', or ($C_1$-$C_6$)alkylene-C(O)N[R']$_2$;

$R_7$ and $R_8$ are independently of each other H, halogen, CN, $NO_2$, ($C_1$-$C_6$)alkyl, O—($C_1$-$C_6$)alkyl, O—[($C_1$-$C_6$)alkylene]$_{0-1}$—R', ($C_2$-$C_6$)alkenyl, R', ($C_2$-$C_6$)alkenylene-($C_6$-$C_{10}$) aryl, ($C_1$-$C_6$)alkylene-R', $NH_2$, NH—R', NH—$SO_2$H, NH—$SO_2$—($C_1$-$C_6$)alkyl, NH—$SO_2$—R', $SO_2$—$NH_2$, $SO_2$—NHR', NH—C(O)—($C_1$-$C_6$)alkyl, NH—C(O)—R', C(O)N[($C_1$-$C_6$)alkyl]$_2$, C(O)OH or C(O)O—($C_1$-$C_6$)alkyl;

$R_9$ is halogen or ($C_1$-$C_6$)alkyl;

n is 0, 1, 2, 3 or 4; and

L is O or O—($C_1$-$C_6$)alkylene;

wherein R' is ($C_3$-$C_8$)cycloalkyl, ($C_5$-$C_{10}$)heterocyclyl or ($C_6$-$C_{10}$)aryl; and R" is ($C_3$-$C_8$)cycloalkyl, ($C_5$-$C_{10}$)heterocyclyl, ($C_6$-$C_{10}$)aryl, ($C_1$-$C_6$)alkyl, ($C_1$-$C_6$)alkylene-R', ($C_1$-$C_6$)alkylene-O—($C_1$-$C_6$)alkyl, ($C_1$-$C_6$)alkylene-O—R', or ($C_1$-$C_6$)alkylene-$NR_xR_y$; and wherein $R_x$ and $R_y$ are independently of each other ($C_1$-$C_6$) alkyl, ($C_5$-$C_{10}$)heterocyclyl, ($C_6$-$C_{10}$)aryl, ($C_1$-$C_4$)alkylene-($C_5$-$C_{10}$)heterocyclyl, ($C_1$-$C_4$)alkylene-($C_6$-$C_{10}$)aryl, ($C_1$-$C_4$)alkylene-NH($C_1$-$C_6$)alkyl, ($C_1$-$C_4$)alkylene-N[($C_1$-$C_6$) alkyl]$_2$, ($C_1$-$C_4$)alkylene-N[($C_6$-$C_{10}$)aryl]$_2$, or ($C_1$-$C_4$) alkylene-N[($C_5$-$C_{10}$)heterocyclyl]$_2$; and wherein in residues $R_4$, $R_5$, $R_7$ and $R_8$ one alkyl or alkylene hydrogen atom can optionally be substituted by OH, $OCH_3$, COOH, $COOCH_3$, $NH_2$, $NHCH_3$, $N(CH_3)_2$, $CONH_2$, $CONHCH_3$ or $CON(CH_3)_2$ or an alkyl or alkylene may be halogenated once or more;

or their pharmaceutically acceptable salts and/or stereoisomeric forms and/or physiologically functional derivatives.

In another embodiment of a compound of formula (I) in residues $R_4$, $R_5$, $R_7$ and $R_8$ one alkyl or alkylene hydrogen atom can optionally be substituted by OH, F, $OCH_3$, COOH, $COOCH_3$, $NH_2$, $NHCH_3$, $N(CH_3)_2$, $CONH_2$, $CONHCH_3$ or $CON(CH_3)_2$.

Stereoisomeric forms of the isoquinolone derivatives of the formula (I) include the corresponding tautomeric 1-hydroxy-substituted isoquinoline derivatives of the formula (I')

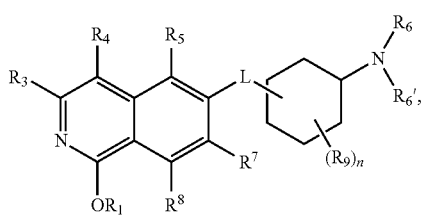

(I')

wherein $R_1$ is H, $(C_1-C_6)$alkyl, $(C_2-C_6)$alkenyl, $(C_2-C_6)$alkynyl, $[(C_1-C_6)$alkylene$]_{0-1}$-$(C_3-C_8)$cycloalkyl, $[(C_1-C_6)$alkylene$]_{0-1}$-$(C_5-C_{10})$heterocyclyl, $[(C_1-C_6)$alkylene$]_{0-1}$-$(C_6-C_{10})$aryl, C(O)—$(C_1-C_6)$alkyl, C(O)$(C_2-C_6)$alkenyl, C(O)—$(C_2-C_6)$alkynyl, C(O)-$[(C_1-C_6)$alkylene$]_{0-1}$-$(C_3-C_8)$cycloalkyl, C(O)-$[(C_1-C_6)$alkylene$]_{0-1}$-$(C_5-C_{10})$heterocyclyl, or C(O)-$[(C_1-C_6)$alkylene$]_{0-1}$-$(C_6-C_{10})$aryl, and wherein $R_3$, $R_4$, $R_5$, $R_6$, $R_6'$, $R_7$, $R_8$, $R_9$, n and L are as defined above.

In a preferred embodiment, $R_2$ in the compound of the formula (I) is H, the compound is thus characterized by a compound of the formula (II)

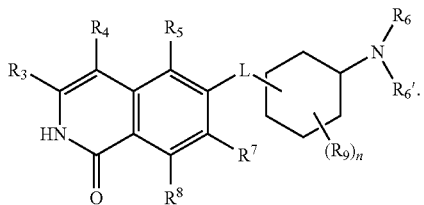

(II)

In a further preferred embodiment, $R_1$ in the compound of the formula (I') is H, the compound is thus characterized by a compound of the formula (II')

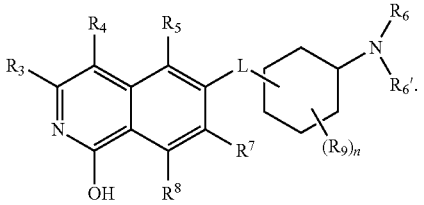

(II')

The compounds (II) and (II') are tautomeric forms of each other.

For example the compound having the formula

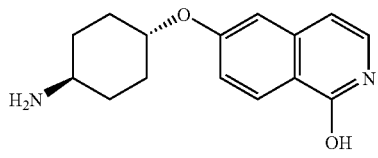 [SMILES: N[C@H]1CC[C@H](Oc2ccc3c(O)nccc3c2)CC1]

is a tautomeric form of the compound with the formula

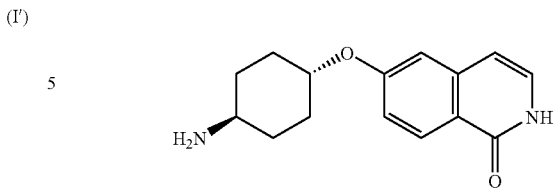

The following preferred embodiments refer to the compounds of the formulae (I), (I'), (II) and (II'):
$R_3$ is preferably H, halogen, $(C_1-C_6)$alkyl, $(C_1-C_4)$alkylene-R', O—R" or NHR". More preferred, $R_3$ is H, $(C_1-C_6)$alkyl or NHR". Most preferred, $R_3$ is H, $(C_1-C_4)$alkyl, NH—$(C_5-C_6)$heterocyclyl or NH-phenyl, especially preferred $R_3$ is H, $(C_1-C_4)$alkyl, NH—$(C_5-C_6)$heteroaryl containing one or more N atoms or NH-phenyl. Most especially preferred, $R_3$ is H.

Preferably, $R_4$ is H, halogen, CN, $(C_1-C_6)$alkyl, NH—$(C_6-C_{10})$aryl or $(C_1-C_6)$alkylene-R'. More preferably, $R_4$ is H, halogen, $(C_1-C_6)$alkyl, NH—$(C_6-C_{10})$aryl or $(C_1-C_6)$alkylene-R'. In a further preferred embodiment, $R_4$ is H, halogen, $(C_1-C_6)$alkyl, NH—$(C_6-C_{10})$aryl or $(C_1-C_2)$alkylene-$(C_6-C_{10})$aryl. Most preferred, $R_4$ is H, halogen, or $(C_1-C_6)$alkyl. Especially preferred, $R_4$ is H, halogen or $(C_1-C_6)$alkyl. More especially preferred, $R_4$ is H or $(C_1-C_6)$alkyl. Most especially preferred, $R_4$ is H.

Preferably, $R_5$ is H, halogen, CN, $(C_1-C_6)$alkyl, R', NH—$(C_6-C_{10})$aryl or $(C_1-C_6)$alkylene-R'. More preferably, $R_5$ is H, halogen, $(C_1-C_6)$alkyl, R', NH—$(C_6-C_{10})$aryl or $(C_1-C_6)$alkylene-R'. In a further preferred embodiment, $R_5$ is H, halogen, $(C_6-C_{10})$aryl, NH—$(C_6-C_{10})$aryl, $(C_1-C_2)$alkylene-$(C_6-C_{10})$aryl, $(C_1-C_6)$alkyl or $(C_5-C_{10})$heteroaryl. Most preferred, $R_5$ is H, halogen, phenyl, $(C_1-C_6)$alkyl or $(C_5-C_6)$heteroaryl. Especially preferred, $R_5$ is H, halogen or $(C_1-C_6)$alkyl. More especially preferred, $R_5$ is H or halogen. Most especially preferred, $R_5$ is H.

Preferably, $R_6$ and $R_6'$ are independently of each other H, $(C_1-C_6)$alkyl, R', $(C_1-C_4)$alkylene-$(C_3-C_8)$cycloalkyl, $(C_1-C_4)$alkylene-$(C_5-C_{10})$heterocyclyl, $(C_1-C_4)$alkylene-C(O)—$(C_5-C_{10})$heterocyclyl, $(C_1-C_4)$alkylene-C(O)—$(C_6-C_{10})$aryl or $(C_1-C_6)$alkylene-$(C_6-C_{10})$aryl. In a further preferred embodiment, $R_6$ and $R_6'$ are independently of each other H, $(C_1-C_6)$alkyl, $(C_5-C_{10})$heterocyclyl, $(C_3-C_8)$cycloalkyl, $(C_1-C_4)$alkylene-$(C_3-C_8)$cycloalkyl, $(C_1-C_4)$alkylene-$(C_5-C_{10})$heterocyclyl or $(C_1-C_4)$alkylene-$(C_6-C_{10})$aryl. In a more preferred embodiment, $R_6$ is H, $(C_1-C_6)$alkyl, $(C_3-C_6)$cycloalkyl or $(C_1-C_4)$alkylene-$(C_3-C_6)$cycloalkyl, and $R_6'$ is H, $(C_1-C_6)$alkyl, $(C_3-C_8)$cycloalkyl, $(C_1-C_4)$alkylene-$(C_3-C_8)$cycloalkyl, $(C_5-C_{10})$heterocyclyl, $(C_1-C_4)$alkylene-$(C_5-C_{10})$heterocyclyl or $(C_1-C_6)$alkylene-$(C_6-C_{10})$aryl. In a further more preferred embodiment, $R_6$ is H, $(C_1-C_6)$alkyl and $R_6'$ is H, $(C_1-C_6)$alkyl, $(C_3-C_8)$cycloalkyl, $(C_1-C_4)$alkylene-$(C_3-C_8)$cycloalkyl, $(C_5-C_{10})$heterocyclyl, $(C_1-C_4)$alkylene-$(C_5-C_{10})$heterocyclyl or $(C_1-C_6)$alkylene-$(C_6-C_{10})$aryl. In a further even more preferred embodiment, $R_6$ is H, $(C_1-C_6)$alkyl and $R_6'$ is H, $(C_1-C_6)$alkyl, $(C_3-C_8)$cycloalkyl, $(C_1-C_4)$alkylene-$(C_3-C_8)$cycloalkyl, $(C_1-C_4)$alkylene-$(C_5-C_{10})$heterocyclyl in which heterocyclyl is unsubstituted or substituted by $(C_1-C_4)$alkyl or halogen, or is $(C_1-C_6)$alkylene-$(C_6-C_{10})$aryl in which aryl is unsubstituted or substituted by halogen, $(C_1-C_4)$alkyl especially $CH_3$ or $CF_3$, O—$(C_1-C_4)$alkyl especially O—$CH_3$, or $SO_2$—$(C_1-C_4)$alkyl especially $SO_2$—$CH_3$ or $SO_2$—$CF_3$. In a most preferred embodiment, $R_6$ is H, $(C_1-C_6)$alkyl and $R_6'$ is H, $(C_1-C_6)$alkyl, $(C_3-C_8)$cycloalkyl. In a further most preferred embodiment, $R_6$ is H and $R_6'$ is H, $(C_1-C_6)$alkyl, $(C_3-C_8)$cycloalkyl. Especially preferred, $R_6$ and $R_6'$ are H.

As examples for these embodiments, $R_6$ or $R_6'$ are, independently from each other, hydrogen, methyl, ethyl, propyl, isopropyl, 3-methyl-butyl, 2-methyl-propyl, butyl, pentyl, 3,3,3-trifluoropropyl, 4,4,4-trifluorobutyl or a substituent selected from the group consisting of

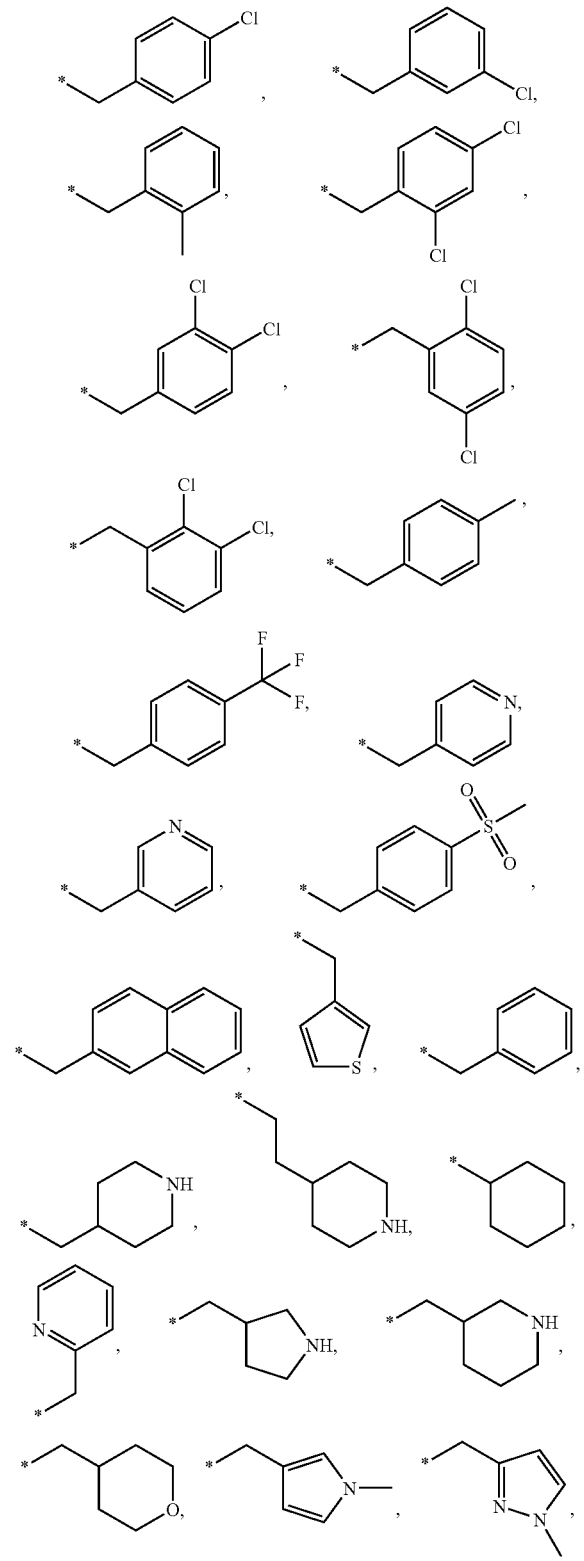

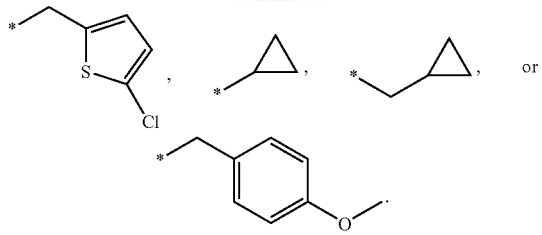

Preferably, $R_7$ and $R_8$ are independently of each other H, halogen, CN, $(C_1-C_6)$alkyl, O—$(C_1-C_6)$alkyl, $(C_2-C_6)$alkenyl, R' or $(C_1-C_6)$alkylene-$(C_3-C_8)$cycloalkyl. More preferred, $R_7$ and $R_8$ are independently of each other H, halogen, CN, $(C_1-C_4)$alkyl, O—$(C_1-C_4)$alkyl, $(C_2-C_4)$alkenyl, phenyl, $(C_3-C_6)$cycloalkyl, $(C_1-C_4)$alkylene-$(C_3-C_6)$cycloalkyl or $(C_5-C_6)$heteroaryl. Even more preferred, $R_7$ and $R_8$ are independently of each other H, halogen, $(C_1-C_4)$alkyl, O—$(C_1-C_4)$alkyl or $(C_3-C_6)$cycloalkyl. Most preferably, $R_7$ is H, halogen, $(C_1-C_4)$alkyl or $(C_3-C_6)$cycloalkyl and $R_8$ is H. Especially preferred, $R_7$ and $R_8$ are H.

$R_9$ is preferably halogen or $(C_1-C_4)$alkyl. More preferred, $R_9$ is Cl, F, methyl or ethyl.

Preferably, n is 0, 1, 2 or 3. More preferred, n is 0 or 1. Most preferred, n is 0.

The linker group L may be bound to the cyclohexyl ring in any position via a cyclohexyl ring carbon atom and may thereby form the cis- or the trans-stereoisomer of a compound according to the invention.

In a preferred embodiment, L is attached to the 4-position of the cyclohexyl ring

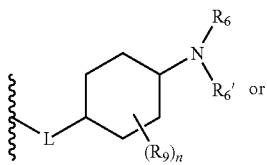

L is attached to the 3-position of the cyclohexyl ring

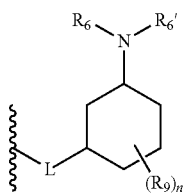

in all their stereoisomeric forms.

In an especially preferred embodiment, L is attached to the 4-position of the cyclohexyl ring.

Preferably, L is O-methylene, O-ethylene or O. More preferably, L is O-methylene, O-ethylene or most preferred O attached to the 4-position of the cyclohexyl ring.

Most preferably, L is O.

In preferred embodiments of the present invention one or more or all of the groups contained in the compounds of formulae (I) or (I') can independently of each other have any of the preferred, more preferred or most preferred definitions of the groups specified above or any one or some of the specific denotations which are comprised by the definitions of the groups and specified above, all combinations of preferred definitions, more preferred or most preferred and/or specific denotations being a subject of the present invention. Also with respect to all preferred embodiments the invention includes the compounds of the formulae (I) or (I') in all stereoisomeric forms and mixtures of stereoisomeric forms in all ratios, and/or their physiologically acceptable salts.

A preferred embodiment of the present invention is a compound of the formulae (I), (I'), (II) or (II') wherein
$R_3$ is H, halogen, CN, $(C_1-C_6)$alkyl, $(C_1-C_6)$alkylene-R', OH, O—R", $NH_2$, or NHR";
$R_4$ is H, halogen, hydroxy, CN, $(C_1-C_6)$alkyl, $(C_3-C_8)$cycloalkyl, $(C_1-C_6)$alkylene-R';
$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, $NH_2$, NH—R', NH—$SO_2\beta$, NH—$SO_2$—$(C_1-C_6)$alkyl, NH—$SO_2$—R', NH—C(O)—$(C_1-C_6)$alkyl, NH—C(O)—R', $C(O)N[(C_1-C_6)$alkyl$]_2$, C(O)OH or C(O)O—$(C_1-C_6)$alkyl;
$R_6$ and $R_6'$ are independently of each other H, $(C_3-C_8)$cycloalkyl, $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)$NH_2$, $(C_1-C_6)$alkylene-C(O)NH—R', or $(C_1-C_6)$alkylene-C(O)N[R']$_2$;
$R_7$ and $R_8$ are independently of each other H, halogen, CN, $NO_2$, $(C_1-C_6)$alkyl, $(C_2-C_6)$alkenyl, R', $(C_2-C_6)$alkenylene-$(C_6-C_{10})$aryl, $(C_1-C_6)$alkylene-R', $NH_2$, NH—R', NH—$SO_2$—$(C_1-C_6)$alkyl, NH—$SO_2$—R', $SO_2$—$NH_2$, $SO_2$—NHR', NH—C(O)—$(C_1-C_6)$alkyl, NH—C(O)—R', $C(O)N[(C_1-C_6)$alkyl$]_2$, C(O)OH or C(O)O—$(C_1-C_6)$alkyl;
$R_9$ is halogen or $(C_1-C_6)$alkyl;
n is 0, 1, 2; and
L is O or O—$(C_1-C_3)$alkylene;
wherein $R_1$, $R_2$, R', R", Rx and Ry are as defined above;
or their pharmaceutically acceptable salts and/or stereoisomeric forms and/or physiologically functional derivatives.

A further preferred embodiment of the present invention is a compound of the formulae (I), (I'), (II) or (II') wherein
$R_3$ is H, halogen, CN, $(C_1-C_6)$alkyl, $(C_1-C_2)$alkylene-R' or NHR";
$R_4$ is H, halogen, CN, $(C_1-C_6)$alkyl, $(C_3-C_8)$cycloalkyl, $(C_1-C_2)$alkylene-R';
$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, $NH_2$, NH—R', NH—C(O)—$(C_1-C_6)$alkyl, or $C(O)N[(C_1-C_6)$alkyl$]_2$;
$R_6$ and $R_6'$ are independently of each other H, $(C_3-C_8)$cycloalkyl, $(C_1-C_8)$alkyl, or $(C_1-C_3)$alkylene-R';
$R_7$ and $R_8$ are independently of each other H, halogen, CN, $NO_2$, $(C_1-C_6)$alkyl, $(C_2-C_6)$alkenyl, R', $(C_2-C_3)$alkenylene-$(C_6-C_{10})$aryl, $(C_1-C_3)$alkylene-R', NH—R', NH—$SO_2$—$(C_1-C_6)$alkyl, or $SO_2$—$NH_2$;
$R_9$ is halogen or $(C_1-C_6)$alkyl;
n is 0 or 1; and
L is O or O-methylene;
wherein $R_1$, $R_2$, R', R", Rx and Ry are as defined above;
or their pharmaceutically acceptable salts and/or stereoisomeric forms and/or physiologically functional derivatives.

A most preferred embodiment of the present invention is a compound of the formulae (I), (I'), (II) or (II') wherein
$R_3$ is H, halogen, CN, $(C_1-C_6)$alkyl, $(C_1-C_2)$alkylene-R' or NHR";
$R_4$ is H, halogen, CN, $(C_1-C_4)$alkyl, $(C_3-C_6)$cycloalkyl, $(C_1-C_2)$alkylene-R';
$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, NH—R';
$R_6$ is H, $(C_3-C_6)$cycloalkyl or $(C_1-C_4)$alkyl;
$R_6'$ is H, $(C_3-C_8)$cycloalkyl, $(C_1-C_8)$alkyl, or $(C_1-C_3)$alkylene-R';
$R_7$ and $R_8$ are independently of each other H, halogen, CN, $NO_2$, $(C_1-C_6)$alkyl, $(C_2-C_6)$alkenyl, R', $(C_2-C_3)$alkenylene-$(C_6-C_{10})$aryl, $(C_1-C_3)$alkylene-R', NH—$SO_2$—$(C_1-C_6)$alkyl, or $SO_2$—$NH_2$;
$R_9$ is halogen or $(C_1-C_4)$alkyl;
n is 0; and
L is O;
wherein $R_1$, $R_2$, R', R", Rx and Ry are as defined above;
or their pharmaceutically acceptable salts and/or stereoisomeric forms and/or physiologically functional derivatives.

In another most preferred embodiment of the present invention is a compound of the formulae (I), (I'), (II) or (II') wherein
$R_3$ is H, halogen, $(C_1-C_6)$alkyl;
$R_4$ is H, halogen, $(C_1-C_4)$alkyl;
$R_5$ is H, halogen, $(C_1-C_6)$alkyl;
$R_6$ is H, $(C_3-C_8)$cycloalkyl, or $(C_1-C_8)$alkyl;
$R_6'$ is H, $(C_3-C_8)$cycloalkyl, $(C_1-C_8)$alkyl, or $(C_1-C_3)$alkylene-R';
$R_7$ and $R_8$ are independently of each other H, halogen, CN, $(C_1-C_6)$alkyl or $SO_2$—$NH_2$;
$R_9$ is halogen or $(C_1-C_4)$alkyl;
n is 0; and
L is O;
wherein $R_1$, $R_2$, and R' are as defined above;
or their pharmaceutically acceptable salts and/or stereoisomeric forms and/or physiologically functional derivatives.

As in any embodiment of the invention, in the preceding embodiments which contain preferred, more preferred, most preferred or exemplary definitions of compounds according to the invention, one or more or all of the groups can have any of its preferred, more preferred, most preferred definitions specified above or any one or some of the specific denotations which are comprised by its definitions and are specified above.

Physiologically acceptable salts of compounds of the formulae (I) and (I') mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of physiologically acceptable salts from compounds of the formulae (I) and (I') which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formulae (I) or (I') have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid.

Salts with a physiologically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formulae (I) or (I') of the invention, for example an N-oxide, which on administration to a mammal such as, for example, a human is able to form (directly or indirectly) a compound of the formula (I) or (I') or an active metabolite thereof.

Physiologically functional derivatives include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The invention relates to a compound of the formula (I) or (I') in the form of their racemates, racemic mixtures and pure enantiomers and to their diastereomers and mixtures thereof.

If radicals or substituents may occur more than once in the compounds of the formulae (I) or (I'), they may all, independently of one another, have the stated meaning and be identical or different.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula (I)" or to "compound(s) of formula (I')" hereinafter refer to compound(s) of the formulae (I) or (I') as described above, and their physiologically acceptable salts, solvates and physiologically functional derivatives as described herein.

The term alkyl and the corresposnding alkylene substituents are understood as a hydrocarbon residue which can be linear, i.e. straight-chain, or branched and has 1, 2, 3, 4, 5 or 6 carbon atoms, respectively, where applicable. This also applies if an alkyl group occurs as a substituent on another group, for example in an alkoxy group (O-alkyl), S-alkyl or a —O($C_1$-$C_6$)alkylene-O—, an alkoxycarbonyl group or an arylalkyl group. Examples of alkyl groups are methyl, ethyl, propyl, butyl, pentyl or hexyl, the n-isomers of all these groups, isopropyl, isobutyl, 1-methylbutyl, isopentyl, neopentyl, 2,2-dimethylbutyl, 2-methylpentyl, 3-methylpentyl, isohexyl, sec-butyl, tert-butyl or tert-pentyl. Alkyl groups may—if not otherwise stated—be halogenated once or more, e.g. alkyl groups may be fluorinated, e.g. perfluorinated. Examples of halogenated alkyl groups are $CF_3$ and $CH_2CF_3$, $OCF_3$, $SCF_3$, or —O—$(CF_2)_2$—O—.

Alkenyl are, for example, vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

Alkynyl are, for example, ethynyl, 1-propynyl, 2-propynyl (=propargyl) or 2-butynyl.

Halogen means fluoro, chloro, bromo or iodo.

($C_3$-$C_8$)cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bonds (unsaturated cycloalkyl groups) like, for example, cyclopentenyl or cyclohexenyl can be bound via any carbon atom.

A ($C_6$-$C_{10}$)aryl group means an aromatic ring or a ring system which comprises two aromatic rings which are fused or otherwise linked, for example a phenyl, naphthyl, biphenyl, tetrahydronaphthyl, alpha- or beta-tetralon-, indanyl- or indan-1-on-yl group. A preferred ($C_6$-$C_{10}$)aryl group is phenyl.

A ($C_5$-$C_{10}$)heterocyclyl group means a mono- or bicyclic ring system which comprises, apart from carbon, one or more heteroatoms such as, for example, e.g. 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position. ($C_5$-$C_{10}$)heterocyclyl groups may be (1) aromatic [=heteroaryl groups] or (2) saturated or (3) mixed aromatic/saturated.

Suitable ($C_5$-$C_{10}$)heterocyclyl groups include acridinyl, azocinyl, benzimidazolyl, benzofuryl, benzomorpholinyl, benzothienyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, furanyl, quinazolinyl, quinolinyl, 4H-quinolizinyl, quinoxalinyl, quinuclidinyl, chromanyl, chromenyl, chromen-2-onyl, cinnolinyl, decahydroquinolinyl, 2H,6H-1,5,2-dithiazinyl, dihydrofuro[2,3-b]-tetrahydrofuran, furyl, furazanyl, homomorpholinyl, homopiperazinyl, imidazolidinyl, imidazolinyl, imidazolyi, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, prolinyl, pteridinyl, purynyl, pyranyl, pyrazinyl, pyroazolidinyl, pyrazolinyl, pyrazolyl, pyridazinyl, pyridonyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl. Pyridyl stands both for 2-, 3- and 4-pyridyl. Thienyl stands both for 2- and 3-thienyl. Furyl stands both for 2- and 3-furyl. Also included are the corresponding N-oxides of these compounds, for example, 1-oxy-2-, 3- or 4-pyridyl.

Substitutions in ($C_5$-$C_{10}$)heterocyclyl residues can occur on free carbon atoms or on nitrogen atoms.

Preferred examples of ($C_5$-$C_1$)heterocyclyl residues are pyrazinyl, pyridyl, pyrimidinyl, pyrazolyl, morpholinyl, pyrrolidinyl, piperazinyl, piperidinyl, thienyl, benzofuryl, quinolinyl, tetrazolyl and triazolyl.

($C_6$-$C_{10}$)aryl and ($C_5$-$C_{10}$)heterocyclyl groups are unsubstituted or, if not otherwise stated, substituted one or more times by suitable groups independently selected from halogen, $CF_3$, $NO_2$, $N_3$, CN, C(O)—($C_1$-$C_6$)alkyl, C(O)—($C_1$-$C_6$)aryl, COOH, COO($C_1$-$C_6$)alkyl, $CONH_2$, CONH($C_1$-$C_6$)alkyl, CON[($C_1$-$C_6$)alkyl]$_2$, ($C_3$-$C_8$)cycloalkyl, ($C_1$-$C_6$)alkyl, ($C_1$-$C_6$)alkylene-OH, ($C_1$-$C_6$)alkylene-$NH_2$, ($C_1$-$C_6$)alkylene-NH($C_1$-$C_6$)alkyl, ($C_1$-$C_6$)alkylene-N[($C_1$-$C_6$)alkyl]$_2$, ($C_2$-$C_6$)alkenyl, ($C_2$-$C_6$)alkynyl, O—($C_1$-$C_6$)alkyl, O—C(O)—($C_1$-$C_6$)alkyl, O—C(O)—($C_6$-$C_{10}$)aryl, O—C(O)—($C_5$-$C_{10}$)heterocyclyl, $PO_3H_2$, $SO_3H$, $SO_2$—$NH_2$, $SO_2NH$($C_1$-$C_6$)alkyl, $SO_2N$[($C_1$-$C_6$)alkyl]2, S—($C_1$-$C_6$)alkyl; S—($C_1$-$C_6$)alkylene-($C_6$-$C_{10}$)aryl, S—($C_1$-$C_6$)alkylene-($C_5$-$C_{10}$)heterocyclyl, SO—($C_1$-$C_6$)alkyl, SO—

($C_1$-$C_6$)alkylene-($C_6$-$C_{10}$)aryl, SO—($C_1$-$C_6$)alkylene-($C_5$-$C_{10}$)heterocyclyl, $SO_2$—($C_1$-$C_6$)alkyl, $SO_2$—($C_1$-$C_6$)alkylene-($C_6$-$C_{10}$)aryl, $SO_2$—($C_1$-$C_6$)alkylene-($C_5$-$C_{10}$)heterocyclyl, $SO_2$—NH($C_1$-$C_6$)alkylene-($C_6$-$C_{10}$)aryl, $SO_2$—NH($C_1$-$C_6$)alkylene-($C_5$-$C_{10}$)heterocyclyl, $SO_2$—N[($C_1$-$C_6$)alkyl][($C_1$-$C_6$)alkylene-($C_6$-$C_{10}$)aryl], $SO_2$—N[($C_1$-$C_6$)alkyl][($C_1$-$C_6$)alkylene-($C_6$-$C_{10}$)heterocyclyl], $SO_2$—N[($C_1$-$C_6$)alkylene-($C_6$-$C_{10}$)aryl]$_2$, $SO_2$—N[($C_1$-$C_6$)alkylene-($C_5$-$C_{10}$)heterocyclyl]$_2$, C(NH)(NH$_2$), NH$_2$, NH—($C_1$-$C_6$)alkyl, N[($C_1$-$C_6$)alkyl]$_2$, NH—C(O)—($C_1$-$C_6$)alkyl, NH—C(O)O—($C_1$-$C_6$)alkyl, NH—C(O)—($C_6$-$C_{10}$)aryl, NH—C(O)—($C_5$-$C_{10}$)heterocyclyl, NH—C(O)O—($C_6$-$C_{10}$)aryl, NH—C(O)O—($C_5$-$C_{10}$)heterocyclyl, NH—C(O)—NH—($C_1$-$C_6$)alkyl, NH—C(O)—NH—($C_6$-$C_{10}$)aryl, NH—C(O)—NH—($C_5$-$C_{10}$)heterocyclyl, NH—$SO_2$—($C_1$-$C_6$)alkyl, NH—$SO_2$—($C_6$-$C_{10}$)aryl, NH—$SO_2$—($C_5$-$C_{10}$)heterocyclyl, N($C_1$-$C_6$)alkyl-C(O)—($C_1$-$C_6$)alkyl, N($C_1$-$C_6$)alkyl-C(O)O—($C_1$-$C_6$)alkyl, N($C_1$-$C_6$)alkyl-C(O)—($C_6$-$C_{11}$)aryl, N($C_1$-$C_6$)alkyl-C(O)-heterocyclyl, N($C_1$-$C_6$)alkyl-C(O)O—($C_6$-$C_{10}$)aryl, N($C_1$-$C_6$)alkyl-C(O)O—($C_5$-$C_{10}$)heterocyclyl, N($C_1$-$C_6$)alkyl-C(O)—NH—($C_1$-$C_6$)alkyl], N($C_1$-$C_6$)alkyl-C(O)—NH—($C_6$-$C_{10}$)aryl, N($C_1$-$C_6$)alkyl-C(O)—NH—($C_5$-$C_{10}$)heterocyclyl, N[($C_1$-$C_6$)alkyl]-C(O)—N[($C_1$-$C_6$)alkyl]$_2$, N[($C_1$-$C_6$)alkyl]-C(O)—N[($C_1$-$C_6$)alkyl]-($C_6$-$C_{10}$)aryl, N[($C_1$-$C_6$)alkyl]-C(O)—N[($C_1$-$C_6$)alkyl]-($C_5$-$C_{10}$)heterocyclyl, N[($C_1$-$C_6$)alkyl]-C(O)—N[($C_6$-$C_{10}$)aryl]$_2$, N[($C_1$-$C_6$)alkyl]-C(O)—N[($C_5$-$C_{10}$)heterocyclyl]$_2$, N[($C_6$-$C_{10}$)aryl]-C(O)—($C_1$-$C_6$)alkyl, N[($C_5$-$C_{10}$)heterocyclyl]-C(O)—($C_1$-$C_6$)alkyl, N[($C_6$-$C_{10}$)aryl]-C(O)O—($C_1$-$C_6$)alkyl, N[($C_5$-$C_{10}$)heterocyclyl]-C(O)O—($C_1$-$C_6$)alkyl, N(aryl)-C(O)—($C_6$-$C_{10}$)aryl, N[($C_5$-$C_{10}$)heterocyclyl]-C(O)—($C_6$-$C_{10}$)aryl, N[($C_6$-$C_{10}$)aryl]-C(O)O—($C_6$-$C_{10}$)aryl, N[($C_5$-$C_{10}$)heterocyclyl]-C(O)O—($C_6$-$C_{10}$)aryl, N[($C_6$-$C_{10}$)aryl]-C(O)—NH—($C_1$-$C_6$)alkyl, N[($C_5$-$C_{10}$)heterocyclyl]-C(O)—NH—($C_1$-$C_6$)alkyl, N(aryl)-C(O)—NH—($C_6$-$C_{10}$)aryl, N[($C_5$-$C_{10}$)heterocyclyl]-C(O)—NH—($C_6$-$C_{10}$)aryl, N[($C_6$-$C_{10}$)aryl]-C(O)—N[($C_1$-$C_6$)alkyl]$_2$, N[($C_5$-$C_{10}$)heterocyclyl]-C(O)—N[($C_1$-$C_6$)alkyl]$_2$, N[($C_6$-$C_{10}$)aryl]-C(O)—N[($C_1$-$C_6$)alkyl]-($C_6$-$C_{10}$)aryl, N[($C_5$-$C_{10}$)heterocyclyl]-C(O)—N[($C_1$-$C_6$)alkyl]-($C_6$-$C_{10}$)aryl, N[($C_6$-$C_{10}$)aryl]-C(O)—N[($C_6$-$C_{10}$)aryl]$_2$, N[($C_5$-$C_{10}$)heterocyclyl]-C(O)—N[($C_6$-$C_{10}$)aryl]$_2$, ($C_6$-$C_{10}$)aryl, ($C_1$-$C_6$)alkylene-($C_6$-$C_{10}$)aryl, O—($C_1$-$C_6$)alkylene-($C_6$-$C_{10}$)aryl, ($C_5$-$C_{10}$)heterocyclyl, ($C_1$-$C_6$)alkylene-($C_5$-$C_{10}$)heterocyclyl, O—($C_1$-$C_6$)alkylene-($C_5$-$C_{10}$)heterocyclyl, wherein the ($C_6$-$C_{10}$)aryl or ($C_5$-$C_{10}$)heterocyclyl may be substituted one to 3 times by halogen, OH, $NO_2$, CN, O—($C_1$-$C_6$)alkyl, ($C_1$-$C_6$)alkyl, $NH_2$, NH($C_1$-$C_6$)alkyl, N[($C_1$-$C_6$)alkyl]$_2$, $SO_2CH_3$, COOH, C(O)O—($C_1$-$C_6$)alkyl, $CONH_2$, ($C_1$-$C_6$)alkylene-O—($C_1$-$C_6$)alkyl, ($C_1$-$C_6$)alkylene-O—($C_6$-$C_{10}$)aryl, O—($C_1$-$C_6$)alkylene-($C_6$-$C_{10}$)aryl; or wherein ($C_6$-$C_{10}$)aryl is vicinally substituted by a O—($C_1$-$C_4$)alkylene-O group whereby a 5-8-membered ring is formed together with the carbon atoms the oxygen atoms are attached to Aryl or heterocyclyl substituents of ($C_6$-$C_1$)aryl and ($C_5$-$C_{10}$)heterocyclyl groups may not be further substituted by an aryl or heterocyclyl containing group.

If substituted, preferred substituents for ($C_6$-$C_{10}$)aryl groups are ($C_1$-$C_4$)alkyl, O—($C_1$-$C_4$)alkyl, O-phenyl, C(O)O—($C_1$-$C_6$)alkyl, C(O)OH, C(O)—($C_1$-$C_4$)alkyl, halogen, $NO_2$, $SO_2NH_2$, CN, $SO_2$—($C_1$-$C_4$)alkyl, NH—$SO_2$—($C_1$-$C_4$)alkyl, $NH_2$, NH—C(O)—($C_1$-$C_4$)alkyl, ($C_3$-$C_8$)cycloalkyl, ($C_1$-$C_4$)alkyl-OH, C(O)N[($C_1$-$C_4$)alkyl]$_2$, C(O)$NH_2$, N[($C_1$-$C_4$)alkyl]$_2$, ($C_1$-$C_4$)alkenylene-($C_6$-$C_{10}$)aryl, wherein the ($C_6$-$C_{10}$)aryl may be further substituted by ($C_1$-$C_4$)alkyl, ($C_1$-$C_4$)alkylene-O—($C_1$-$C_6$)alkyl, O—($C_1$-$C_6$)alkyl-($C_6$-$C_{10}$)aryl, or may be vicinally substituted by a O—($C_1$-$C_4$)alkylene-O group whereby a 5-8-membered ring is formed together with the carbon atoms the oxygen atoms are attached to. More preferred substituents for ($C_1$-$C_6$)alkylene-($C_6$-$C_{10}$)aryl are halogen, ($C_1$-$C_4$)alkyl especially $CH_3$ or $CF_3$, O—($C_1$-$C_4$)alkyl especially O—$CH_3$, or $SO_2$—($C_1$-$C_4$)alkyl especially $SO_2$—$CH_3$ or $SO_2$—$CF_3$.

In monosubstituted phenyl groups the substituent can be located in the 2-position, the 3-position or the 4-position, with the 3-position and the 4-position being preferred. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position.

The above statements relating to phenyl groups correspondingly apply to divalent groups derived from phenyl groups, i.e. phenylene which can be unsubstituted or substituted 1,2-phenylene, 1,3-phenylene or 1,4-phenylene. The above statements also correspondingly apply to the aryl subgroup in arylalkylene groups. Examples of arylalkylene groups which can also be unsubstituted or substituted in the aryl subgroup as well as in the alkylene subgroup, are benzyl, 1-phenylethylene, 2-phenylethylene, 3-phenylpropylene, 4-phenylbutylene, 1-methyl-3-phenyl-propylene.

If substituted, preferred substituents for ($C_5$-$C_{10}$)heterocyclyl groups are ($C_1$-$C_4$)alkyl, O—($C_1$-$C_4$)alkyl, ($C_1$-$C_4$)alkylene-phenyl, halogen, ($C_1$-$C_4$)alkylene-O—($C_1$-$C_4$)alkyl, ($C_5$-$C_{10}$)heterocyclyl, ($C_1$-$C_4$)alkylene-N[($C_1$-$C_4$)alkyl]$_2$, or ($C_6$-$C_{10}$)aryl, wherein the ($C_6$-$C_{10}$)aryl may be further substituted by ($C_1$-$C_4$)alkyl, ($C_1$-$C_4$)alkylene-O—($C_1$-$C_6$)alkyl, O—($C_1$-$C_6$)alkyl-($C_6$-$C_{10}$)aryl, or may be vicinally substituted by a O—($C_1$-$C_4$)alkylene-O group whereby a 5-8-membered ring is formed together with the carbon atoms the oxygen atoms are attached to. More preferred substituents for ($C_5$-$C_{10}$)heterocyclyl groups are ($C_1$-$C_4$)alkyl or halogen.

The general and preferred substituents of ($C_6$-$C_{10}$)aryl and ($C_5$-$C_{10}$)heterocyclyl groups may be combined with the general and preferred definitions of $R_1$, $R_2$, $R_3$, $R_4$, $R_5$, $R_6$, $R_6'$, $R_7$, $R_8$, $R_9$, n and L as described above.

The present invention therefore also relates to the compounds of the formulae (I) or (I') and/or their physiologically acceptable salts and/or stereoisomeric forms for use as pharmaceuticals (or medicaments), to the use of the compounds of the formulae (I) or (I') and/or their physiologically acceptable salts and/or stereoisomeric forms for the production of pharmaceuticals for the treatment and/or prevention of diseases associated with Rho-kinase and/or Rho-kinase mediated phosphorylation of myosin light chain phosphatase, i.e. for the treatment and/or prevention of hypertension, pulmonary hypertension, ocular hypertension, retinopathy, and glaucoma, peripheral circulatory disorder, peripheral occlusive arterial disease (PAOD), coronary heart disease, angina pectoris, heart hypertrophy, heart failure, ischemic diseases, ischemic organ failure (end organ damage), fibroid lung, fibroid liver, liver failure, nephropathy, including hypertension-induced, non-hypertension-induced, and diabetic nephropathies, renal failure, fibroid kidney, renal glomerulosclerosis, organ hypertrophy, asthma, chronic obstructive pulmonary disease (COPD), adult respiratory distress syndrome, thrombotic disorders, stroke, cerebral vasospasm, cerebral ischemia, pain, e.g. neuropathic pain, neuronal degeneration, spinal cord injury, Alzheimer's disease, premature birth, erectile dysfunction, endocrine dysfunctions, arteriosclerosis, prostatic hypertrophy, diabetes and complications of diabetes, metabolic syndrome, blood vessel restenosis, atherosclerosis, inflammation, autoimmune diseases, AIDS, osteopathy such as osteoporosis, infection of digestive tracts with bacteria, sepsis, cancer development and progression, e.g. cancers of the breast, colon, prostate, ovaries, brain and lung and their metastases.

The treatment and/or prevention of diseases in humans is a preferred embodiment but also warm blooded animals such as cats, dogs, rats, horses etc. may be treated with the compounds of the present invention.

The present invention furthermore relates to pharmaceutical preparations (or pharmaceutical compositions) which contain an effective amount of at least one compound of the formula (I) or (I') and/or its physiologically acceptable salts and/or stereoisomeric forms and a pharmaceutically acceptable carrier, i.e. one or more pharmaceutically acceptable carrier substances (or vehicles) and/or additives (or excipients).

Optionally the physiologically functional derivatives, including the prodrugs, of a compound of the formula (I) or (I') may be utilized in the above mentioned uses and pharmaceutical preparations.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formulae (I) or (I') and/or its (their) physiologically acceptable salts and/or its (their) stereoisomeric forms as well as its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of a compound of the formula (I) or (I') and/or their physiologically acceptable salts and/or their stereoisomeric forms. The amount of the active ingredient of the formula (I) or (I') and/or its physiologically acceptable salts and/or its stereoisomeric forms in the pharmaceutical preparations normally is from about 0.5 to about 1000 mg, preferably from about 1 to about 500 mg.

In addition to the active ingredients of the formula (I) or (I') and/or their physiologically acceptable salts and/or stereoisomeric forms and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae (I) and/or (I') and/or their physiologically acceptable salts and/or their prodrugs. In case a pharmaceutical preparation contains two or more compounds of the formulae (I) and/or (I'), the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae (I) or (I') allows a great deal of control over the biological and physico-chemical properties of the compounds and thus allows the selection of such desired compounds. Furthermore, in addition to at least one compound of the formula (I) or (I') and/or its physiologically acceptable salts and/or its stereoisomeric forms, the pharmaceutical preparations can also contain one or more other therapeutically or prophylactically active ingredients.

When using the compounds of the formulae (I) or (I') the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formulae (I) or (I') can be used as synthesis intermediates for the preparation of other compounds, in particular of other pharmaceutical active ingredients, which are obtainable from the compounds of the formula I, for example by introduction of substituents or modification of functional groups.

It is understood that modifications that do not substantially affect the activity of the various embodiments of this invention are included within the invention disclosed herein.

The compounds of the formulae (I) or (I') can be prepared according to the following exemplified compounds without limiting the scope of the claims.

In general, protective groups that may still be present in the products obtained in the coupling reaction are then removed by standard procedures. For example, tert-butyl protecting groups, in particular a tert-butoxycarbonyl group which is a protection form of an amino group, can be deprotected, i.e. converted into the amino group, by treatment with trifluoroacetic acid. As already explained, after the coupling reaction also functional groups can be generated from suitable precursor groups. In addition, a conversion into a physiologically acceptable salt or a prodrug of a compound of the formulae (I) or (I') can then be carried out by known processes.

In general, a reaction mixture containing a final compound of the formula (I) or (I') or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as amino acid sequence analysis, NMR, IR and mass spectrometry (MS) can be used for characterizing a compound of the invention.

Isoquinolinones can by synthesized via a variety of methods. The following general schemes illustrate some of the possible ways to access isoquinolones, but do not limit the present invention.

Scheme 1:

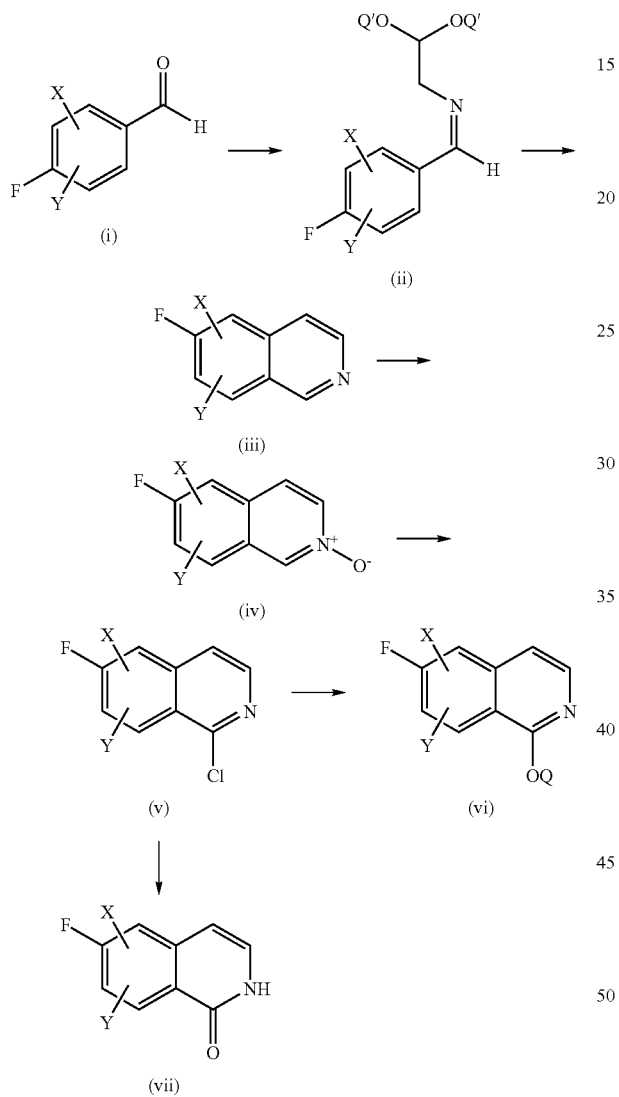

A suitably substituted aldehyde, for example substituted by X or Y being independently from each other hydrogen, alkyl, alkoxy or halide attached in a suitable position, can be reacted with a suitable compound such as for example an actal of aminoacetaldehyde for example in a solvent like THF, chloroform or toluene under acid catalysis by toluene sulfonic acid or another appropriate acid to give imine (ii) wherein Q' can be for instance methyl or ethyl, which in turn can be cyclized by different methods to the isoquinoline (iii). For example this can be done by Lewis acid catalysis by suitable Lewis acids like titanium tetrachloride, ferrous halides, aluminium halides etc. at temperatures ranging from ambient to 100° C. or by reducing the imine to the corresponding amine by action of a suitable reducing agent like sodium borohydride, converting the amine into an amide or sulphonamide by reaction with a suitable acid chloride and subsequent cyclization to the isoquinoline by action of an appropriate lewis acid. The isoquinoline (iii) itself can then be converted to the corresponding N-oxide (iv) by action of a suitable oxidative agent like hydrogen peroxide, m-chloro perbenzoic acid or others at room temperature or elevated temperature. The N-oxide (iv) can then be converted into the 1-chloro-isoquinoline derivative (v) by reacting it with a reagent like phosphorous oxy chloride in or without presence of phosphorous pentachloride. The derivative (v) can then be turned into suitable 1-alkoxy-derivatives by reacting it with various alcohols Q-OH like methanol, ethanol or benzyl alcohol in the presence of a suitable base like sodium hydride and in a suitable solvent like dimethyl formamide, dimethyl acetamide or others. Alternatively (v) can be directly converted into the isoquinolinone derivative (vii) by reacting it with a reagent like ammonium acetate.

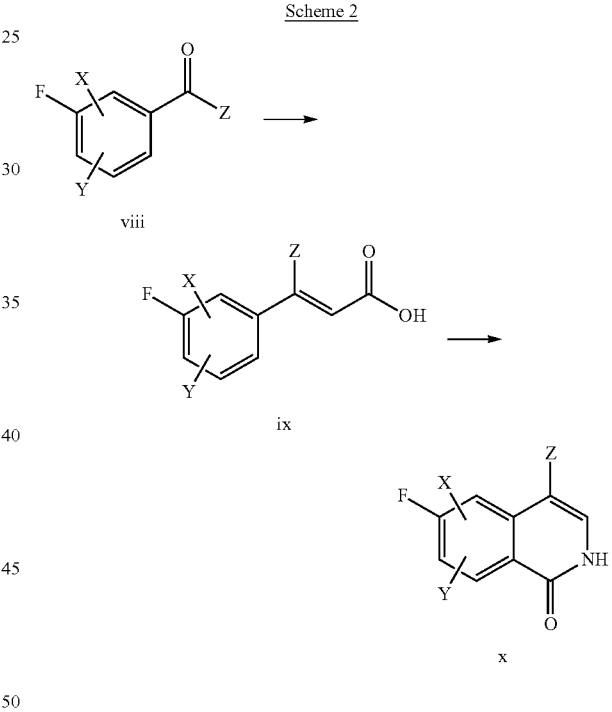

Alternatively isoquinolines can be obtained by reacting suitable 3-formylated or acylated fluorobenzenes (viii), wherein z is for example H or alkyl like methyl or ethyl, with a reagent like triethyl phosphono acetate in the presence of a suitable base like sodium hydride to give the corresponding cinnamic acid ester, which subsequently is cleaved by action of a suitable base like potassium hydroxide, sodium hydroxide or lithium hydroxide in a suitable solvent to deliver acid (ix). (ix) can then be converted in the corresponding acid chloride by well known methods, which can be transferred into the acid azide by reaction with sodium azide in a suitable solvent like ether, chloroform or acetone in or without the presence of water. The corresponding azide then can be converted into isoquinolinone (x) by reacting it in a suitable solvent like diphenylmethane or dipenylether at suitable temperature.

Scheme 3:

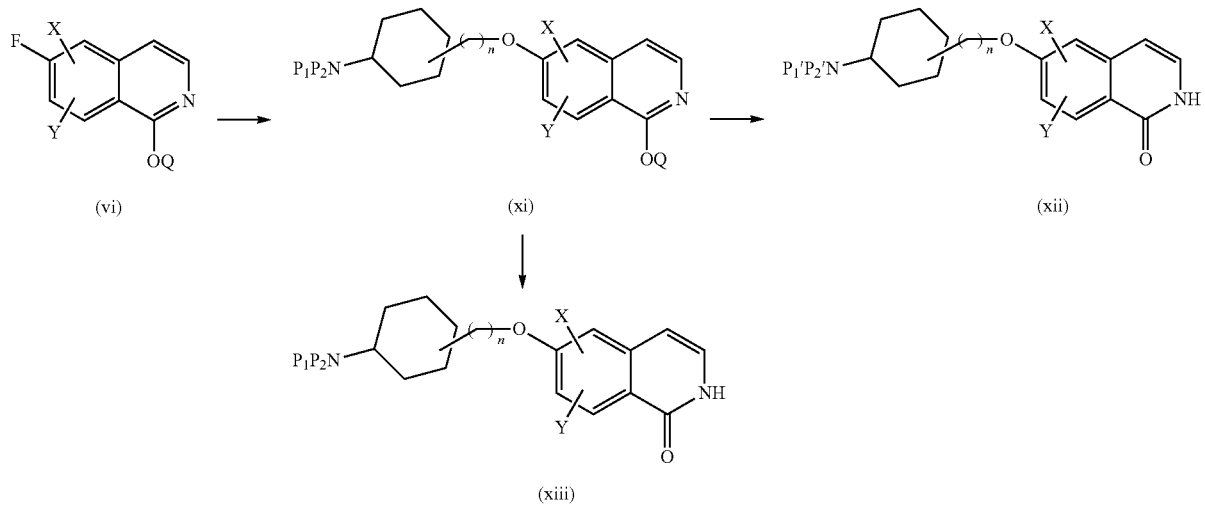

The above obtained 6-Fluoro-isoquinolones, for example (vi), can be reacted with suitable $P_1/P_2$ substituted amino alcohols wherein $P_1/P_2$ are independently from each other for example hydrogen, alkyl or a protecting group like for example Boc or phthaloyl in the presence of base such as DBU, cesium carbonate or sodium hydride to give the corresponding alkoxy substituted derivatives (xi). Eventually, this conversion can already by performed at earlier stages of the synthesis (e.g. by reacting a suitable intermediate). It is understood, that this may require in case of unprotected isoquinolones protection on the nitrogen or oxygen of the isoquinolone moiety by suitable methods, like reaction with suitably substituted alkyl or benzyl halides in the presence of base.

The products like (xi) obtained via this method can then either be liberated or, if a suitable amino functionality is present, be reacted with suitable aldehydes or ketones in the presence of a reducing agent like sodium triacetoxy borohydride, sodium borohydride or sodium cyanoborohydride in a suitable solvent and in the presence of a water withdrawing agent like molecular sieves or a suitable ortho ester. This amino group may have to be liberated in an initial step like for example acidic removal of Boc-groups.

In case of use of protected isoquinolones, cleavage of the used protection groups is required to liberate the desired isoquinolone (xii). This liberation, however, can be performed before or after the reductive amination step, depending on the nature of the used aldehyde/ketone and the protection group used.

Isoquinolone derivatives like (xii) can be obtained as free bases or as various salts like for example hydrochlorides, hydrobromides, phosphates, trifluoroacetates, sulfates or fumarates. The salts obtained can be converted into the corresponding free base by either subjecting them to ion exchange chromatography or for example by alkaline aqueous treatment and subsequent extraction with suitable organic solvents like for example methyl tert. butyl ether, chloroform, ethyl acetate or isopropanol/dichloromethane mixtures and subsequent evaporation to dryness.

The general methods for the preparation of isoquinolone derivatives as described above can be readily adapted to the preparation of the compounds of the formula (I) or (I'). In the following examples the preparation of the compounds of the present invention is outlined in more detail.

Accordingly, the following examples are part of and intended to illustrate but not to limit the present invention.

(2,2-Dimethoxy-ethyl)-(4-fluoro-benzyl)-amine (1)

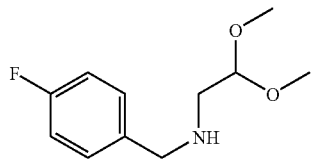

12.4 g of 4-fluorobenzaldehyde were dissolved in 100 mL of toluene and reacted with 10.5 g of 2-aminoacetaldehyde dimethylacetal and 1.90 of p-toluenesulfonic acid monohydrate for two hours at a Dean Stark apparatus. The solution was allowed to cool down, extracted with saturated sodium bicarbonate, water and brine, dried over magnesium sulfate and evaporated to dryness. The crude product was dissolved in 100 mL of ethanol. 1.89 g of sodium borohydride were added portionwise. Stirring was continued overnight. For workup, acetic acid was added until no gas evolution could be observed. Then the solution was evaporated to dryness, taken up in dichloromethane and washed twice with water. The organic layer was extracted with brine, dried over magnesium sulfate and evaporated to dryness. The obtained crude product (20 g) was used for further reactions without purification. $R_t$=0.86 min (Method B). Detected mass: 182.1 (M-OMe$^-$), 214.2 (M+H$^+$).

N-(2,2-Dimethoxy-ethyl)-N-(4-fluoro-benzyl)-4-methyl-benzene-sulfonamide (2)

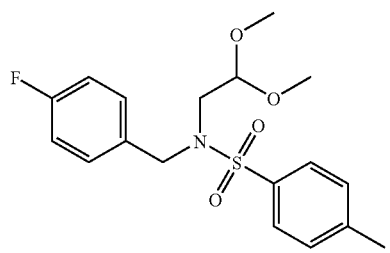 [SMILES: COC(CN(Cc1ccc(F)cc1)S(=O)(=O)c1ccc(C)cc1)OC]

20 g of (2,2-dimethoxy-ethyl)-(4-fluoro-benzyl)-amine (1) were dissolved in 120 ml of dichloromethane. 20 mL of pyridine were added. At 0° C. a solution of 23.8 g p-toluenesulfonic acid chloride in dichloromethane was added dropwise. The reaction was allowed to warm to room temperature and stirring is continued until conversion was completed. For workup, the reaction mixture was extracted twice with 2M hydrochloric acid, twice with sodium bicarbonate and once with brine. The organic layer was dried over magnesium sulfate, evaporated to dryness and the obtained crude product was purified by silica gel chromatography to yield 22.95 g of compound 2 as an orange oil. $R_t$=1.71 min (Method C). Detected mass: 336.1 (M-OMe$^-$).

6-Fluoro-isoquinoline (3)

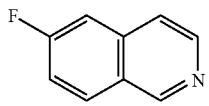

41.6 g of AlCl$_3$ were suspended in 400 mL of dichloromethane. At room temperature, a solution of 22.95 g of N-(2,2-dimethoxy-ethyl)-N-(4-fluoro-benzyl)-4-methyl-benzenesulfonamide (2) in 150 ml of dichloromethane was added. Stirring was continued at room temperature overnight, the solution was poured on ice, the organic layer was separated, the aqueous phase was extracted twice with dichloromethane and the combined organic layers were then extracted twice with sodium bicarbonate. The organic layer was dried over magnesium sulfate, evaporated to dryness and the obtained crude product (8.75 g) is purified by silica gel chromatography to yield 2.74 g of compound (23). $R_t$=0.30 min (Method C). Detected mass: 148.1 (M+H$^+$).

7-Chloro-6-fluoro-isoquinoline (4)

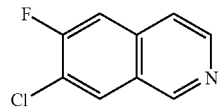

Starting from 3-chloro-4-fluoro-benzaldehyde, the title compound was prepared by the same reaction sequence as used for the synthesis of 6-fluoro-isoquinoline (3). $R_t$=0.77 min (Method A). Detected mass: 182.1/184.1 (M+H$^+$).

7-Bromo-6-fluoro-isoquinoline (92)

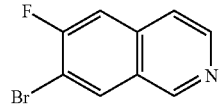 [SMILES: Fc1cc2ccncc2cc1Cl]

Starting from 3-bromo-4-fluoro-benzaldehyde, the title compound was prepared by the same reaction sequence as used for the synthesis of 6-fluoro-isoquinoline (3). $R_t$=0.91 min (Method B). Detected mass: 226.0/228.0 (M+H$^+$).

7-Chloro-6-fluoro-isoquinoline 2-oxide (5)

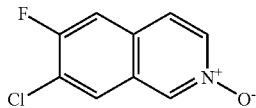

25 g (137.7 mmol) of 7-chloro-6-fluoro-isoquinoline (4) were in dissolved in 500 ml of dichloromethane. At room temperature 50.9 g (206.5 mmol) of m-chloro perbenzoic acid (70%) were added and the mixture was stirred at room temperature until complete conversion is achieved. For workup, the precipitate was filtered off and washed with dichloromethane. The filtrate was washed twice with sodium bicarbonate solution. The layers were separated and the aqueous phase was extracted twice with dichloromethane. The organic phases were dried with magnesium sulfate and evaporated. The so obtained solid material (18.4 g) was used without further purification. $R_t$=0.87 min (Method C). Detected mass: 198.1/200.1 (M+H$^+$).

1,7-Dichloro-6-fluoro-isoquinoline (6)

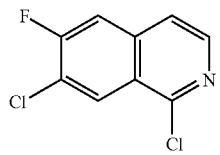 [SMILES: Fc1cc2ccnc(Cl)c2cc1Cl]

2.6 g (12.0 mmol) of 7-chloro-6-fluoro-isoquinoline 2-oxide (5) were heated in 40 ml of POCl$_3$ at reflux for 4 h. After the mixture has cooled down to room temperature, it was poured on ice. The aqueous solution was extracted three times with dichloromethane. The combined organic layers were dried with magnesium sulfate and evaporated to yield 2.91 g of the title compound, which was used without further purification. $R_t$=2.34 min (Method A). Detected mass: 216.0/218.0 (M+H$^+$).

5-Chloro-6-fluoro-isoquinoline (7)

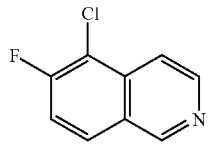 [SMILES: Fc1ccc2cnccc2c1Cl]

7.0 g (38.1 mmol) of 6-fluoroisoquinoline (3) were dissolved in 60 mL of concentrated sulfuric acid. At 0° C. 10.18 g of N-chloro succinimide were added. After 1 h another 5.2 g of N-chloro succiminide were added and the solution was heated to 50° C. Two more portions of 5.2 g N-chloro succinimide were added successively and stirring was continued at 50° C. until the reaction was complete. The reaction mixture was cooled to room temperature, was poured on ice and adjusted to pH 10 by addition of sodium hydroxide. The precipitate was filtered off, dissolved in dichloromethane and washed with aqueous sodium hydroxide. The organic layer was dried over magnesium sulfate, evaporated and the crude product was purified by preparative HPLC to yield 4.04 g of 5-chloro-6-fluoro-isoquinoline (7) as trifluoroacetate. $R_t$=0.97 min (Method A). Detected mass: 182.0/184.0 (M+H$^+$).

5-Chloro-6-fluoro-isoquinoline 2-oxide (8)

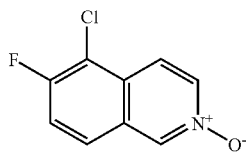 [SMILES: [O-][n+]1ccc2c(Cl)c(F)ccc2c1]

Starting from 5-chloro-6-fluoro-isoquinoline trifluoroacetate (7), the title compound was obtained following the method described for 7-chloro-6-fluoro-isoquinoline 2-oxide (5). $R_t$=0.90 min (Method C). Detected mass: 198.1/200.1 (M+H$^+$).

1,5-Dichloro-6-fluoro-isoquinoline (9)

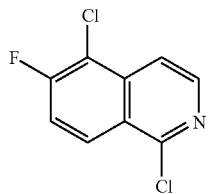

5-Chloro-6-fluoro-isoquinoline 2-oxide (8) was converted to the title compound following the protocol described for the synthesis of 1,7-dichloro-6-fluoro-isoquinoline (6). The crude product was purified by silica gel chromatography (heptane/ethyl acetate 4:1). $R_t$=1.70 min (Method C). Detected mass: 216.0/218.0 (M+H$^+$).

6-(cis-4-Amino-cyclohexyloxy)-7-chloro-2H-isoquinolin-1-one (10)

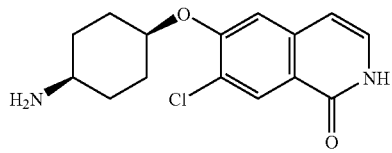 [SMILES: N[C@H]1CC[C@@H](Oc2cc3cc[nH]c(=O)c3cc2Cl)CC1]

2.19 g (10.2 mmol) of cis-(4-hydroxy-cyclohexyl)-carbamic acid tert-butyl ester were dissolved in 20 ml of dimethyl acetamide. Under argon atmosphere, 814 mg (20.4 mmol) of sodium hydride (60%) were added and the mixture was stirred at room temperature. After 30 min, a solution of 2.0 g (9.26 mmol) of 1,7-dichloro-6-fluoro-isoquinoline (6) in 5 ml of dimethyl acetamide was added and stirring was continued at room temperature. After 1 h, 2.0 g (18.5 mmol) of benzyl alcohol and 740 mg (18.5 mmol) of sodium hydride (60%) were added. The reaction was stirred for 2 h at room temperature and 30 minutes at 80° C. to achieve complete conversion. The solvent was removed in vacuo and the residue was taken up in dichloromethane and washed twice with water. After drying over magnesium sulfate, the organic layer was evaporated, to furnish 4.44 g of the crude intermediate cis-[4-(1-benzyloxy-7-chloro-isoquinolin-6-yloxy)-cyclohexyl]-carbamic acid tert-butyl ester. The intermediate was dissolved in methanol and treated with 2 N HCl at room temperature. After stirring for 2 d, the reaction mixture was adjusted to alkaline pH by addition of sodium hydroxide. The solvent was removed in vacuo and the residue was stirred in ethanol. Filtration and evaporation of the filtrate yielded a solid material, which was purified by preparative HPLC. The obtained trifluoroacetate was dissolved in 2 N HCl. Final lyophilization gave 433 mg of the title compound as hydrochloride. $R_t$=0.89 min (Method B). Detected mass: 293.2/295.2 (M+H$^+$).

6-(cis-4-Amino-cyclohexyloxy)-5-chloro-2H-isoquinolin-1-one (11)

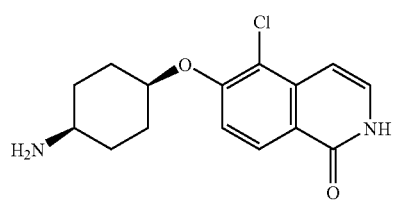 [SMILES: N[C@H]1CC[C@@H](Oc2ccc3c(=O)[nH]ccc3c2Cl)CC1]

Starting from cis-(4-hydroxy-cyclohexyl)-carbamic acid tert-butyl ester and 1,5-dichloro-6-fluoro-isoquinoline (9), the title compound was prepared as hydrochloride following the route described for 6-(cis-4-amino-cyclohexyloxy)-7-chloro-isoquinolin-1-ol hydrochloride (10). $R_t$=1.04 min (Method B). Detected mass: 293.1/295.1 (M+H$^+$).

7-Chloro-6-(cis-4-cyclopropylamino-cyclohexyloxy)-2H-isoquinolin-1-one (12)

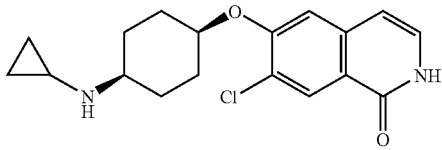 [SMILES: O=c1[nH]ccc2cc(O[C@H]3CC[C@@H](NC4CC4)CC3)c(Cl)cc12]

and

7-Chloro-6-(cis-4-dicyclopropylamino-cyclohexyloxy)-2H-isoquinolin-1-one (13)

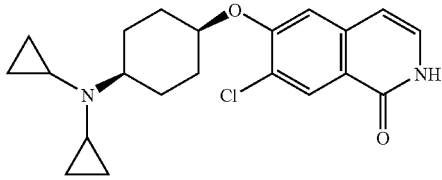 [SMILES: O=c1[nH]ccc2cc(O[C@H]3CC[C@@H](N(C4CC4)C4CC4)CC3)c(Cl)cc12]

100 mg (0.3 mmol) of 6-(cis-4-Amino-cyclohexyloxy)-7-chloro-2H-isoquinolin-1-one hydrochloride (10) were dissolved in 10 ml of methanol. 54.5 mg (0.54 mmol) of triethyl amine were added and the mixture was stirred at room temperature for 10 minutes. Freshly dried molecular sieves, 159.3 mg (2.66 mmol) of acetic acid, 104.6 mg (0.6 mmol) of (1-ethoxy-cyclopropoxy) trimethyl silane and 56.5 mg (0.9 mmol) of sodium cyanoborohydride were added and the reaction mixture was refluxed for 3 h. 5 equivalents of (1-ethoxy-cyclopropoxy)-trimethyl-silane were added, followed by 2 equivalents of sodium cyanoborohydride. The mixture was allowed to stand at room temperature overnight. The mixture was filtered and the filtrate was evaporated. The residue was dissolved in dichloromethane, washed twice with 2 N NaOH and water and dried over magnesium sulfate. After evaporation of the solvent and purification by preparative HPLC 4.5 mg of 7-chloro-6-(cis-4-cyclopropylamino-cyclohexyloxy)-isoquinolin-1-ol (12) as trifluoroacetate and 16 mg of 7-chloro-6-(cis-4-dicyclopropylamino-cyclohexyloxy)-isoquinolin-1-ol (13) as trifluoroacetate were obtained. $R_t$ (12)=1.05 min (Method A). Detected mass: 333.2/335.2 (M+H$^+$). $R_t$ (13)=1.15 min (Method B). Detected mass: 373.1/375.1 (M+H$^+$).

6-(trans-4-Amino-cyclohexyloxy)-7-chloro-isoquinolin-1-ol (14)

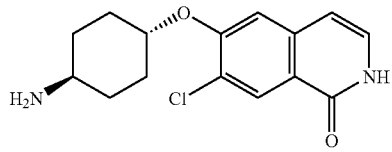 [SMILES: N[C@H]1CC[C@H](Oc2cc3cc[nH]c(=O)c3cc2Cl)CC1]

Starting from trans-(4-hydroxy-cyclohexyl)-carbamic acid tert-butyl ester and 1,7-dichloro-6-fluoro-isoquinoline (6) the title compound was prepared as hydrochloride following the route described for 6-(cis-4-amino-cyclohexyloxy)-7-chloro-isoquinolin-1-ol hydrochloride (10). $R_t$=1.08 min (Method B). Detected mass: 293.2/295.2 (M+H$^+$).

trans-4-(Isoquinolin-6-yloxy)-cyclohexylamine (15)

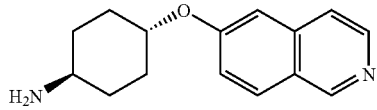 [SMILES: N[C@H]1CC[C@H](Oc2ccc3cnccc3c2)CC1]

6.1 g (53 mmol) of 4-amino-cyclohexanol were dissolved in 50 ml of dimethyl acetamide and 4.24 g (106 mmol) of sodium hydride (60%) were added at room temperature. After the reaction mixture was stirred for 30 minutes under argon, a solution of 6.49 g (35.3 mmol) of 6-fluoro-isoquinoline hydrochloride was added and the mixture was stirred at room temperature overnight. For workup, the solvent was removed in vacuo and the residue was dissolved in dichloromethane and washed twice with water. The organic layer was separated, dried with magnesium sulfate and evaporated to yield 8.64 g of the crude product, which was used without further purification. $R_t$=0.77 min (Method B). Detected mass: 243.1 (M+H$^+$).

trans-N-[4-(Isoquinolin-6-yloxy)-cyclohexyl]-acetamide (16)

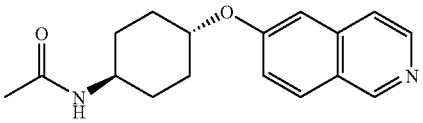 [SMILES: CC(=O)N[C@H]1CC[C@H](Oc2ccc3cnccc3c2)CC1]

8.4 g (34.7 mmol) of 4-(isoquinolin-6-yloxy)-cyclohexylamine (15) were dissolved in 100 ml of dichloromethane/pyridine (4:1). At 0° C. a solution of 3.27 g (41.6 mmol) of acetyl chloride in 10 ml of dichloromethane was added and the reaction mixture was stirred at room temperature. After 2 h, the solution was diluted with dichloromethane and washed twice with saturated sodium bicarbonate solution. After washing twice with 2 N HCl, the product was transferred to the aqueous phase. The HCl-layers were adjusted to alkaline pH by addition of solid NaOH and extracted three times with dichloromethane. Drying the organic layers with magnesium sulfate and evaporation of the solvent gave 7.69 g of the crude product. After silica gel chromatography 4.48 g of the title compound were isolated. $R_t$=0.87 min (Method A). Detected mass: 285.2 (M+H$^+$).

trans-N-[4-(2-Oxy-isoquinolin-6-yloxy)-cyclohexyl]-acetamide (17)

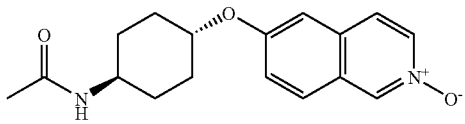 [SMILES: CC(=O)N[C@H]1CC[C@H](Oc2ccc3c[n+]([O-])ccc3c2)CC1]

Starting from N-[4-(isoquinolin-6-yloxy)-cyclohexyl]-acetamide (16) the title compound was obtained following the method described for 7-chloro-6-fluoro-isoquinoline 2-oxide (5). $R_t$=1.01 min (Method A). Detected mass: 301.2 (M+H$^+$).

trans-N-[4-(1-Chloro-isoquinolin-6-yloxy)-cyclohexyl]-acetamide (18)

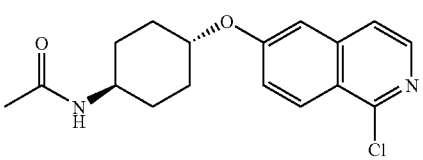 [SMILES: CC(=O)N[C@H]1CC[C@H](Oc2ccc3c(Cl)nccc3c2)CC1]

N-[4-(2-Oxy-isoquinolin-6-yloxy)-cyclohexyl]-acetamide (17) was converted to the title compound following the protocol described for 1,7-dichloro-6-fluoro-isoquinoline (6). The crude product was purified by preparative HPLC. $R_t$=1.49 min (Method B). Detected mass: 319.1/321.1 (M+H$^+$).

trans-N-[4-(1-Benzyloxy-isoquinolin-6-yloxy)-cyclohexyl]-acetamide (19)

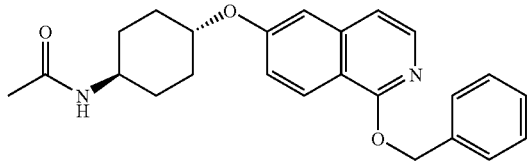 [SMILES: CC(=O)N[C@H]1CC[C@H](Oc2ccc3c(OCc4ccccc4)nccc3c2)CC1]

975 mg (3.06 mmol) of N-[4-(1-chloro-isoquinolin-6-yloxy)-cyclohexyl]-acetamide (18) were dissolved in 20 ml of dimethyl acetamide and 992 mg (9.17 mmol) of benzyl alcohol were added. After addition of 367 mg (9.17 mmol) of sodium hydride (60%), the reaction mixture was stirred for 3 h at room temperature and for 1 h at 80° C. Then, the solvent was removed in vacuo, the residue was dissolved in dichloromethane and washed three times with water. The organic layer was dried with magnesium sulfate and evaporated. Final purification by preparative HPLC yielded 680 mg of the title compound. $R_t$=1.75 min (Method B). Detected mass: 391.2 (M+H$^+$).

trans-6-(4-Amino-cyclohexyloxy)-2H-isoquinolin-1-one (20)

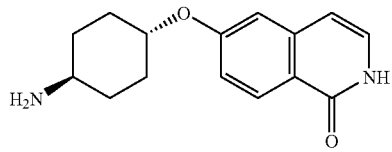 [SMILES: N[C@H]1CC[C@H](Oc2ccc3c(=O)[nH]ccc3c2)CC1]

680 mg (1.74 mmol) of N-[4-(1-benzyloxy-isoquinolin-6-yloxy)-cyclohexyl]-acetamide (19) were heated in 2 N HCl in an autoclave at 120° C. until complete conversion is achieved. The solvent is removed in vacuo and the residue is purified by preparative HPLC. The product fractions were evaporated and dissolved in 2 N HCl. After lyophilisation 182 mg of the title compound could be obtained as hydrochloride. $R_t$=0.97 min (Method B). Detected mass: 259.2 (M+H$^+$).

cis-4-(Isoquinolin-6-yloxy)-cyclohexylamine (21)

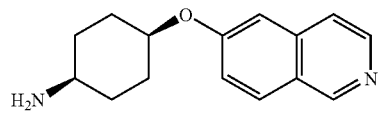 [SMILES: N[C@H]1CC[C@@H](Oc2ccc3cnccc3c2)CC1]

Starting from 6-fluoro-isoquinoline hydrochloride and cis-4-amino-cyclohexanol the title compound was prepared following the protocol described for compound (15). $R_t$=0.64 min (Method B). Detected mass: 243.2 (M+H$^+$).

cis-N-[4-(Isoquinolin-6-yloxy)-cyclohexyl]-acetamide (22)

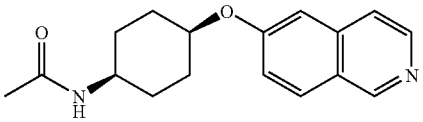 [SMILES: CC(=O)N[C@H]1CC[C@@H](Oc2ccc3cnccc3c2)CC1]

Starting from cis-4-(isoquinolin-6-yloxy)-cyclohexylamine (21) the title compound was prepared following the protocol described for the compound (16). $R_t$=0.90 min (Method B). Detected mass: 285.1 (M+H$^+$).

cis-N-[4-(2-Oxy-isoquinolin-6-yloxy)-cyclohexyl]-acetamide (23)

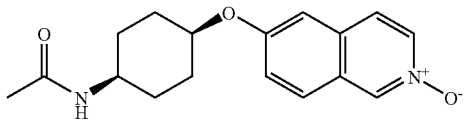 [SMILES: CC(=O)N[C@H]1CC[C@@H](Oc2ccc3c[n+]([O-])ccc3c2)CC1]

Starting from cis-N-[4-(isoquinolin-6-yloxy)-cyclohexyl]-acetamide (22) the title compound was obtained following the method described for 7-chloro-6-fluoro-isoquinoline 2-oxide (5). $R_t$=0.80 min (Method C). Detected mass: 301.2 (M+H$^+$).

cis-4-(2-Oxy-isoquinolin-6-yloxy)-cyclohexylamine (24)

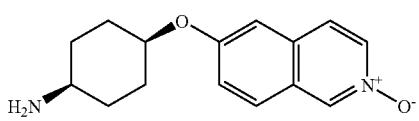 [SMILES: N[C@H]1CC[C@@H](Oc2ccc3c[n+]([O-])ccc3c2)CC1]

2.43 g (8.1 mmol) of cis-N-[4-(2-oxy-isoquinolin-6-yloxy)-cyclohexyl]-acetamide (23) were refluxed in 50 ml of 2 N HCl for 16 h. Evaporation of the solvent gave 2.46 g of the title compound (crude product) as HCl-salt. $R_t$=0.59 min (Method C). Detected mass: 517.3; 259.2; 130.2 [(2M+H$^+$), (M+H$^+$), ½ (M+H$^+$)].

cis-4-(1-Chloro-isoquinolin-6-yloxy)-cyclohexylamine (25)

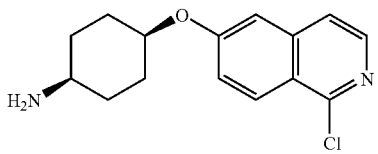 [SMILES: N[C@H]1CC[C@@H](Oc2ccc3c(Cl)nccc3c2)CC1]

2.46 g of cis-4-(2-oxy-isoquinolin-6-yloxy)-cyclohexylamine (24, crude product) were heated to 100° C. in 20 ml POCl$_3$. After 1 h the mixture is cooled to room temperature and poured on ice. The aqueous solution is brought to an alkaline pH by addition of sodium hydroxide and extracted three times with dichloromethane. The combined organic layers were dried with magnesium sulfate and the solvent was removed under reduced pressure to yield 1.14 g of the title compound as crude product, which was used without further purification. R$_t$=0.90 min (Method C). Detected mass: 277.1/279.2 (M+H$^+$).

cis-[4-(1-Chloro-isoquinolin-6-yloxy)-cyclohexyl]-carbamic acid tert-butylester (26)

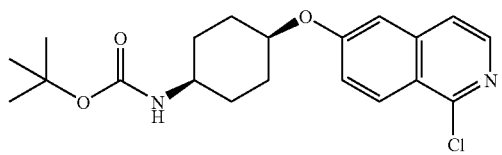 [SMILES: CC(C)(C)OC(=O)N[C@H]1CC[C@@H](Oc2ccc3c(Cl)nccc3c2)CC1]

1.14 g of cis-4-(1-chloo-isoquinolin-6-yloxy)-cyclohexylamine (25, crude product) was dissolved in 20 ml of dichloromethane. At 0° C. a solution of 1.17 g (5.35 mmol) of di-tert-butyl dicarbonate in 5 ml of dichloromethane was added and the solution was stirred at room temperature. After 1 h, the solution was washed with water, dried and evaporated, to yield 1.65 g of the title compound, which was used without further purification. R$_t$=1.77 min (Method C). Detected mass: 377.1/379.1 (M+H$^+$).

cis-[4-(1-Benzyloxy-isoquinolin-6-yloxy)-cyclohexyl]-carbamic acid tert-butyl ester (27)

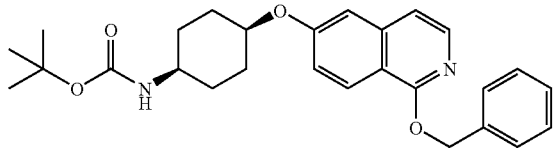 [SMILES: CC(C)(C)OC(=O)N[C@H]1CC[C@@H](Oc2ccc3c(OCc4ccccc4)nccc3c2)CC1]

Starting from cis-[4-(1-chloro-isoquinolin-6-yloxy)-cyclohexyl]-carbamic acid tert-butyl ester (26, crude product) the title compound was prepared following the protocol described for trans-N-[4-(1-benzyloxy-isoquinolin-6-yloxy)-cyclohexyl]-acetamide (19). Final chromatography on a preparative HPLC gave a mixture of the desired product and the partially deprotected derivative having a free amino group. R$_t$=2.01 min (Method C). Detected mass: 449.2 (M+H$^+$).

cis-6-(4-Amino-cyclohexyloxy)-2H-isoquinolin-1-one (28)

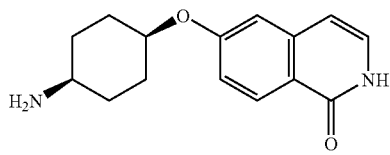 [SMILES: N[C@H]1CC[C@@H](Oc2ccc3c(=O)[nH]ccc3c2)CC1]

The title compound was prepared by stirring cis-[4-(1-Chloro-isoquinolin-6-yloxy)-cyclohexyl]-carbamic acid tert-butyl ester (27) at room temperature in methanol/2 N HCl (1:1). After complete conversion, the solvent was removed under reduced pressure and the residue was purified by preparative HPLC. The obtained trifluoroacetate was converted to the corresponding hydrochloride by dissolving the compound in 2 N HCl and evaporation of the solvent. After dissolving the residue in water and lyophilisation, the desired product (HCl-salt) was isolated as a colourless solid. R$_t$=0.75 min (Method B). Detected mass: 259, 2 (M+H$^+$).

General Procedure A for the Reductive Amination Reaction:

0.243 mmol of the amine building block (hydrochloride), 0.243 mmol of the aldehyde and 0.365 mmol of triethyl amine were stirred in 3 ml of HC(OMe)$_3$ for 1 h at room temperature. The mixture is cooled to −10° C., 1.75 ml of a freshly prepared DMF solution containing 1.215 mmol of NaHB(OAc)$_3$ and 1.215 mmol of HOAc is added. Stirring is continued at −10° C. for 30 min, the mixture is then allowed to warm to room temperature and left at room temperature over night. 0.5 ml of water was added and the mixture was evaporated, dissolved in DMF and mono- and bis-alkylated products, if obtained, were purified by preparative HPLC. The purified products were dissolved in 1 ml of HCl in isopropanol (5-6M) and left over night at RT (cleaves BOC/tBu ester groups off some of the products). 2 ml of water were added and the solution is freeze-dried to yield the hydrochlorides of the products.

According to this procedure the following products were obtained as hydrochlorides from the mentioned amine and carbonyl component (Table 1)

TABLE 1

| Example | Amine | Aldehyde/Ketone | Product | [M + H⁺] | $R_t$/[min] | Method |
|---|---|---|---|---|---|---|
| 29 | 7-chloro-6-((trans-4-aminocyclohexyl)oxy)isoquinolin-1(2H)-one | acetaldehyde | 7-chloro-6-((trans-4-(ethylamino)cyclohexyl)oxy)isoquinolin-1(2H)-one | 321.2 | 0.99 | A |
| 30 | 7-chloro-6-((trans-4-aminocyclohexyl)oxy)isoquinolin-1(2H)-one | propionaldehyde | 7-chloro-6-((trans-4-(propylamino)cyclohexyl)oxy)isoquinolin-1(2H)-one | 335.2 | 1.08 | A |
| 31 | 7-chloro-6-((trans-4-aminocyclohexyl)oxy)isoquinolin-1(2H)-one | butyraldehyde | 7-chloro-6-((trans-4-(butylamino)cyclohexyl)oxy)isoquinolin-1(2H)-one | 349.2 | 1.18 | A |
| 32 | 7-chloro-6-((trans-4-aminocyclohexyl)oxy)isoquinolin-1(2H)-one | acetone | 7-chloro-6-((trans-4-(isopropylamino)cyclohexyl)oxy)isoquinolin-1(2H)-one | 335.2 | 1.07 | A |
| 33 | 7-chloro-6-((trans-4-aminocyclohexyl)oxy)isoquinolin-1(2H)-one | isobutyraldehyde | 7-chloro-6-((trans-4-(isobutylamino)cyclohexyl)oxy)isoquinolin-1(2H)-one | 349.2 | 1.16 | A |
| 34 | 7-chloro-6-((trans-4-aminocyclohexyl)oxy)isoquinolin-1(2H)-one | cyclopropanecarbaldehyde | 7-chloro-6-((trans-4-((cyclopropylmethyl)amino)cyclohexyl)oxy)isoquinolin-1(2H)-one | 347.2 | 1.11 | A |

TABLE 1-continued
| Example | Amine | Aldehyde/Ketone | Product | [M+H]⁺ | R$_t$/[min] | Method |
|---|---|---|---|---|---|---|
| 35 | 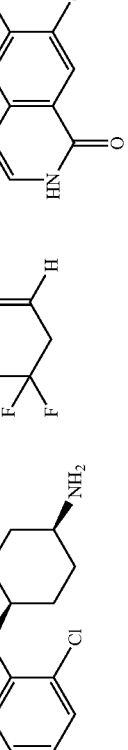 | 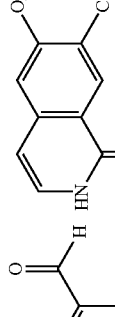 | 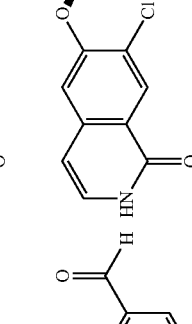 | 389.1 | 1.17 | A |
| 36 | 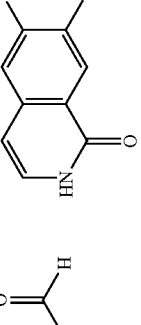 | 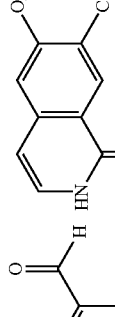 | 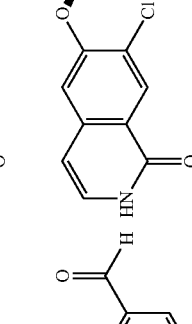 | 417.1 | 1.25 | B |
| 37 | 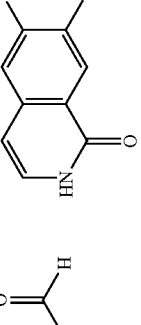 | 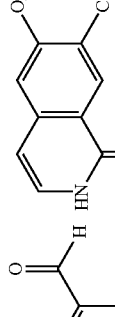 | 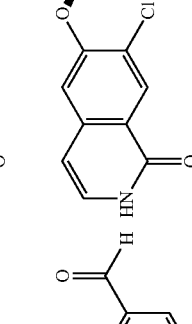 | 417.1 | 1.25 | B |
| 38 | 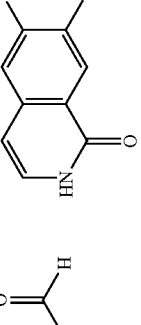 | 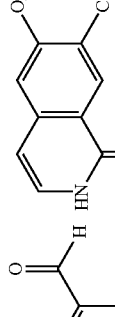 | 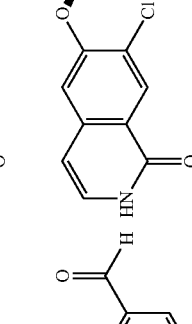 | 417.1 | 1.29 | B |
| 39 | 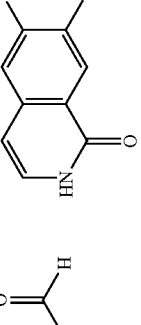 | 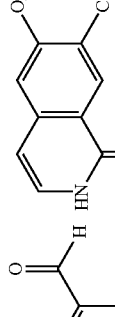 | 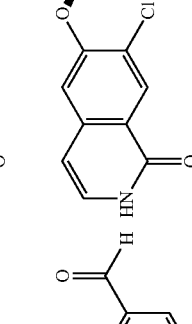 | 377.2 | 1.26 | A |

TABLE 1-continued

| Example | Amine | Aldehyde/Ketone | Product | [M + H]⁺ | R$_t$/[min] | Method |
|---|---|---|---|---|---|---|
| 40 | | | | 405.2 | 1.40 | A |
| 41 | | | | 401.2 | 1.28 | A |
| 42 | | | | 541.1 | 1.84 | A |
| 43 | | | | 321.2 | 1.01 | A |

TABLE 1-continued
| Example | Amine | Aldehyde/Ketone | Product | [M + H⁺] | $R_t$/[min] | Method |
|---|---|---|---|---|---|---|
| 44 | 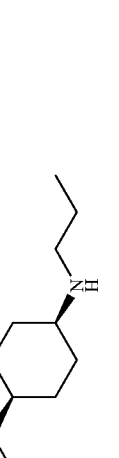 | 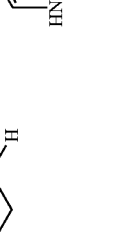 | 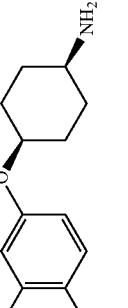 | 335.2 | 1.06 | B |
| 45 |  | 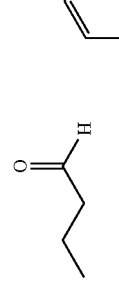 | 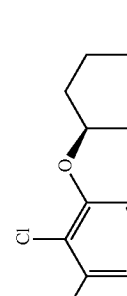 | 349.2 | 1.15 | B |
| 46 | 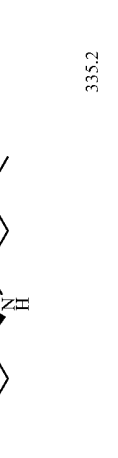 | 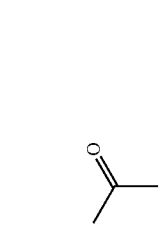 |  | 335.2 | 1.08 | B |
| 47 | 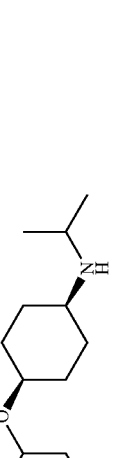 |  | 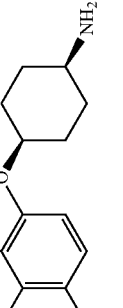 | 349.2 | 1.15 | B |
| 48 |  | 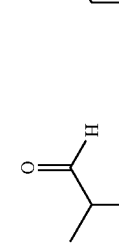 | 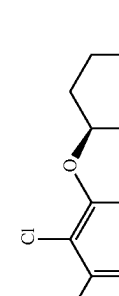 | 347.2 | 1.05 | B |

TABLE 1-continued

| Example | Amine | Aldehyde/Ketone | Product | [M+H]⁺ | R$_t$/[min] | Method |
|---|---|---|---|---|---|---|
| 49 | 5-chloro-6-((trans-4-aminocyclohexyl)oxy)isoquinolin-1(2H)-one | 4-chlorobenzaldehyde | 5-chloro-6-((trans-4-(bis(4-chlorobenzyl)amino)cyclohexyl)oxy)isoquinolin-1(2H)-one | 541.1 | 1.83 | A |
| 50 | 5-chloro-6-((trans-4-aminocyclohexyl)oxy)isoquinolin-1(2H)-one | 3-chlorobenzaldehyde | 5-chloro-6-((trans-4-(bis(3-chlorobenzyl)amino)cyclohexyl)oxy)isoquinolin-1(2H)-one | 541.1 | 1.88 | A |
| 51 | 5-chloro-6-((trans-4-aminocyclohexyl)oxy)isoquinolin-1(2H)-one | acetaldehyde | 5-chloro-6-((trans-4-(diethylamino)cyclohexyl)oxy)isoquinolin-1(2H)-one | 349.1 | 1.10 | A |
| 52 | 5-chloro-6-((trans-4-aminocyclohexyl)oxy)isoquinolin-1(2H)-one | propanal | 5-chloro-6-((trans-4-(dipropylamino)cyclohexyl)oxy)isoquinolin-1(2H)-one | 377.2 | 1.27 | A |

TABLE 1-continued

| Example | Amine | Aldehyde/Ketone | Product | [M + H⁺] | R$_t$/[min] | Method |
|---|---|---|---|---|---|---|
| 53 | 5-chloro-6-((trans-4-aminocyclohexyl)oxy)isoquinolin-1(2H)-one | butyraldehyde | 5-chloro-6-((trans-4-(dibutylamino)cyclohexyl)oxy)isoquinolin-1(2H)-one | 405.2 | 1.47 | A |
| 54 | 5-chloro-6-((trans-4-aminocyclohexyl)oxy)isoquinolin-1(2H)-one | isobutyraldehyde | 5-chloro-6-((trans-4-(diisobutylamino)cyclohexyl)oxy)isoquinolin-1(2H)-one | 405.2 | 1.45 | A |
| 55 | 5-chloro-6-((trans-4-aminocyclohexyl)oxy)isoquinolin-1(2H)-one | cyclopropanecarbaldehyde | 5-chloro-6-((trans-4-(bis(cyclopropylmethyl)amino)cyclohexyl)oxy)isoquinolin-1(2H)-one | 401.2 | 1.31 | A |
| 56 | 7-chloro-6-((trans-4-aminocyclohexyl)oxy)isoquinolin-1(2H)-one | acetaldehyde | 7-chloro-6-((trans-4-(diethylamino)cyclohexyl)oxy)isoquinolin-1(2H)-one | 349.2 | 1.10 | B |

TABLE 1-continued
| Example | Amine | Aldehyde/Ketone | Product | [M + H⁺] | R$_t$ [min] | Method |
|---|---|---|---|---|---|---|
| 57 | 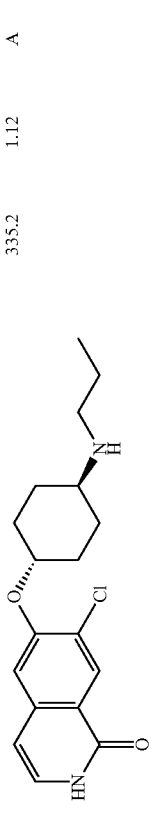 |  | 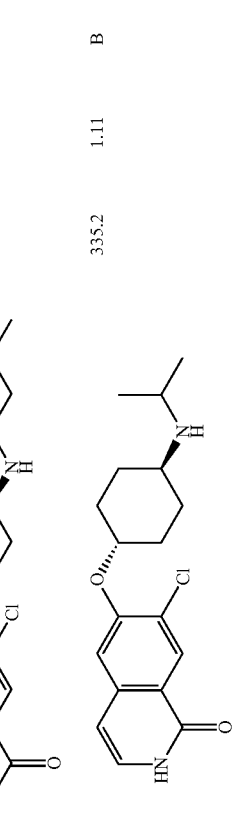 | 335.2 | 1.12 | A |
| 58 | 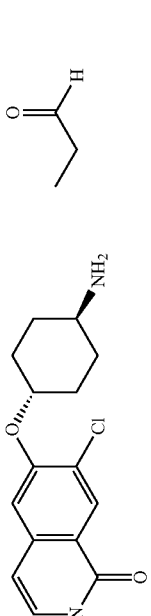 | 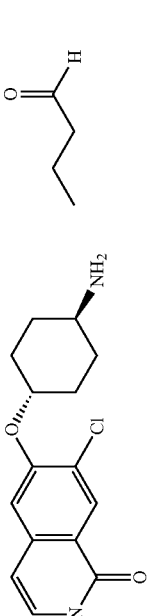 | 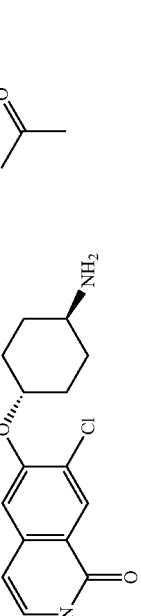 | 349.2 | 1.24 | B |
| 59 |  |  |  | 335.2 | 1.11 | B |
| 60 |  |  |  | 349.2 | 1.22 | B |
| 61 | | | | 541.1 | 1.86 | A |

TABLE 1-continued
| Example | Amine | Aldehyde/Ketone | Product | [M + H]⁺ | R_t [min] | Method |
|---|---|---|---|---|---|---|
| 62 | 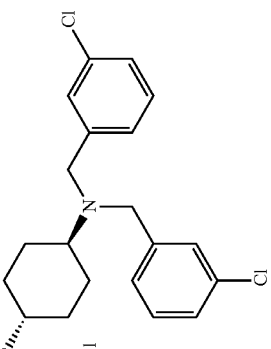 | 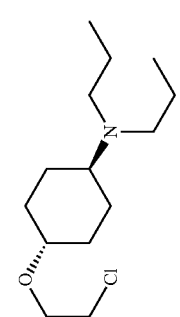 | 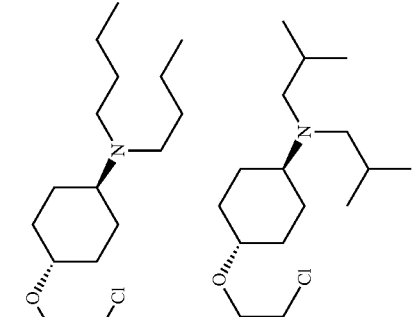 | 541.1 | 1.89 | A |
| 63 | 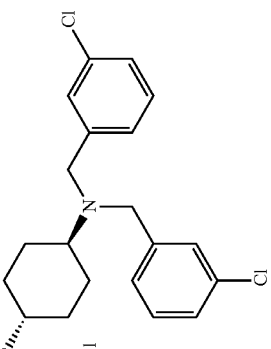 | 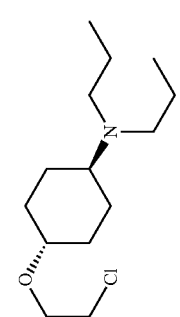 | 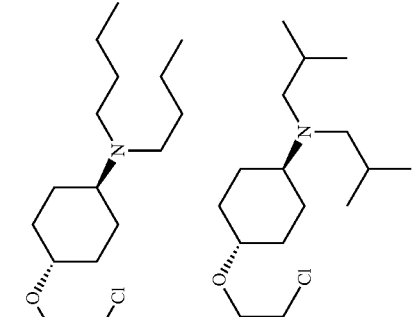 | 377.2 | 1.28 | A |
| 64 | 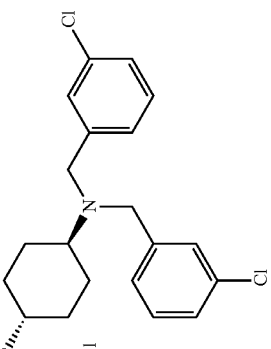 | 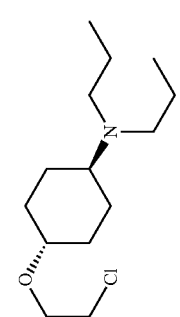 | 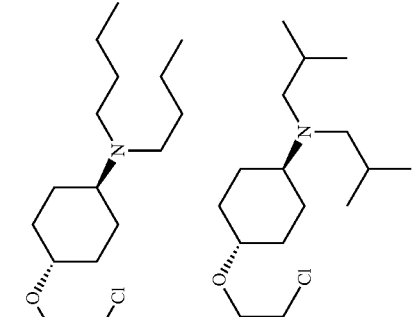 | 405.2 | 1.50 | A |
| 65 | 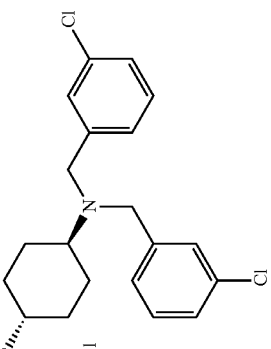 | 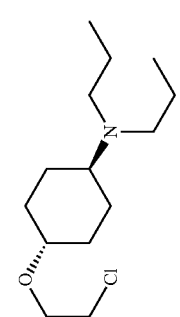 | 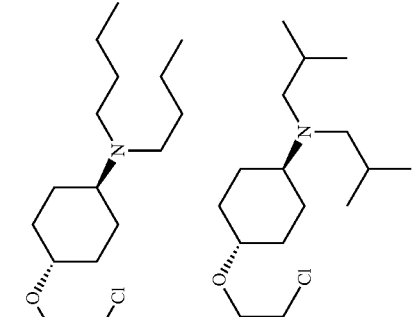 | 405.2 | 1.40 | A |

TABLE 1-continued
| Example | Amine | Aldehyde/Ketone | Product | [M + H⁺] | R$_t$ [min] | Method |
|---|---|---|---|---|---|---|
| 66 | 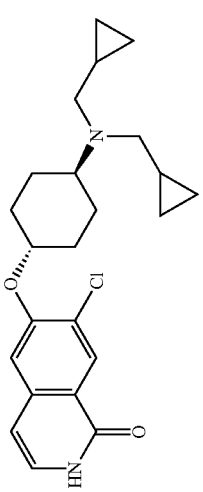 | 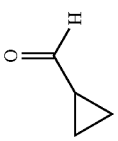 |  | 401.2 | 1.30 | A |

General Procedure B for the Reductive Amination Reaction:

150 mg (0.46 mmol) of 6-cis-(4-amino-cyclohexyloxy)-7-chloro-2H-isoquinolin-1-one hydrochloride (10) were dissolved in 10 ml of methanol. After addition of molecular sieves 4 A, 92.3 mg (0.57 mmol) of triethyl amine, 273.8 mg (4.56 mmol) of acetic acid and 0.57 mmol of the corresponding aldehyde, a solution of 86.0 mg (1.37 mmol) of sodium cyanoboro hydride is added dropwise and the mixture is stirred at room temperature until complete conversion is achieved. In some cases it was necessary to heat the mixture to 70° C. to achieve complete conversion. For the isolation of the products the solution was filtered and the solvent was removed under reduced pressure. The residue was dissolved in dichloromethane, washed with 1 N NaOH and sat. sodium chloride solution, dried with magnesium sulfate and evaporated. The mono- or bis alkylated products, if obtained, were purified by preparative HPLC or precipitated from methanolic HCl The obtained trifluoroacetates were stirred in 2 N HCl/Methanol, evaporated, dissolved in water and freeze dried to yield the desired products as hydrochlorides. Boc-protected products were deprotected during the evaporation of the HPLC-product fractions, which contained 0.1% TFA, or during the subsequent stirring in 2 N HCl/Methanol.

According to this procedure the following products were obtained as hydrochlorides from amine (10) and the mentioned aldehyde (Table 2)

TABLE 2

| Example | Aldehyde | Product | [M + H⁺] | $R_t$/[min] | Method |
|---|---|---|---|---|---|
| 67 | benzaldehyde | | 383.2 | 1.12 | B |
| 68 | 3,4-dichlorobenzaldehyde | | 451.1 | 1.30 | B |
| 69 | 3,5-dichlorobenzaldehyde | | 451.1 | 1.33 | B |
| 70 | 2,5-dichlorobenzaldehyde | | 451.1 | 1.28 | B |
| 71 | 2,4-dichlorobenzaldehyde | | 451.1 | 1.30 | B |

TABLE 2-continued

| Example | Aldehyde | Product | [M + H]⁺ | R$_t$/[min] | Method |
|---|---|---|---|---|---|
| 72 | pyridine-4-carbaldehyde | | 384.2 | 0.85 | B |
| 73 | 4-methylbenzaldehyde | | 397.2 | 1.23 | B |
| 74 | 4-methoxybenzaldehyde | | 413.2 | 1.18 | B |
| 75 | 4-(trifluoromethyl)benzaldehyde | | 451.1 | 1.30 | B |
| 78 | 4-(methylsulfonyl)benzaldehyde | | 461.1 | 1.09 | B |

TABLE 2-continued

| Example | Aldehyde | Product | [M + H]⁺ | R$_t$/[min] | Method |
|---|---|---|---|---|---|
| 77 | 2-naphthaldehyde | (isoquinolinone-cyclohexyloxy-naphthylmethylamine) | 433.2 | 1.36 | B |
| 78 | 2,3-dichlorobenzaldehyde | (isoquinolinone-cyclohexyloxy-(2,3-dichlorobenzyl)amine) | 451.1 | 1.33 | B |
| 79 | nicotinaldehyde (3-pyridine) | (isoquinolinone-cyclohexyloxy-(pyridin-3-ylmethyl)amine) | 384.2 | 0.87 | B |
| 80 | picolinaldehyde (2-pyridine) | (isoquinolinone-cyclohexyloxy-(pyridin-2-ylmethyl)amine) | 384.2 | 1.10 | B |
| 81 | picolinaldehyde (2-pyridine) | (isoquinolinone-cyclohexyloxy-bis(pyridin-2-ylmethyl)amine) | 475.5 | 0.98 | C |

TABLE 2-continued

| Example | Aldehyde | Product | [M + H]+ | R$_t$/[min] | Method |
|---|---|---|---|---|---|
| 82 | | | 404.2 | 0.88 | B |
| 83 | | | 387.2 | 0.97 | B |
| 84 | | | 376.2 | 0.84 | B |
| 85 | | | 423.1 | 1.21 | B |
| 86 | | | 386.2 | 1.11 | B |

TABLE 2-continued
| Example | Aldehyde | Product | [M + H]+ | Rt [min] | Method |
|---|---|---|---|---|---|
| 87 | 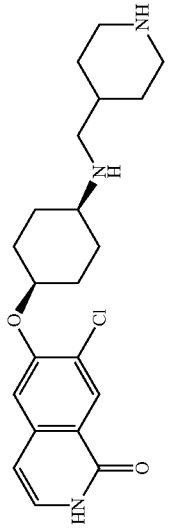 |  | 390.2 | 0.87 | B |
| 88 | 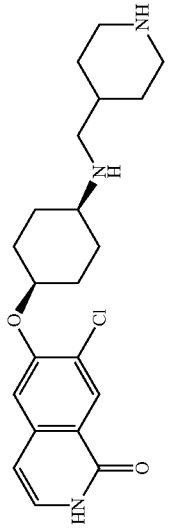 |  | 390.2 | 0.86 | B |
| 89 | 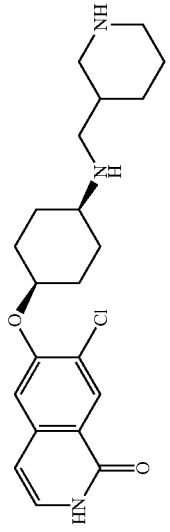 | 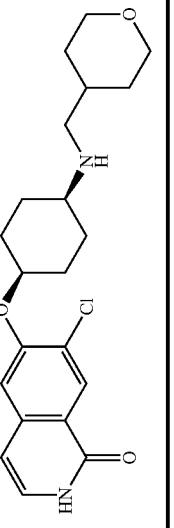 | 389.1 | 1.10 | B |
| 91 | 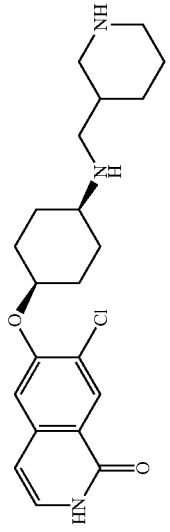 | 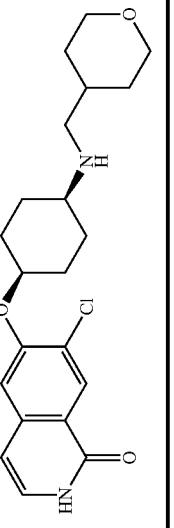 | 391.2 | 1.08 | B |

7-Bromo-6-fluoro-isoquinoline 2-oxide (93)

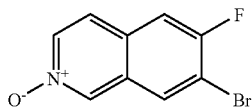 [SMILES: [O-][n+]1ccc2cc(F)c(Br)cc2c1]

Starting from (92) the title compound was prepared following the method described for 7-chloro-6-fluoro-isoquinoline 2-oxide (5). $R_t$=0.93 min (Method C). Detected mass: 242.2/244.2 (M+H$^+$).

7-Bromo-1-chloro-6-fluoro-isoquinoline (94)

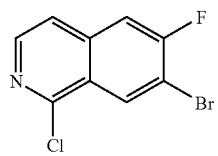 [SMILES: Fc1cc2ccnc(Cl)c2cc1Br]

Starting from 7-bromo-6-fluoro-isoquinoline 2-oxide (93) the desired product was synthesized according to the protocol described for 1,7-dichloro-6-fluoro-isoquinoline (6). $R_t$=1.70 min (Method C). Detected mass: 260.0/262.0 (M+H$^+$).

7-Bromo-6-fluoro-2H-isoquinolin-1-one (95)

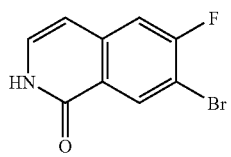 [SMILES: O=c1[nH]ccc2cc(F)c(Br)cc12]

12.9 g (49.5 mmol) 7-bromo-1-chloro-6-fluoro-isoquinoline (94) were dissolved in 250 ml of acetic acid. After addition of 38.7 g (0.5 mol) of ammonium acetate, the solution is stirred at 100° C. After 3 h, the solvent was removed under reduced pressure and the residue was poured into water. The precipitate is filtered and dried to yield 9.91 g (83%) of the title compound. $R_t$=1.15 min (Method C). Detected mass: 242.2/244.1 (M+H$^+$).

7-Bromo-6-fluoro-2-(4-methoxy-benzyl)-2H-isoquinolin-1-one (96)

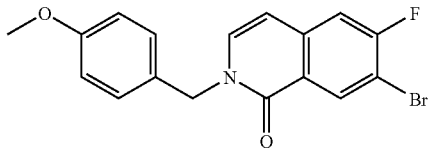 [SMILES: COc1ccc(Cn2ccc3cc(F)c(Br)cc3c2=O)cc1]

9.66 g (39.9 mmol) of 7-Bbromo-6-fluoro-2H-isoquinolin-1-one (95) were dissolved in 180 ml of dimethyl acetamide and 1.92 g (48.0 mmol) of sodium hydride (60%) were added. After 1 h at room temperature a solution of 7.50 g (48.0 mmol) of 4-methoxy benzylchloride in 25 ml of dimethyl acetamide was added. The mixture was stirred at room temperature until complete conversion was achieved. The solvent was removed under reduced pressure, the residue was taken up in saturated sodium bicarbonate solution and extracted three times with dichloromethane. The organic layers were dried with magnesium sulfate and evaporated to yield 16.8 g of a dark oil as crude product, which was stirred in methanol. Filtration of the precipitate gave 6.56 g of the title compound as a yellow solid. The mother liquor was evaporated and the residue purified by preparative HPLC to yield additional 2.62 g of the desired product. $R_t$=1.71 min (Method C). Detected mass: 362.3/364.3 (M+H$^+$).

6-cis-(4-Amino-cyclohexyloxy)-7-bromo-2-(4-methoxy-benzyl)-2H-isoquinolin-1-one (97)

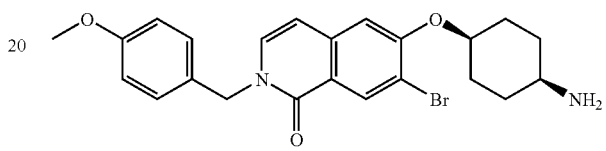

135 mg (0.625 mmol) of cis-(4-hydroxy-cyclohexyl)-carbamic acid tert-butyl ester were dissolved in 2.5 ml of dimethyl acetamide and 30 mg (0.75 mmol) of sodium hydride (60%) were added. After stirring for 15 minutes at room temperature 181 mg (0.5 mmol) of 7-bromo-6-fluoro-2-(4-methoxy-benzyl)-2H-isoquinolin-1-one (96) were added and stirring was continued. To achieve complete conversion, additional 30 mg of sodium hydride (60%) were added after 3 h. After stirring overnight 2 ml of acetic acid followed by 2 ml of 2 N HCl were added and the mixture was stirred at 50° C. until the deprotection of the Boc-group was complete. The solvent was removed under reduced pressure, the residue dissolved in saturated sodium bicarbonate solution and extracted three times with dichloromethane. The organic layers were dried with magnesium sulfate and evaporated. Final purification by preparative HPLC gave 83 mg of the product as trifluoroacetate. $R_t$=1.31 min (Method B). Detected mass: 457.2/459.2 (M+H$^+$).

6-cis-(4-Amino-cyclohexyloxy)-7-bromo-2H-isoquinolin-1-one (98)

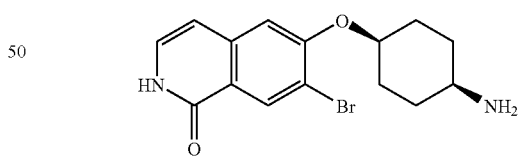

62 mg (0.11 mmol) of 6-(4-amino-cyclohexyloxy)-7-bromo-2-(4-methoxy-benzyl)-2H-isoquinolin-1-one trifluoroacetate (97) were dissolved in 2 ml of TFA and heated in a microwave oven at 140° C. for 2 h. The solvent was removed under reduced pressure. The residue was dissolved in 2 N HCl and washed twice with dichloromethane. The combined organic layers were extracted with 2 N HCl and the combined aqueous solutions were evaporated. The residues were dissolved in water and freeze dried. Final purification by preparative HPLC gave 8 mg of the desired product as trifluoroacetate. $R_t$=0.86 min (Method B). Detected mass: 337.1/339.1 (M+H$^+$).

6-trans-(4-Amino-cyclohexyloxy)-7-bromo-2-(4-methoxy-benzyl)-2H-iso-quinolin-1-one (99)

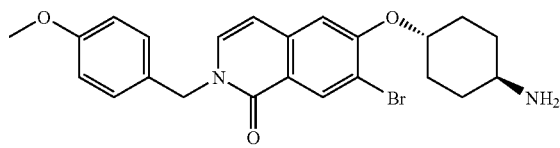 [SMILES: COc1ccc(Cn2ccc3cc(O[C@H]4CC[C@H](N)CC4)c(Br)cc3c2=O)cc1]

Starting with trans-(4-hydroxy-cyclohexyl)-carbamic acid tert-butyl ester and 7-bromo-6-fluoro-2-(4-methoxy-benzyl)-2H-isoquinolin-1-one (96) the title compound was synthesized following the protocol described for 6-cis-(4-amino-cyclohexyloxy)-7-bromo-2-(4-methoxy-benzyl)-2H-isoquinolin-1-one (97). $R_t$=1.34 min (Method B). Detected mass: 457.2/459.2 (M+H$^+$).

6-trans-(4-Amino-cyclohexyloxy)-7-bromo-2H-isoquinolin-1-one (100)

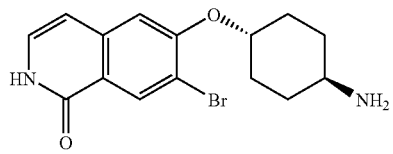

Starting from 6-trans-(4-amino-cyclohexyloxy)-7-bromo-2-(4-methoxy-benzyl)-2H-iso-quinolin-1-one (99) the desired product was prepared by the methode described for 6-cis-(4-amino-cyclohexyloxy)-7-bromo-2H-isoquinolin-1-one (98). The compound was isolated as trifluoroacetate. $R_t$=0.88 min (Method B). Detected mass: 337.1/339.1 (M+H$^+$).

7-Chloro-6-fluoro-2H-isoquinolin-1-one (101)

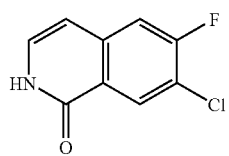

Starting from 1,7-dichloro-6-fluoro-isoquinoline (6) the title compound was prepared following the protocol described for 7-bromo-6-fluoro-2H-isoquinolin-1-one (95). $R_t$=1.11 min (Method C). Detected mass: 198.2 (M+H$^+$).

7-Chloro-6-fluoro-2-(4-methoxy-benzyl)-2H-iso-quinolin-1-one (102)

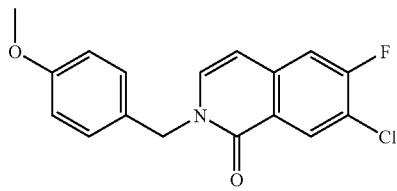 [SMILES: COc1ccc(Cn2ccc3cc(F)c(Cl)cc3c2=O)cc1]

Starting from 7-chloro-6-fluoro-2H-isoquinolin-1-one (101) the title compound was prepared following the protocol described for 7-bromo-6-fluoro-2-(4-methoxy-benzyl)-2H-isoquinolin-1-one (96). $R_t$=1.66 min (Method C). Detected mass: 318.3 (M+H$^+$).

1-Benzyloxy-7-chloro-6-fluoro-isoquinoline (103)

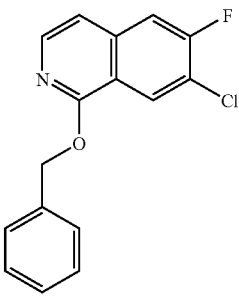 [SMILES: Fc1cc2ccnc(OCc3ccccc3)c2cc1Cl]

14.74 g (74.6 mmol) of 7-chloro-6-fluoro-2H-isoquinolin-1-one (101) were dissolved in 150 ml of toluene. After addition of 30.86 g (111.9 mmol) of silver carbonate and 15.31 g (89.5 mmol) of benzyl bromide, the mixture was stirred at 80° C. for 3 h. After cooling down to room temperature, the reaction mixture was filtered and the filtrate was evaporated. The residue was dissolved in dichloromethane and washed with water, dried with magnesium sulfate and evaporated. Final purification by preparative HPLC gave 11.63 g of the title compound. $R_t$=2.51 min (Method B). Detected mass: 288.1/290.1 (M+H$^+$).

General Procedure for the reaction of the arylchlorides 7-chloro-6-fluoro-2-(4-methoxy-benzyl)-2H-isoquinolin-1-one (102) and 1-benzyloxy-7-chloro-6-fluoro-isoquinoline (103) with grignard reagents under Fe(acac)$_3$ catalysis.

2 mmol of the respective arylchloride and 35.3 mg (0.1 mmol) of iron(III) acetylacetonate were dissolved in 24 ml of THF and 2 ml of NMP were added. At 0° C. 2.4 mmol of the grignard reagent were added via syringe under argon and the reaction was stirred at 0° C. for 10 minutes. To achieve complete conversion, in some cases another 0.6 mmol of the grignard reagent were added and stirring was continued for 10 minutes.

In the case of the N-PMB-protected compounds, the reaction was quenched by pouring into 1M HCl. The O-Benzyl protected analogs were quenched by pouring into saturated NH$_4$Cl-solution.

The mixture was evaporated and the residue was dissolved in dichloromethane and washed with water. The organic layer was dried with Na$_2$SO$_4$ and the solvent was removed under reduced pressure. Final purification by preparative HPLC gave the desired 7-alkylated derivatives.

According to this procedure the following products were obtained from the mentioned arylchloride and Grignard reagent (Table 3)

TABLE 3

| Example | Arylchloride | Grignard reagent | Product | [M + H⁺] | R$_t$/[min] | Method |
|---|---|---|---|---|---|---|
| 104 | 102 | ethyl MgCl | 6-fluoro-7-ethyl-2-(4-methoxybenzyl)-2H-isoquinolin-1-one | 312.4 | 1.68 | C |
| 105 | 102 | propyl MgCl | 6-fluoro-7-propyl-2-(4-methoxybenzyl)-2H-isoquinolin-1-one | 326.4 | 1.81 | C |
| 106 | 102 | butyl MgCl | 6-fluoro-7-butyl-2-(4-methoxybenzyl)-2H-isoquinolin-1-one | 340.4 | 1.92 | C |
| 107 | 102 | isopropyl MgCl | 6-fluoro-7-isopropyl-2-(4-methoxybenzyl)-2H-isoquinolin-1-one | 326.4 | 1.80 | C |
| 108 | 103 | cyclopropyl MgBr | 6-fluoro-7-cyclopropyl-1-benzyloxy-isoquinoline | 294.4 | 2.09 | C |

6-cis-(4-Amino-cyclohexyloxy)-2-(4-methoxy-benzyl)-7-propyl-2H-isoquinolin-1-one (109)

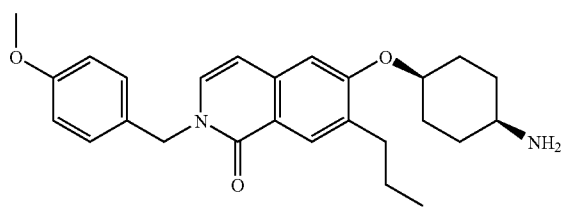 [SMILES: CCCCc1cc2c(=O)n(Cc3ccc(OC)cc3)ccc2cc1O[C@H]1CC[C@@H](N)CC1]

58 mg (0.38 mmol) of cis 4-aminocyclohexanol hydrochloride were dissolved in 10 ml of dimethyl acetamide. Under argon, 38 mg (0.96 mmol) of sodium hydride (60%) were added and the reaction was stirred for 30 minutes at room temperature. After addition of a solution of 100 mg (0.31 mmol) of 6-fluoro-2-(4-methoxy-benzyl)-7-propyl-2H-isoquinolin-1-one (105) the solution was stirred at 80° C. To obtain complete conversion, the same amounts of the 4-aminocyclhexanol hydrochloride and sodium hydride were added twice and the temperature was increased to 110° C. After complete conversion, the solvent was removed under reduced pressure. The residue was dissolved in dichloromethane and washed with water. The organic layer was dried with magnesium sulfate and evaporated. After purification by preparative HPLC the desired product was isolated as trifluoroacetate. R$_t$=1.14 min (Method C). Detected mass: 421.6 (M+H⁺).

The following compounds were prepared as trifluoroacetates by the protocol described for 6-cis-(4-Amino-cyclohexyloxy)-2-(4-methoxy-benzyl)-7-propyl-2H-isoquinolin-1-one (109) (Table 4):

TABLE 4

| Example | Arylfluoride | Product | [M + H⁺] | R_t/[min] | Method |
|---|---|---|---|---|---|
| 110 | 106 | | 435.6 | 1.18 | C |
| 111 | 107 | | 421.6 | 1.13 | C |
| 112 | 108 | | 389.5 | 1.22 | C |

Deprotection of the N-PMB-Protected Isoquinolinones 109, 110 and 111

The protected starting compounds were heated in TFA in a microwave oven at 140° C. until complete conversion was observed. Evaporation of the solvent and purification by preparative HPLC gave the desired deprotected products as trifluoroacetates, which were dissolved in 2 N HCl and evaporated. After dissolving the residue in water and lyophilization, the compounds were isolated as HCl-salts.

Deprotection of the O-benzyl Protected Isoquinolinone 112

4-(1-Benzyloxy-7-cyclopropyl-isoquinolin-6-yloxy)-cyclohexylamine (112) was stirred in 2 N HCl at room temperature until conversion is complete. After evaporation of the solvent under reduced pressure, the crude product was purified by preparative HPLC, which gave the desired product as trifluoroacetate. The product was dissolved in 2 N HCl and the solvent was removed under reduced pressure. After dissolving the residue in water and lyophilization, the product was isolated as HCl-salt.

After deprotection of the compounds 109 to 112, the following compounds were isolated as HCl salts (Table 5):

TABLE 5

| Example | Starting compound | Product | [M + H⁺] | R_t/[min] | Method |
|---|---|---|---|---|---|
| 113 | 109 | | 301.4 | 0.89 | C |
| 114 | 110 | | 315.4 | 0.93 | C |
| 115 | 111 | | 301.4 | 0.86 | C |

TABLE 5-continued

| Example | Starting compound | Product | [M + H⁺] | R_f/[min] | Method |
|---|---|---|---|---|---|
| 116 | 112 | (structure) | 299.4 | 0.82 | C |

General Procedure C for the Reductive Amination Reaction:

82 mg (0.25 mmol) of 6-trans-(4-amino-cyclohexyloxy)-7-chloro-2H-isoquinolin-1-one hydrochloride (14) were dissolved in 3 ml of trimethoxy methane. 0.25 mmol of the corresponding aldehyde or ketone were added (dissolved in 0.2 ml of THF or as a solid) followed by 48 mg (0.375 mmol) of triethylamine. After 1 h at room temperature the solution was cooled to −10° C. and a solution of 265 mg (1.25 mmol) of sodium triacetoxy borohydride in 1.5 ml DMF was added, followed by 73.5 mg (1.225 mmol) of acetic acid. After 30 min at 0° C., the solution was left at room temperature overnight. For workup, 0.5 ml of water were added and the solvent was removed under reduced pressure. The residue was purified by preparative HPLC. The obtained trifluoroacetates were dissolved in 1.0 ml of a 5-6 M HCl solution in isopropanol and left at room temperature overnight. After addition of 2.0 ml of water, the solutions were lyophilized yielding the desired products as HCl-salts.

The compounds listed in table 6 below were synthesized according to this method and obtained as HCl salt:

TABLE 6

| Example | Aldehyde | Product | [M + H⁺] | R_f/[min] | Method |
|---|---|---|---|---|---|
| 117 | (structure) | (structure) | 347.1 | 1.11 | A |
| 118 | (structure) | (structure) | 389.1 | 1.13 | A |
| 119 | (structure) | (structure) | 363.1 | 1.26 | A |
| 120 | (structure) | (structure) | 389.1 | 1.34 | A |
| 121 | (structure) | (structure) | 375.5 | 1.34 | D |
| 122 | (structure) | (structure) | 417.4 | 1.41 | D |

TABLE 6-continued

| Example | Aldehyde | Product | [M + H⁺] | $R_t$/[min] | Method |
|---|---|---|---|---|---|
| 123 | (3-chlorobenzaldehyde) | (isoquinolinone product) | 417.4 | 1.43 | D |
| 124 | (2,4-dichlorobenzaldehyde) | (isoquinolinone product) | 451.3 | 1.46 | D |

6-[cis-4-(Cyclopropylmethyl-amino)-cyclohexyloxy]-2H-isoquinolin-1-one (125)

125 was obtained as hydrochloride using the previously described general method employing cyclopropane carbaldehyde and cis-6-(4-amino-cyclohexyloxy)-2H-isoquinolin-1-one (28) as starting materials. $R_t$=1.04 min (Method B). Detected mass: 313.2 (M+H⁺).

7-Benzylsulfanyl-6-fluoro-2-(4-methoxy-benzyl)-2H-isoquinolin-1-one (126)

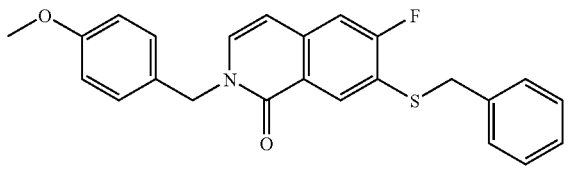 [SMILES: COc1ccc(Cn2ccc3cc(F)c(SCc4ccccc4)cc3c2=O)cc1]

500 mg (1.38 mmol) of 7-bromo-6-fluoro-2-(4-methoxy-benzyl)-2H-isoquinolin-1-one (96), 627.3 mg (1.52 mmol) of tributyltin benzylthiolate, 96.2 mg (1.66 mmol) of freshly dried potassium fluoride and 24.0 mg (0.041 mmol) of XANTPHOS were dissolved in 5 ml of NMP and stirred for 15 min at room temperature. After addition of 19.0 mg (0.021 mmol) of Pd₂ dba₃, the reaction mixture was stirred at 100° C. To achieve complete conversion, another 0.01 mmol of Pd₂ dba₃ were added and stirring was continued at 100° C. After 5 h the solution was cooled to room temperature, diluted with ethyl acetate (10 ml) and treated with 5% KF-solution. The mixture was stirred vigorously for 15 minutes and filtered. The filtrate was separated and the organic phase was washed twice with water and once with saturated sodium chloride solution. After drying with magnesium sulfate, the organic layer was evaporated and the crude product was purified by preparative HPLC. $R_t$=1.83 min (Method C). Detected mass: 406.5 (M+H⁺).

6-(4-Amino-cis-cyclohexyloxy)-7-benzylsulfanyl-2-(4-methoxy-benzyl)-2H-iso-quinolin-1-one (127)

90 mg (0.59 mmol) of cis 4-amino-cyclohexanol hydrochloride were dissolved in 10 ml dimethyl acetamide and 59.3 mg (1.48 mmol) of sodium hydride (60%) were added. After stirring 30 minutes at room temperature, a solution of 200 mg (0.49 mmol) of 7-benzylsulfanyl-6-fluoro-2-(4-methoxy-benzyl)-2H-isoquinolin-1-one (126) in 20 ml of dimethyl acetamide was added and the mixture was stirred at 80° C. for 1 h, then at 130° C. for 3 h. Another 1.2 equivalents of cis 4-amino-cyclohexanol hydrochloride and 2.5 equivalents of sodium hydride were added and the temperature was increased to 160° C. After 8 h the solution is cooled down to room temperature and the solvent is removed under reduced pressure. The residue is dissolved in dichloromethane, washed with water and dried with magnesium sulfate. After evaporation of the solvent and purification by preparative HPLC, the title compound was isolated as trifluoroacetate. $R_t$=1.18 min (Method C). Detected mass: 501.6 (M+H⁺).

N-{4-[7-Benzylsulfanyl-2-(4-methoxy-benzyl)-1-oxo-1,2-dihydro-isoquinolin-6-yloxy]-cis-cyclohexyl}-acetamide (128)

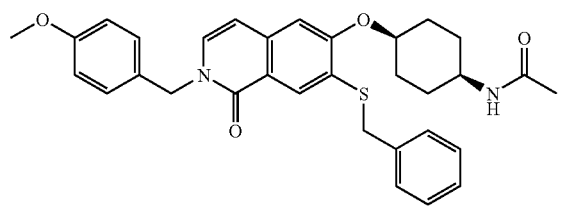 [SMILES: COc1ccc(Cn2ccc3cc(O[C@H]4CC[C@@H](NC(C)=O)CC4)c(SCc4ccccc4)cc3c2=O)cc1]

45 mg (0.073 mmol) of 6-(4-amino-cis-cyclohexyloxy)-7-benzylsulfanyl-2-(4-methoxy-benzyl)-2H-iso-quinolin-1-one (127) were dissolved in 5 ml of dichloromethane and 14.8 mg (0.146 mmol) of triethylamine were added. At 0° C., 6.9 mg (0.088 mmol) of acetylchloride were added and the solution was stirred at room temperature. After 2 h, dichloromethane was added and the solution was washed with 2 N HCl and saturated sodium bicarbonate solution. After drying with magnesium sulfate and evaporation of the solvent, the title compound was isolated as crude product, which was used without further purification. $R_t$=1.53 min (Method C). Detected mass: 543.6 (M+H$^+$).

6-(4-Acetylamino-cis-cyclohexyloxy)-4-chloro-2-(4-methoxy-benzyl)-1-oxo-1,2-dihydro-isoquinoline-7-sulfonyl chloride (129)

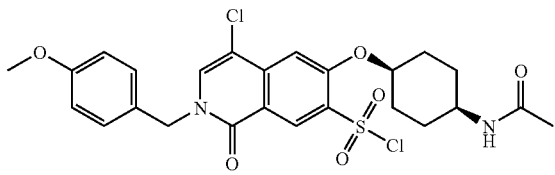 [SMILES: COc1ccc(Cn2cc(Cl)c3cc(O[C@H]4CC[C@@H](NC(C)=O)CC4)c(S(=O)(=O)Cl)cc3c2=O)cc1]

37 mg of N-{4-[7-benzylsulfanyl-2-(4-methoxy-benzyl)-1-oxo-1,2-dihydro-isoquinolin-6-yloxy]-cyclohexyl}-acetamide (128, crude product) were dissolved in 5 ml of dichloromethane. At 0° C., 16.4 mg (0.273 mmol) of acetic acid, 4.9 mg (0.273 mmol) of water and 273 µl (0.273 mmol) of sulfuryl chloride (1 M in dichloromethane) were added. After 30 minutes, ethyl acetate was added and the solution was washed with sodium bicarbonate solution (2%), water and saturated sodium chloride solution. The organic layer was dried with Na$_2$SO$_4$ and evaporated. The so obtained crude product was used without further purification. $R_t$=1.55 min (Method C). Detected mass: 553.5 (M+H$^+$).

N-{4-[4-Chloro-2-(4-methoxy-benzyl)-1-oxo-7-sulfamoyl-1,2-dihydro-isoquinolin-6-yloxy]-cis-cyclohexyl}-acetamide (130)

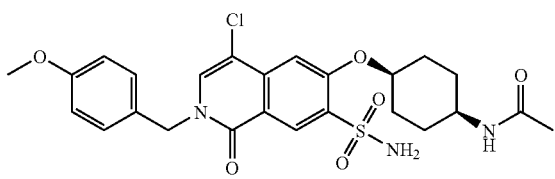 [SMILES: COc1ccc(Cn2cc(Cl)c3cc(O[C@H]4CC[C@@H](NC(C)=O)CC4)c(S(N)(=O)=O)cc3c2=O)cc1]

To a solution of 29 mg of 6-(4-acetylamino-cis-cyclohexyloxy)-4-chloro-2-(4-methoxy-benzyl)-1-oxo-1,2-dihydro-isoquinoline-7-sulfonyl chloride (129, crude product) in 2 ml of THF 2 ml of 33% aqueous ammonia solution were added. After 1 h at room temperature the solvent was removed under reduced pressure and the crude product was used without further purification. $R_t$=1.22 min (Method C). Detected mass: 534.5 (M+H$^+$).

6-(4-Amino-cis-cyclohexyloxy)-4-chloro-2-(4-methoxy-benzyl)-1-oxo-1,2-dihydro-isoquinoline-7-sulfonic acid amide (131)

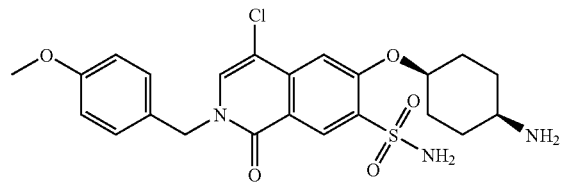 [SMILES: COc1ccc(Cn2cc(Cl)c3cc(O[C@H]4CC[C@@H](N)CC4)c(S(N)(=O)=O)cc3c2=O)cc1]

32 mg of N-{4-[4-chloro-2-(4-methoxy-benzyl)-1-oxo-7-sulfamoyl-1,2-dihydro-isoquinolin-6-yloxy]-cis-cyclohexyl}-acetamide (130, crude product) were dissolved in 5 ml of ethanol and 15 ml of 2 N HCl and heated for 2 h at 90° C. The solvent was removed under reduced pressure and the residue was dissolved in 6 N HCl and heating at 90° C. was continued for 20 h. After cooling down to room temperature, the aqueous solution was evaporated and the title compound was isolated as HCl-salt (crude product). $R_t$=1.00 min (Method C). Detected mass: 492.5 (M+H$^+$).

6-(4-Amino-cis-cyclohexyloxy)-4-chloro-1-oxo-1,2-dihydro-isoquinoline-7-sulfonic acid amide (132)

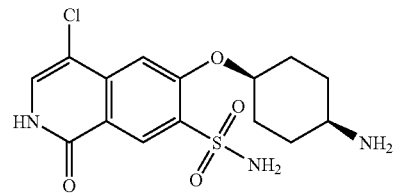 [SMILES: NS(=O)(=O)c1cc2c(=O)[nH]cc(Cl)c2cc1O[C@H]1CC[C@@H](N)CC1]

Crude 131 was dissolved in 15 ml of trifluoroacetic acid and heated for 3 h at 140° C. under microwave conditions. After evaporation of the solvent, the crude product was purified by preparative HPLC, which delivers the title compound as trifluoroacetate. $R_t$=0.90 min (Method B). Detected mass: 372.3 (M+H$^+$).

1-Benzyloxy-7-chloro-6-(1,4-dioxa-spiro[4.5]dec-8-yloxy)-isoquinoline (133)

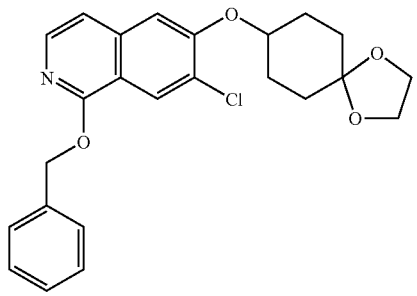 [SMILES: Clc1cc2c(OCc3ccccc3)nccc2cc1OC1CCC2(CC1)OCCO2]

1.26 g (8.34 mmol) of dioxa-spiro[4.5]decan-8-ol were dissolved in 50 ml of dimethyl acetamide and 695.2 mg (17.4 mmol) of sodium hydride (60%) were added. After stirring 30 minutes at room temperature a solution of 2.0 g (6.95 mmol) of 1-benzyloxy-7-chloro-6-fluoro-isoquinoline (103) in 50 ml of dimethyl acetamide was added and stirring was continued at room temperature. After 1 h the solvent was removed under reduced pressure. The residue was dissolved in dichloromethane and washed with water. The organic layer was dried with magnesium sulfate and evaporated, which gave 3.30 g of the crude product, which was used without further purification. $R_t$=2.05 min (Method C). Detected mass: 426.5 $(M+H^+)$.

7-Chloro-6-(4-oxo-cyclohexyloxy)-2H-isoquinolin-1-one (134)

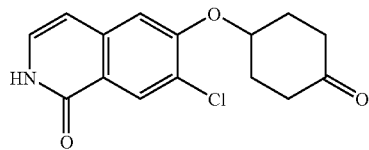 [SMILES: O=C1CCC(Oc2cc3cc[nH]c(=O)c3cc2Cl)CC1]

3.30 g of 1-benzyloxy-7-chloro-6-(1,4-dioxa-spiro[4.5]dec-8-yloxy)-isoquinoline (133, crude product) were stirred in 30 ml of 6 N HCl/acetone (1:2) at room temperature. After 3 h the reaction mixture was poured on saturated sodium bicarbonate solution and extracted with dichloromethane. The organic layer was dried with magnesium sulfate and evaporated. The crude product was purified by preparative HPLC. $R_t$=1.34 min (Method B). Detected mass: 292.0 $(M+H^+)$.

Starting from 7-chloro-6-(4-oxo-cyclohexyloxy)-2H-isoquinolin-1-one (134), the following compounds were synthesized as hydrochlorides in analogy to the general procedure B for the reductive amination reactions (Table 7):

a) 6-Fluoro-7-methyl-2H-isoquinolin-1-one

To a solution of 10.0 g (55.5 mmol) of 3-fluoro-4-methyl-cinnamic acid in 80 ml of acetone were subsequently added at 0° C. 6.74 g (66.6 mmol) of triethylamine in 10 ml of acetone followed by 7.83 g (72.2 mmol) of ethyl chloroformate. After stirring for 2 h at 0 to 5° C. a solution of 4.0 g (61.1 mmol) of sodium azide in 9.5 ml of water was added. After stirring for 1 additional h the reaction mixture was poured onto 200 ml of ice water and extraced twice with chloroform. The organic phase was dried over magnesium sulfate, 40 ml diphenylether were added and the chloroform was cautiously removed in vacuo. The residue was then added dropwise into 50 ml of diphenylether, which had been preheated to 245° C. After complete addition it was stirred further for 1 h at 230-250° C. After cooling down to 150° C. the reaction mixture was poured into 270 ml of heptane and after further cooling in an ice bath the precipitated product was filtered by suction and 4.1 g 6-fluoro-7-methyl-2H-isoquinolin-1-one were obtained.

b) 6-Fluoro-2-(4-methoxy-benzyl)-7-methyl-2H-isoquinolin-1-one

To a solution of 9.17 g (51.8 mmol) of 6-fluoro-7-methyl-2H-isoquinolin-1-one in 80 ml of DMF were added 20.2 g (62.1 mmol) of cesium carbonate and then 8.92 g (56.9 mmol) of 4-methoxybenzylchloride. After stirring at room temperature for 90 minutes the reaction mixture was poured into 600 ml of water, stirred for 1 h, and then the precipitated product was isolated by suction. From the mother liquor additional producted was isolated by chromatography with heptane/ethyl acetate (80:20). The combined products were recrystallized from ethyl acetate and 8.39 g 6-fluoro-2-(4-methoxy-benzyl)-7-methyl-2H-isoquinolin-1-one were received.

TABLE 7

| Example | Amine | Product | Remark | [M + H⁺] | $R_t$/[min] | Method |
|---|---|---|---|---|---|---|
| 135 | (structure) | (structure) | cis- and trans isomers separated by prep. HPLC; cis-isomer obtained in approx. 80% purity. | 321.1 | 0.99 | B |
| 136 | (structure) | (structure) | cis- and trans isomers separated by prep. HPLC; cis-isomer obtained in approx. 85% purity. | 321.1 | 0.92 | B |

6-(trans-4-Amino-cyclohexyloxy)-7-methyl-2H-isoquinolin-1-one (137)

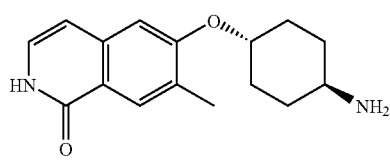

c) 6-(trans-4-Amino-cyclohexyloxy)-2-(4-methoxy-benzyl)-7-methyl-2H-isoquinolin-1-one To a solution of 1.48 g (9.75 mmol) of trans-4-aminocyclohexanol hydrochloride in 20 ml of dimethylacetamide where added 1.95 g (48.77 mmol) of sodium hydride (60%) and the mixture was stirred for 15 minutes. Subsequently 2.90 g (9.75 mmol) of 6-fluoro-2-(4-methoxy-benzyl)-7-methyl-2H-isoquinolin-1-one in 30 ml of dimethylacetamide were added and the reaction mixture was heated to 80° C. for 2 days. After cooling the mixture was poured into 300 ml of ice water and the precipitated crude product was purified by chromatography. First the remaining starting material was eluted with ethyl acetate/heptane (2:1) und finally the desired product was eluted by pure methanol giving 1.98 g 6-(trans-4-amino-cyclohexyloxy)-2-(4-methoxy-benzyl)-7-methyl-2H-isoquinolin-1-one.

d) 6-(trans-4-Amino-cyclohexyloxy)-7-methyl-2H-isoquinolin-1-one hydrochloride 2.64 g (6.7 mmol) of 6-(trans-4-amino-cyclohexyloxy)-2-(4-methoxy-benzyl)-7-methyl-2H-isoquinolin-1-one and 15.3 g (134.5 mmol) of trifluoroacetic acid were heated for 2 h in an microwave oven at 150° C. Then the excess trifluoroacetic acid was distilled off in vacuo and the residue was diluted with 130 ml of 1 M hydrochlorid acid. The aqueous phase was washed with methylene chloride 3 times and then it was freeze dried to give a hydrochloride, which was recrystallized from isopropanol. This furnished 1.1 g 6-(trans-4-amino-cyclohexyloxy)-7-methyl-2H-isoquinolin-1-one (137) as hydrochloride. $R_t$=0.92 min (Method B). Detected mass: 273.22 (M+H$^+$).

6-(cis-4-Amino-cyclohexyloxy)-7-methyl-2H-isoquinolin-1-one (138)

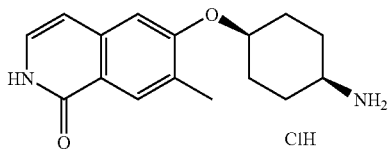

a) cis-4-Aminocyclohexanol hydrochloride

To a solution of 30.0 g (0.265 mol) of cyclohexanone oxime in 300 ml of methylene chloride and 38 ml of ethanol was slowly added at 0° C. 34.5 g (0.318 mol) of tert.-butylhypochlorite. The resulting dark blue solution was cooled to −20° C. and then 31.9 g (0.398 mol) of 1,3-cyclohexadiene were added and the mixture was stored in a freezer at 5° C. for 2 days until the blue color had disappeared. The reaction mixture was concentrated to 50% of its volume and then 600 ml of diethyl ether were slowly added. After stirring overnight the resulting precipitate was isolated by suction to yield 29.0 g of 2-oxa-3-aza-bicyclo[2.2.2]oct-5-ene hydrochloride. 5.0 g (0.045 mol) of this material were hydrogenated with 3.0 g (0.013 mol) platinum oxide at 2 bar hydrogen pressure. After 7 h the catalyst was filtered off and a solution of 20 ml 4 M hydrochloric acid in dioxane was added. After evaporation the residue was recrystallized from 30 ml isopropanol giving 3.1 g of cis-4-aminocyclohexanol hydrochloride.

b) 6-(cis-4-Aminocyclohexyloxy)-7-methyl-2H-isoquinolin-1-one hydrochloride From 2.55 g (16.8 mmol) of cis-4-aminocyclohexanol hydrochloride and 5.0 g (16.8 mmol) of 6-fluoro-2-(4-methoxy-benzyl)-7-methyl-2H-isoquinolin-1-one (137, step b) were prepared 0.98 g of 6-(cis-4-amino-cyclohexyloxy)-7-methyl-2H-isoquinolin-1-one hydrochloride as described in example 137 steps c and d. $R_t$=0.99 min (Method B). Detected mass: 273.18 (M+H$^+$).

6-(cis-4-Ethylamino-cyclohexyloxy)-7-methyl-2H-isoquinolin-1-one (139)

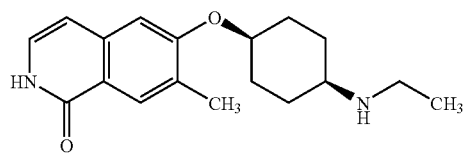 [SMILES: CCN[C@H]1CC[C@@H](Oc2cc3cc[nH]c(=O)c3cc2C)CC1]

0.2 g (0.65 mmol) of 6-(cis-4-amino-cyclohexyloxy)-7-methyl-2H-isoquinolin-1-one hydrochloride (138), 69 mg (0.68 mmol) of triethylamine and 35 mg (0.78 mmol) of acetaldehyde were stirred in 13 ml of dry methanol for 4 h at 5° C. After addition of 37 mg (0.97 mol) of sodium borohydride the mixture was stirred overnight at room temperature. Since incomplete conversion of the starting amine was observed the same amounts of actetaldehyde and sodium borohydride were added again sequentially within 2 h. After further stirring for 2 hours the reaction mixture was acidified with concentrated hydrochloric acid and the methanol was evaporated. The aqueous residue was washed with ethyl acetate and then saturated with potassium carbonate and extracted with methylene chloride to give 145 mg of 6-(cis-4-ethylamino-cyclohexyloxy)-7-methyl-2H-isoquinolin-1-one (139). $R_t$=0.89 min (Method A). Detected mass: 301.20 (M+H$^+$).

6-(cis-4-Isobutylamino-cyclohexyloxy)-7-methyl-2H-isoquinolin-1-one (140)

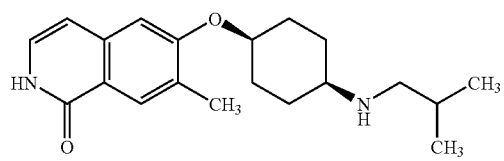 [SMILES: Cc1cc2c(=O)[nH]ccc2cc1O[C@H]1CC[C@@H](NCC(C)C)CC1]

From 0.2 (0.65 mmol) of 6-(cis-4-amino-cyclohexyloxy)-7-methyl-2H-isoquinolin-1-one hydrochloride (138) and isobutyraldehyde were obtained analogous to example 139 151 mg of 6-(4-isobutylamino-cyclohexyloxy)-7-methyl-2H-isoquinolin-1-one. $R_t$=1.10 min (Method A). Detected mass: 329.20 (M+H$^+$).

Analogous to examples 139 and 140 the following compounds were prepared from the respective amines and aldehyde (Table 8).

TABLE 8

| Example | Amine | Aldehyde | Product | [M + H⁺] | $R_f$/ [min] | Method |
|---|---|---|---|---|---|---|
| 141 | 138 | | | 315.22 | 0.96 | A |
| 142 | 138 | | | 397.12/ 399.15 | 1.22 | B |
| 143 | 137 | | | 329.16 | 1.14 | B |
| 144 | 137 | | | 301.15 | 1.00 | B |
| 145 | 137 | | | 397.12/ 399.15 | 1.26 | B |

6-(cis-4-Diethylamino-cyclohexyloxy)-7-methyl-2H-isoquinolin-1-one (146)

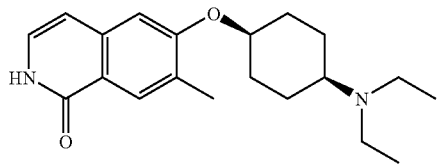 [SMILES: CCN(CC)[C@H]1CC[C@@H](Oc2cc3cc[nH]c(=O)c3cc2C)CC1]

A reaction mixture consisting of 150 mg (0.49 mmol) 6-(cis-4-amino-cyclohexyloxy)-7-methyl-2H-isoquinolin-1-one hydrochloride (example 138), 38 mg (0.63 mmol) of acetic acid, 43 mg (0.97 mmol) of acetaldehyde, molecular sieves and 515 mg (2.4 mmol) of sodium triacetoxy borohydride in 5 ml of methylene chloride was stirred overnight. The reaction mixture was added to 10 ml of 1 M sodium hydroxide solution and extracted twice with a mixture of methylene chloride and isopropanol. After drying and evaporation 122 mg of 6-(cis-4-diethylamino-cyclohexyloxy)-7-methyl-2H-isoquinolin-1-one (146) were obtained. $R_f$=0.99 min (Method B). Detected mass: 329.17 (M+H⁺).

6-(cis-4-Isopropylamino-cyclohexyloxy)-7-methyl-2H-isoquinolin-1-one (147)

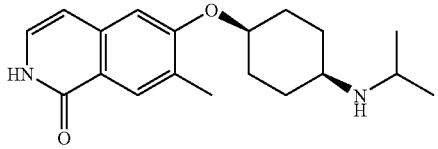

Analogous to example 146 121 mg of 6-(cis-4-isopropylamino-cyclohexyloxy)-7-methyl-2H-isoquinolin-1-one (147) were obtained from 150 mg (0.49 mmol) of 6-(cis-4-amino-cyclohexyloxy)-7-methyl-2H-isoquinolin-1-one hydrochloride (138) by reaction with acetone. $R_f$=1.07 min (Method B). Detected mass: 315.13 (M+H⁺).

2,2,2-Trifluoro-N-(trans-4-hydroxy-cyclohexyl)-acetamide (148)

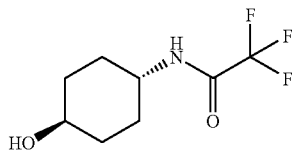

25 g of trans-4-aminocyclohexanol hydrochloride were suspended in 250 mL of dry dioxane and 30 mL of sodium methylate solution (30% in methanol, 1 equivalent) were added. 39.3 mL of ethyl trifluoroacetate were added and the reaction mixture was allowed to stir until the reaction was complete. The reaction mixture was evaporated, taken up in 50 mL of 0.1 N HCl and extracted several times with dichloromethane:isopropanol 3:1. The combined organic layer was extracted once with 0.1 N HCl and brine, dried over sodium sulfate and evaporated to dryness to yield 29.0 g of 148. $R_t$=0.69 min (Method C). Detected mass: 212.2 (M+H$^+$).

2,2,2-Trifluoro-N-(4-hydroxy-cyclohexyl)-N-methyl-acetamide (149)

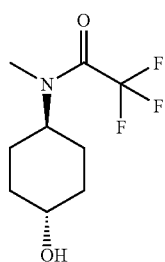

5 g of 2,2,2-trifluoro-N-(4-hydroxy-cyclohexyl)-acetamide (148) were dissolved in 25 mL of dimethyl acetamide, 625 mg of 95% sodium hydride were added and the reaction mixture was cooled to 0° C. 1.64 mL of iodomethane were added slowly and the reaction mixture was allowed to warm to room temperature. Upon completion, the reaction mixture was poured into water, extracted three times with methyl tert. butyl ether and the combined organic layer was extracted once with brine, dried over sodium sulfate and evaporated to dryness. The residue was taken up in water and lyophilized to remove remainders of dimethyl acetamide to yield 4.0 g of product. $R_t$=0.95 min (Method C). Detected mass: 226.2 (M+H$^+$).

trans-4-Methylamino-cyclohexanol (150)

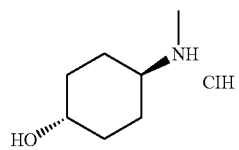

2 g of 2,2,2-trifluoro-N-(4-hydroxy-cyclohexyl)-N-methyl-acetamide (149) were suspended in 10 mL of 1 N HCl and heated in a microwave at 150° until conversion was complete. The resulting solution was lyophilized and the residue was taken up in water and lyophilized again, twice to yield 1.45 g of 4-methylamino-cyclohexanol (150). $R_t$=0.13 min (Method C). Detected mass: 130.3 (M+H$^+$).

2-(trans-4-Methoxy-benzyl)-6-(4-methylamino-cyclohexyloxy)-2H-isoquinolin-1-one (151)

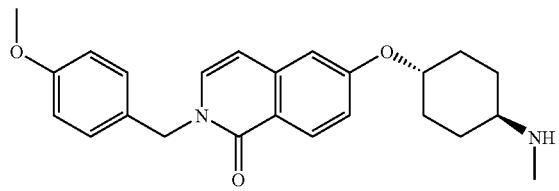 [SMILES: CN[C@H]1CC[C@H](Oc2ccc3c(=O)n(Cc4ccc(OC)cc4)ccc3c2)CC1]

630 mg of sodium hydride (95%) were suspended in 40 mL of dimethyl acetamide. 1.45 g of 4-methylamino-cyclohexanol (150), dissolved in 40 mL of dimethyl acetamide, were added dropwise and 15 min. later 2.48 g of 6-fluoro-2-(4-methoxy-benzyl)-2H-isoquinolin-1-one (177), dissolved in another 40 mL of dimethyl acetamide, were added. The reaction mixture was stirred at 80° C. until the reaction was complete. The mixture was poured into an ice-water mixture, extracted three times with methyl-tert.-butyl ether and the combined organic layer was dried over sodium sulfate and evaporated. Water was added and the crude product was subjected to lyophilization to remove remainders of dimethyl acetamide.

The obtained product is sufficiently pure for further conversion. $R_t$=1.24 min (Method B), detected mass: 393.2 (M+H$^+$).

6-(trans-4-Methylamino-cyclohexyloxy)-2H-isoquinolin-1-one (152)

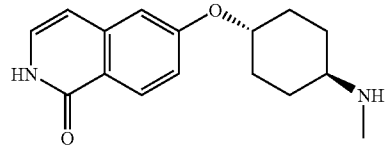 [SMILES: CN[C@H]1CC[C@H](Oc2ccc3c(=O)[nH]ccc3c2)CC1]

2.46 g of 2-(4-methoxy-benzyl)-6-(4-methylamino-cyclohexyloxy)-2H-isoquinolin-1-one (151) were dissolved in 15 mL of TFA and heated in a microwave oven at 150° C. for 2 h. Methanol was added and the reaction mixture was evaporated. The solution was taken up in 1N HCl and extracted three times with dichloromethane. The combined dichloromethane layers were extracted with 1N HCl twice and the combined HCl layers were lyophilized, the residue was taken up in water and lyophilized again to yield 1.31 g of 6-(4-methylamino-cyclohexyloxy)-2H-isoquinolin-1-one (152) as hydrochloride. $R_t$=0.81 min (Method B). Detected mass: 273.2 (M+H$^+$).

The following two products were obtained as hydrochlorides by the same reaction sequence described for the synthesis of 152, using appropriate alkyl halides for the alkylation of 148.

6-(trans-4-Ethylamino-cyclohexyloxy)-2H-isoquinolin-1-one (153)

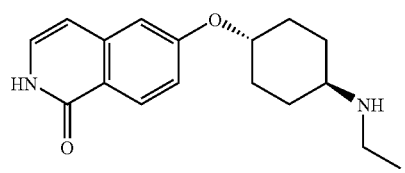 [SMILES: CCN[C@H]1CC[C@H](Oc2ccc3c(=O)[nH]ccc3c2)CC1]

$R_t$=0.85 min (Method B). Detected mass: 287.1 (M+H$^+$).

6-(trans-4-Isopropylamino-cyclohexyloxy)-2H-isoquinolin-1-one (154)

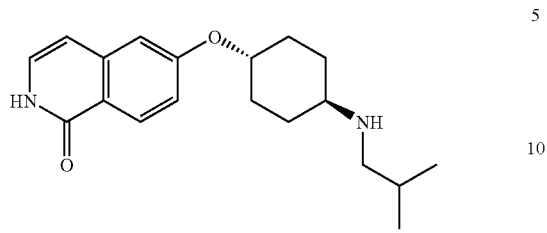

R$_t$=1.16 min (Method B). Detected mass: 315.2 (M+H$^+$).

General Procedure D for the Reductive Amination Reaction:

250 mg of 153 (or of another monosubstituted isoquinolonone-amine) are dissolved in 8 mL of dichloromethane and 6 mL of DMF. 3 eq. of aldehyde, 1.3 eq. of acetic acid, 300 mg of molecular sieves and 3 eq. of sodium triacetoxy borohydride are added. The reaction mixture is stirred for 16 h at 55° C. The mixture is poured into 5 mL of 1 N NaOH and 25 mL of dichloromethane and 10 mL of isopropanol are added. The organic layer is separated and the aqueous layer is extracted three times with isopropanol:dichloromethane 1:3. The combined organic layer is evaporated to dryness and the residue is purified by HPLC and eventually converted into the corresponding HCl salts by addition of 2N HCl and subsequent lyophilization.

The following compounds were prepared according to this procedure and obtained as free base or hydrochlorides (Table 9)

TABLE 9

| Example | Isoquinolinone | Aldehyde | Product | [M + H⁺] | R$_t$/[min] | Method |
|---|---|---|---|---|---|---|
| 155 | 152 | benzaldehyde | N-benzyl-N-methyl cyclohexyl ether isoquinolinone · HCl | 363.2 | 1.14 | A |
| 156 | 152 | propanal | N-propyl-N-methyl cyclohexyl ether isoquinolinone · HCl | 315.2 | 1.02 | D |
| 157 | 152 | isobutyraldehyde | N-isobutyl-N-methyl cyclohexyl ether isoquinolinone · HCl | 329.2 | 1.05 | D |
| 158 | 152 | cyclopropanecarbaldehyde | N-cyclopropylmethyl-N-methyl cyclohexyl ether isoquinolinone | 327.2 | 1.00 | D |
| 159 | 154 | benzaldehyde | N-benzyl-N-isobutyl cyclohexyl ether isoquinolinone | 405.1 | 1.25 | A |

TABLE 9-continued

| Example | Isoquinolinone | Aldehyde | Product | [M + H⁺] | R_t/[min] | Method |
|---|---|---|---|---|---|---|
| 160 | 154 | 4-chlorobenzaldehyde | | 439.3 | 1.51 | A |
| 161 | 154 | pyridine-4-carbaldehyde | | 406.2 | 1.08 | A |
| 162 | 154 | propanal | | 357.2 | 1.10 | B |
| 163 | 154 | isobutyraldehyde | | 371.2 | 1.15 | B |

TABLE 9-continued

| Example | Isoquinolinone | Aldehyde | Product | [M + H⁺] | R_t/[min] | Method |
|---|---|---|---|---|---|---|
| 164 | 154 | (pyridine-3-carbaldehyde) | | 406.3 | 0.94 | A |
| 165 | 154 | (4,4,4-trifluorobutanal) | | 425.2 | 1.26 | B |
| 166 | 152 | (4-chlorobenzaldehyde) | | 397.1 | 1.21 | E |
| 167 | 152 | (pyridine-3-carbaldehyde) | | 364.2 | 0.77 | E |
| 168 | 154 | (cyclopropanecarbaldehyde) | | 369.1 | 1.10 | B |

TABLE 9-continued

| Example | Isoquinolinone | Aldehyde | Product | [M + H]+ | Rt/[min] | Method |
|---------|----------------|----------|---------|----------|----------|--------|
| 169 | 152 | pentanal | | 343.2 | 1.20 | B |
| 170 | 152 | 2-chlorobenzaldehyde | | 397.2 | 1.16 | B |
| 171 | 152 | 4,4,4-trifluorobutanal | | 383.1 | 1.09 | B |
| 172 | 152 | isonicotinaldehyde | | 364.1 | 0.73 | B |
| 173 | 152 | cyclohexanecarbaldehyde | HCl | 369.2 | 1.21 | B |
| 174 | 153 | pentanal | | 357.2 | 1.18 | B |

TABLE 9-continued

| Example | Isoquinolinone | Aldehyde | Product | [M + H]+ | Rt/[min] | Method |
|---|---|---|---|---|---|---|
| 175 | 153 | (aldehyde with CF3) | (product structure) | 397.1 | 1.14 | B |

6-Fluoro-isoquinolinone (176)

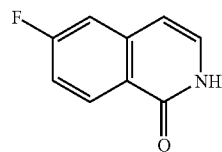 [SMILES: O=c1[nH]ccc2cc(F)ccc12]

4.8 mL (90.3 mmol, 1.5 eq.) of thionyl chloride was added portionwise to a solution of 10 g (60.2 mmol) of 3-fluoro cinnamic acid in 44 ml of chloroform and 1 ml of DMF. The reaction was heated to reflux for 2.5 h. Then the solvents were distilled to yield 11.4 g of the raw acid chloride, which was used without any further purification.

The acid chloride was dissolved in 45 mL of acetone. At 0° C. 8.03 g of $NaN_3$ (123.5 mmol, 2 eq.) were added portionwise. Then 41 mL of water were added while the temperature was kept below 5° C. The reaction was stirred for another 1.5 h. Then 55 ml of chloroform were added. The mixture was extracted with 80 mL of water followed by 40 mL of brine. After drying over $Na_2SO_4$ and filtration 14 mL of diphenyl ether were added and most of the chloroform was removed in vacuo (without heating). A total removal of the chloroform should be avoided.

The solution containing the azide, diphenyl ether and the remaining chloroform was added dropwise at 260° C. within 15 minutes to a solution of 10 mL of tributyl amine in 97 ml of diphenyl ether. A vigorous reaction can be observed during the addition. The reaction was stirred for another 20 minutes at 260° C. After cooling to room temperature 270 mL of n-heptane were added. The precipitated product was filtered off and washed with ether to yield 5.65 g of the title compound. MS (DCI) Detected mass: 164.0 (M+H$^+$).

6-Fluoro-2-(4-methoxy-benzyl)-2H-isoquinolin-1-one (177)

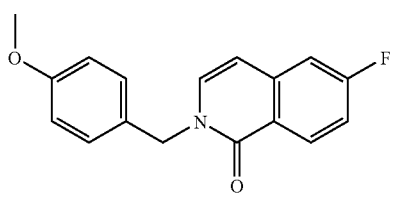 [SMILES: COc1ccc(Cn2ccc3cc(F)ccc3c2=O)cc1]

169 µL of p-methoxybenzylchloride (1.24 mmol, 1.1 eq) were added to a suspension of 200 mg of 6-fluoro-isoquinolinone (176) (1.13 mmol) and 368 mg of $Cs_2CO_3$ (1.36 mmol, 1.2 eq) in 3 mL of DMF. The mixture was stirred for 2 h and then poured on ice. The precipitate was filtered, washed with water and dried to yield 300 mg of the title compound. LCMS Method B, retention time 1.76 min, detected mass 284.14 [M+H]$^+$

4-Ethyl-6,7-difluoro-2H-isoquinolin-1-one (178)

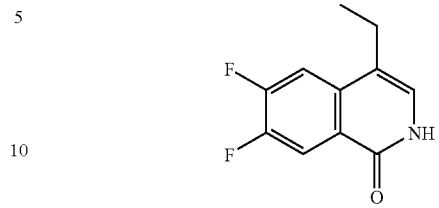

4-Ethyl-6,7-difluoro-2H-isoquinolin-1-one (178) was obtained by the same method described for the synthesis of 176, using (3,4-difluoro-phenyl)-pent-2-enoic acid as a starting material. $R_t$=1.46 min (Method B). Detected mass: 210.1 (M+H$^+$). The used acrylic acid was synthesized from the corresponding aldehyde in similar fashion as described in the literature (see for instance: J. Med. Chem. 2005, 48, 71-90).

6-(trans-4-Amino-cyclohexyloxy)-4-ethyl-7-fluoro-2H-isoquinolin-1-one (179)

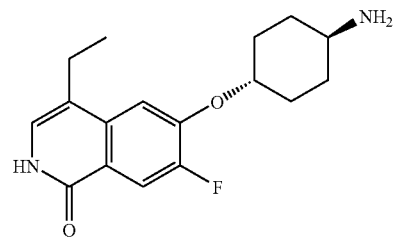 [SMILES: CCc1c[nH]c(=O)c2cc(F)c(O[C@H]3CC[C@H](N)CC3)cc12]

6-(4-Amino-cyclohexyloxy)-4-ethyl-7-fluoro-2H-isoquinolin-1-one (179) was synthesized as hydrochloride by a similar reaction sequence as described for the conversion 137 (steps b, c and d), using 178 as the starting material. $R_t$=0.97 min (Method B). Detected mass: 305.2 (M+H$^+$).

LC/MS-Methods:

Method A:
Stationary phase: Col YMC Jsphere 33×2
Gradient: ACN+0.05% TFA: H$_2$O+0.05% TFA 5:95(0 min) to 95:5(3.4 min) to 95:5(4.4 min)
Flow 1 mL/min Method B:
Stationary phase: Col YMC Jsphere 33×2
Gradient: ACN+0.05% TFA: H$_2$O+0.05% TFA 5:95(0 min) to 95:5(2.5 min) to 95:5(3.0 min)
Flow 1 mL/min Method C:
Stationary phase: Col YMC Jsphere ODS H80 20×2
Gradient: ACN: H$_2$O+0.05% TFA 4:96(0 min) to 95:5(2.0 min) to 95:5(2.4 min)
Flow 1 mL/min Method D:
Stationary phase: Col YMC Jsphere 33×2.1
Gradient: Grad ACN+0.08% FA:H2O+0.1% FA (Formic Acid) 5:95 (0 min) to 95:5 (2.5 min) to 95:5 (3 min)
Flow 1.3 mL/min Determination of Rho Kinase Inhibition To measure Rho-kinase inhibition, $IC_{50}$ values were determined according to the following protocol:

Buffer: 25 mM Tris pH7.5; 0.02% BSA; 5% Glycerol; 0.008% Triton X100; 2% DMSO, 1 mM DTT; 1 mM $MgCl_2$; 0.5 µCi/well $\gamma^{33}P$ ATP Enzyme: ROCKII or ROKα) (Upstate, Catalog #14-451) 0.1 ng/µl Final concentration of ATP in reaction mixture 40 µM Biotinylated substrate, diluted to 0.25 µM with buffer described above (without ATP)

1. 10 µl Tris buffer (±Inhibitor)
2. Add 30 µL of enzyme solution
3. Start the reaction with 30 µL of mix substrate/ATP/ATP33
4. Incubate for 20 min at room temperature
5. Stop reaction with 30 µL of 50 mM EDTA
6. Transfer 50 µL of stopped solution to Streptavidin Flash Plate plus, Perkin Elmer, SMP 103A
7. Incubate for 30 min at RT
8. Wash 4 times with 300 µl of PBS/0.1% Tween 20
9. Radioactivity in the well was determined The following products/compounds were tested in said assay by using the respective form (salt or free base) obtained as in the examples described above and the following activities were measured.

| Compound No. | pIC50 |
|---|---|
| 10 | +++++ |
| 11 | +++++ |
| 12 | +++++ |
| 13 | +++++ |
| 14 | +++++ |
| 20 | +++++ |
| 29 | +++++ |
| 37 | +++++ |
| 41 | +++++ |
| 44 | +++++ |
| 45 | +++++ |
| 46 | +++++ |
| 48 | +++++ |
| 53 | ++++ |
| 56 | +++++ |
| 58 | +++++ |
| 65 | +++++ |
| 66 | ++++ |
| 67 | +++++ |
| 69 | +++++ |
| 70 | +++++ |
| 71 | +++++ |
| 77 | +++++ |
| 125 | +++++ |
| 137 | +++++ |
| 138 | +++++ |

The given activity is denoted as the negative decadal logarithm of the $IC_{50}$ ($pIC_{50}$) as follows:

| | |
|---|---|
| +: | $pIC50 \leq 3.0$ |
| ++: | $3.0 \leq pIC_{50} < 4.0$ |
| +++: | $4.0 \leq pIC_{50} < 5.0$ |
| ++++: | $5.0 \leq pIC_{50} < 6.0$ |
| +++++: | $6.0 \leq pIC_{50}$ |

The invention claimed is:
1. A compound of the formula (I)

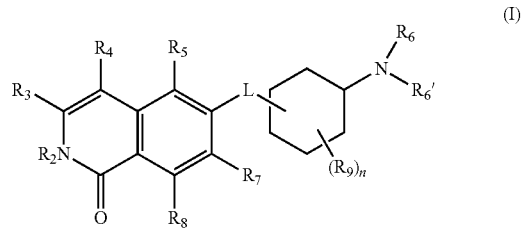

or of the formula (I')

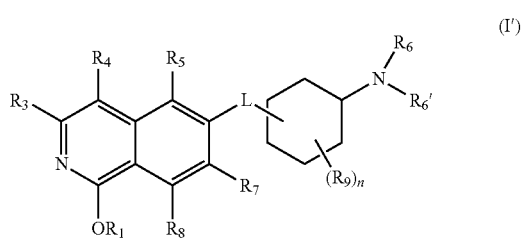

wherein
$R_1$ is H, $(C_1-C_6)$alkyl, $(C_2-C_6)$alkenyl, $(C_2-C_6)$alkynyl, $[(C_1-C_6)$alkylene$]_{0-1}$-$(C_3-C_8)$cycloalkyl, $[(C_1-C_6)$alkylene$]_{0-1}$-$(C_5-C_{10})$heterocyclyl, $[(C_1-C_6)$alkylene$]_{0-1}$-$(C_6-C_{10})$aryl, C(O)—$(C_1-C_6)$alkyl, C(O)$(C_2-C_6)$alkenyl, C(O)—$(C_2-C_6)$alkynyl, C(O)-$[(C_1-C_6)$alkylene$]_{0-1}$-$(C_3-C_8)$cycloalkyl, C(O)-$[(C_1-C_6)$alkylene$]_{0-1}$-$(C_5-C_{10})$heterocyclyl, or C(O)-$[(C_1-C_6)$alkylene$]_{0-1}$-$(C_6-C_{10})$aryl;

$R_2$ is H, $(C_1-C_6)$alkyl, $[(C_1-C_6)$alkylene$]_{0-1}$-R', $[(C_1-C_6)$alkylene$]_{0-1}$-O—$(C_1-C_6)$alkyl, $[(C_1-C_6)$alkylene$]_{0-1}$-O—R', $[(C_1-C_6)$alkylene$]_{0-1}$-$NH_2$, $[(C_1-C_6)$alkylene$]_{0-1}$-NH$(C_1-C_6)$alkyl, $[(C_1-C_6)$alkylene$]_{0-1}$-N$[(C_1-C_6)$alkyl$]_2$, $[(C_1-C_6)$alkylene$]_{0-1}$-CH[R']$_2$, $[(C_1-C_6)$alkylene$]_{0-1}$-C(O)—R', $[(C_1-C_6)$alkylene$]_{0-1}$-C(O)$NH_2$, $[(C_1-C_6)$alkylene$]_{0-1}$-C(O)NH—R', or $[(C_1-C_6)$alkylene$]_{0-1}$-C(O)N[R']$_2$;

$R_3$ is H, halogen, CN, $(C_1-C_6)$alkyl, $(C_1-C_6)$alkylene-R', OH, O—R'', $NH_2$, NHR'', NR''R'', or NH—C(O)—R'';

$R_4$ is H, halogen, OH, CN, $(C_1-C_6)$alkyl, $(C_3-C_8)$cycloalkyl, NH—$(C_6-C_{10})$aryl, or $(C_1-C_6)$alkylene-R';

$R_5$ is H, halogen, CN, $NO_2$, $(C_1-C_6)$alkyl, $(C_2-C_6)$alkenyl, R', $(C_2-C_6)$alkenylene-$(C_6-C_{10})$aryl, $(C_1-C_6)$alkylene-R', $NH_2$, NH—R', NH—$SO_2H$, NH—$SO_2$—$(C_1-C_6)$alkyl, NH—$SO_2$—R', NH—C(O)—$(C_1-C_6)$alkyl, NH—C(O)—R', C(O)N$[(C_1-C_6)$alkyl$]_2$, C(O)OH or C(O)O—$(C_1-C_6)$alkyl;

$R_6$ and $R_6'$ are independently of each other H, R', $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)—R', $(C_1-C_6)$alkylene-C(O)$NH_2$, $(C_1-C_6)$alkylene-C(O)NH—R', or $(C_1-C_6)$alkylene-C(O)N[R']$_2$;

$R_7$ and $R_8$ are independently of each other H, halogen, CN, $NO_2$, $(C_1-C_6)$alkyl, O—$(C_1-C_6)$alkyl, O—$[(C_1-C_6)$alkylene$]_{0-1}$-R', $(C_2-C_6)$alkenyl, R', $(C_2-C_6)$alkenylene-$(C_6-C_{10})$aryl, $(C_1-C_6)$alkylene-R', $NH_2$, NH—R', NH—$SO_2H$, NH—$SO_2$—$(C_1-C_6)$alkyl, NH—$SO_2$—R', $SO_2$—$NH_2$, $SO_2$—NHR', NH—C(O)—$(C_1-C_6)$ alkyl, NH—C(O)—R', C(O)N[($C_1$-$C_6$)alkyl]$_2$, C(O)OH, or C(O)O—($C_1$-$C_6$)alkyl;

$R_9$ is halogen or ($C_1$-$C_6$)alkyl;

R' is ($C_3$-$C_8$)cycloalkyl, ($C_5$-$C_{10}$)heterocyclyl or ($C_6$-$C_{10}$)aryl;

R" is ($C_3$-$C_8$)cycloalkyl, ($C_5$-$C_{10}$)heterocyclyl, ($C_6$-$C_{10}$)aryl, ($C_1$-$C_6$)alkyl, ($C_1$-$C_6$)alkylene-R', ($C_1$-$C_6$)alkylene-O—($C_1$-$C_6$)alkyl, ($C_1$-$C_6$)alkylene-O—R', or ($C_1$-$C_6$)alkylene-$NR_xR_y$;

$R_x$ and $R_y$ are independently of each other ($C_1$-$C_6$)alkyl, ($C_5$-$C_{10}$)heterocyclyl, ($C_6$-$C_{10}$)aryl, ($C_1$-$C_4$)alkylene-($C_5$-$C_{10}$)heterocyclyl, ($C_1$-$C_4$)alkylene-($C_6$-$C_{10}$)aryl, ($C_1$-$C_4$)alkylene-NH($C_1$-$C_6$)alkyl, ($C_1$-$C_4$)alkylene-N[($C_1$-$C_6$)alkyl]$_2$, ($C_1$-$C_4$)alkylene-N[($C_6$-$C_{10}$)aryl]$_2$, or ($C_1$-$C_4$)alkylene-N[($C_5$-$C_{10}$)heterocyclyl]$_2$; and n is 0, 1, 2, 3 or 4; and L is O or O—($C_1$-$C_6$)alkylene;

wherein in residues $R_4$, $R_5$, $R_7$ and $R_8$ one alkyl or alkylene hydrogen atom can optionally be substituted by OH, $OCH_3$, COOH, $COOCH_3$, $NH_2$, $NHCH_3$, $N(CH_3)_2$, $CONH_2$, $CONHCH_3$ or $CON(CH_3)_2$, or an alkyl or alkylene may be halogenated once or more;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

2. The compound according to claim 1 wherein $R_4$ is H, halogen, OH, CN, ($C_1$-$C_6$)alkyl, ($C_3$-$C_8$)cycloalkyl, or ($C_1$-$C_6$)alkylene-R';

$R_5$ is H, halogen, CN, $NO_2$, ($C_1$-$C_6$)alkyl, ($C_2$-$C_6$)alkenyl, R', ($C_1$-$C_6$)alkylene-($C_6$-$C_{10}$)aryl, ($C_2$-$C_6$)alkenylene-($C_6$-$C_{10}$)aryl, ($C_1$-$C_6$)alkylene-($C_5$-$C_{11}$)heterocyclyl, ($C_1$-$C_6$)alkylene-R', $NH_2$, NH—R', NH—$SO_2$H, NH—$SO_2$—($C_1$-$C_6$)alkyl, NH—$SO_2$—R', NH—C(O)—($C_1$-$C_6$)alkyl, NH—C(O)—R', C(O)N[($C_1$-$C_6$)alkyl]$_2$, C(O)OH or C(O)O—($C_1$-$C_6$)alkyl;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

3. The compound according to claim 1 of the formula (I)

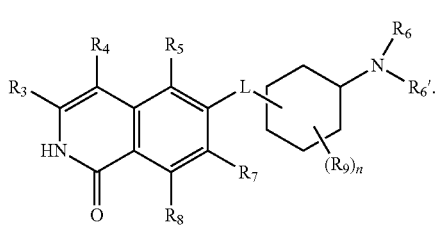

(I)

4. The compound according to claim 1 of the formula (I') wherein $R_1$ is H

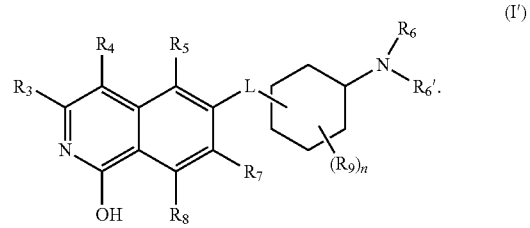

(I')

5. The compound according to claim 1, wherein $R_6$ and $R_6'$ are independently of each other H, ($C_1$-$C_6$)alkyl, R', ($C_1$-$C_4$)alkylene-($C_3$-$C_8$)cycloalkyl, ($C_1$-$C_4$)alkylene-($C_5$-$C_{10}$)heterocyclyl, ($C_1$-$C_4$)alkylene-C(O)—($C_5$-$C_{10}$)heterocyclyl, ($C_1$-$C_4$)alkylene-C(O)—($C_6$-$C_{10}$)aryl or ($C_1$-$C_6$)alkylene-($C_6$-$C_{10}$)aryl.

6. The compound according to claim 1, wherein $R_6$ and $R_6'$ are independently of each other H, ($C_1$-$C_6$)alkyl, ($C_5$-$C_{10}$)heterocyclyl, ($C_3$-$C_9$)cycloalkyl, ($C_1$-$C_4$)alkylene-($C_3$-$C_8$)cycloalkyl, ($C_1$-$C_4$)alkylene-($C_5$-$C_{11}$)heterocyclyl or ($C_1$-$C_6$)alkylene-($C_6$-$C_{10}$)aryl.

7. The compound according to claim 1, wherein $R_6$ is H, ($C_1$-$C_6$)alkyl, ($C_3$-$C_6$)cycloalkyl or ($C_1$-$C_4$)alkylene-($C_3$-$C_6$)cycloalkyl; and $R_6'$ is H, ($C_1$-$C_6$)alkyl, ($C_3$-$C_8$)cycloalkyl, ($C_1$-$C_4$)alkylene-($C_3$-$C_9$)cycloalkyl, ($C_5$-$C_{10}$)heterocyclyl, ($C_1$-$C_4$)alkylene-($C_5$-$C_{10}$)heterocyclyl or ($C_1$-$C_6$)alkylene-($C_6$-$C_{10}$)aryl.

8. The compound according to claim 1, wherein $R_6$ is H, or ($C_1$-$C_6$)alkyl and $R_6'$ is H, ($C_1$-$C_6$)alkyl, ($C_3$-$C_8$)cycloalkyl, ($C_1$-$C_4$)alkylene-($C_3$-$C_8$)cycloalkyl, ($C_5$-$C_{10}$)heterocyclyl, ($C_1$-$C_4$)alkylene-($C_5$-$C_{10}$)heterocyclyl or ($C_1$-$C_6$)alkylene-($C_6$-$C_{10}$)aryl.

9. The compound according to claim 1, $R_6$ is H, or ($C_1$-$C_6$)alkyl; and $R_6'$ is H, ($C_1$-$C_6$)alkyl, ($C_3$-$C_8$)cycloalkyl, ($C_1$-$C_4$)alkylene-($C_3$-$C_8$)cycloalkyl, ($C_1$-$C_4$)alkylene-($C_5$-$C_{10}$)heterocyclyl, which heterocyclyl is unsubstituted or substituted by ($C_1$-$C_4$)alkyl or halogen, or ($C_1$-$C_6$)alkylene-($C_6$-$C_{10}$)aryl, which aryl is unsubstituted or substituted by halogen, ($C_1$-$C_4$)alkyl, O—($C_1$-$C_4$)alkyl or $SO_2$—($C_1$-$C_4$)alkyl.

10. The compound according to claim 1, wherein $R_6$ is H, or ($C_1$-$C_6$)alkyl; and $R_6'$ is H, ($C_1$-$C_6$)alkyl, or ($C_3$-$C_8$)cycloalkyl.

11. The compound according to claim 1, wherein $R_6$ is H; and $R_6'$ is H, ($C_1$-$C_6$)alkyl, or ($C_3$-$C_8$)cycloalkyl.

12. The compound according to claim 1, wherein $R_6$ and $R_6'$ are H.

13. The compound according to claim 1, wherein $R_5$ is H, halogen, CN, ($C_1$-$C_6$)alkyl, R', NH—($C_6$-$C_{10}$)aryl, or ($C_1$-$C_6$)alkylene-R'.

14. The compound according to claim 1, wherein $R_5$ is H, halogen, CN, ($C_1$-$C_6$)alkyl, R', NH—($C_6$-$C_{10}$)aryl, $C_1$-$C_6$) alkylene-($C_6$-$C_{10}$)aryl, or ($C_1$-$C_6$)alkylene-($C_5$-$C_{10}$)heterocyclyl.

15. The compound according to claim 1, wherein $R_5$ is H, halogen, ($C_1$-$C_6$)alkyl, R', NH—($C_6$-$C_{10}$)aryl or ($C_1$-$C_6$)alkylene-R'.

16. The compound according to claim 1, wherein $R_5$ is H, halogen, ($C_1$-$C_6$)alkyl, R', NH—($C_6$-$C_{11}$)aryl, $C_1$-$C_6$)alkylene-($C_6$-$C_{10}$)aryl, or ($C_1$-$C_6$)alkylene-($C_5$-$C_{10}$)heterocyclyl.

17. The compound according to claim 1, wherein $R_5$ is H, halogen, $(C_1-C_6)$alkyl, $(C_6-C_{10})$aryl, $(C_5-C_{10})$heteroaryl, NH—$(C_6-C_{10})$aryl or $(C_1-C_2)$alkylene-$(C_6-C_{10})$aryl.

18. The compound according to claim 1, wherein $R_5$ is H, halogen, $(C_1-C_6)$alkyl, phenyl or $(C_5-C_6)$heteroaryl.

19. The compound according to claim 1, wherein $R_5$ is H, halogen or $(C_1-C_6)$alkyl.

20. The compound according to claim 1, wherein $R_5$ is H or halogen.

21. The compound according to claim 1, wherein $R_5$ is H.

22. The compound according to claim 1, wherein $R_4$ is H, halogen, CN, $(C_1-C_6)$alkyl, NH—$(C_6-C_{10})$aryl, or $(C_1-C_6)$alkylene-R'.

23. The compound according to claim 1, wherein $R_4$ is H, halogen, $(C_1-C_6)$alkyl, or $(C_1-C_6)$alkylene-R'.

24. The compound according to claim 1, wherein $R_4$ is H, halogen, $(C_1-C_6)$alkyl, NH—$(C_6-C_{10})$aryl, or $(C_1-C_6)$alkylene-R'.

25. The compound according to claim 1, wherein $R_4$ is H, halogen, $(C_1-C_6)$alkyl, or $(C_1-C_6)$alkylene-R'.

26. The compound according to claim 1, wherein $R_4$ is H, halogen, $(C_1-C_6)$alkyl, NH—$(C_6-C_{10})$aryl, or $(C_1-C_2)$alkylene-$(C_6-C_{10})$aryl.

27. The compound according to claim 1, wherein $R_4$ is H, halogen, $(C_1-C_6)$alkyl, or $(C_1-C_2)$alkylene-$(C_6-C_{10})$aryl.

28. The compound according to claim 1, wherein $R_4$ is H, halogen, or $(C_1-C_6)$alkyl.

29. The compound according to claim 1, wherein $R_4$ is H or $(C_1-C_6)$alkyl.

30. The compound according to claim 1, wherein $R_4$ is H.

31. The compound according to claim 1, wherein $R_7$ and $R_8$ are independently of each other H, halogen, CN, $(C_1-C_6)$alkyl, O—$(C_1-C_6)$alkyl, $(C_2-C_6)$alkenyl, R', or $(C_1-C_6)$alkylene-$(C_3-C_8)$cycloalkyl.

32. The compound according to claim 1, wherein $R_7$ and $R_8$ are independently of each other H, halogen, CN, $(C_1-C_4)$alkyl, O—$(C_1-C_4)$alkyl, $(C_2-C_4)$alkenyl, phenyl, $(C_5-C_6)$heteroaryl, $(C_3-C_6)$cycloalkyl, or $(C_1-C_4)$alkylene-$(C_3-C_6)$cycloalkyl.

33. The compound according to claim 1, wherein $R_7$ and $R_8$ are independently of each other H, halogen, $(C_1-C_4)$alkyl, O—$(C_1-C_4)$alkyl or $(C_3-C_6)$cycloalkyl.

34. The compound according to claim 1, wherein $R_7$ is H, halogen, $(C_1-C_4)$alkyl, or $(C_3-C_6)$cycloalkyl; and $R_8$ is H.

35. The compound according to claim 1, wherein $R_7$ and $R_8$ are H.

36. The compound according to claim 1, wherein $R_9$ is halogen or $(C_1-C_4)$alkyl.

37. The compound according to claim 1, wherein $R_9$ is Cl, F, methyl or ethyl.

38. The compound according to claim 1, wherein n is 0, 1, 2 or 3.

39. The compound according to claim 1, wherein n is 0 or 1.

40. The compound according to claim 1, wherein n is 0.

41. The compound according to claim 1, wherein $R_3$ is H, halogen, $(C_1-C_6)$alkyl, $(C_1-C_4)$alkylene-R', O—R'' or NHR''.

42. The compound according to claim 1, wherein $R_3$ is H, $(C_1-C_6)$alkyl or NHR''.

43. The compound according to claim 1, wherein $R_3$ is H, $(C_1-C_4)$alkyl, NH—$(C_5-C_6)$heterocyclyl or NH-phenyl.

44. The compound according to claim 1, wherein $R_3$ is H, $(C_1-C_4)$alkyl, NH-phenyl, or NH—$(C_5-C_6)$heteroaryl containing one or more N atoms.

45. The compound according to claim 1, wherein $R_3$ is H.

46. The compound according to claim 1, wherein L is attached as shown in the following figure to the 4-position of the cyclohexyl ring relative to the $NR_6R_6'$ moiety substituted thereon

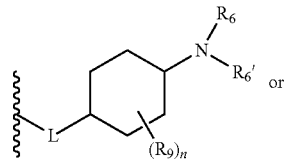

L is attached as shown in the following figure to the 3-position of the cyclohexyl ring relative to the $NR_6R_6'$ moiety substituted thereon

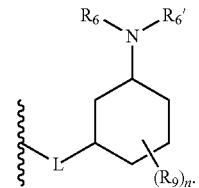

47. The compound according to claim 1, wherein L is attached to the 4-position of the cyclohexyl ring relative to the $NR_6R_6'$ moiety substituted thereon.

48. The compound according to claim 1, wherein L is O-methylene, O-ethylene or O.

49. The compound according to claim 1, wherein L is O-methylene, O-ethylene or O attached to the 4-position of the cyclohexyl ring relative to the $NR_6R_6'$ moiety substituted thereon.

50. The compound according to claim 1, wherein L is O.

51. The compound according to claim 1, wherein $R_3$ is H, halogen, CN, $(C_1-C_6)$alkyl, $(C_1-C_6)$alkylene-R', OH, O—R'', $NH_2$, or NHR'';

$R_4$ is H, halogen, OH, CN, $(C_1-C_6)$alkyl, $(C_3-C_8)$cycloalkyl, or $(C_1-C_6)$alkylene-R';

$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, $NH_2$, NH—R', NH—$SO_2H$, NH—$SO_2$—$(C_1-C_6)$alkyl, NH—$SO_2$—R', NH—C(O)—$(C_1-C_6)$alkyl, NH—C(O)—R', C(O)N[$(C_1-C_6)$alkyl]$_2$, C(O)OH or C(O)O—$(C_1-C_6)$alkyl;

$R_6$ and $R_6'$ are independently of each other H, $(C_3-C_8)$cycloalkyl, $(C_1-C_8)$alkyl, $(C_1-C_6)$alkylene-R', $(C_1-C_6)$alkylene-O—$(C_1-C_6)$alkyl, $(C_1-C_6)$alkylene-O—R', $(C_1-C_6)$alkylene-CH[R']$_2$, $(C_1-C_6)$alkylene-C(O)$NH_2$, $(C_1-C_6)$alkylene-C(O)NH—R', or $(C_1-C_6)$alkylene-C(O)N[R']$_2$;

$R_7$ and $R_8$ are independently of each other H, halogen, CN, $NO_2$, $(C_1-C_6)$alkyl, $(C_2-C_6)$alkenyl, R', $(C_2-C_6)$alkenylene-$(C_6-C_{10})$aryl, $(C_1-C_6)$alkylene-R', $NH_2$, NH—R', NH—$SO_2$—$(C_1-C_6)$alkyl, NH—$SO_2$—R', $SO_2$—$NH_2$, $SO_2$—NHR', NH—C(O)—$(C_1-C_6)$alkyl, NH—C(O)—R', C(O)N[$(C_1-C_6)$alkyl]$_2$, C(O)OH, or C(O)O—$(C_1-C_6)$alkyl;

n is 0, 1, 2; and

L is O or O—$(C_1-C_3)$alkylene;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

52. The compound according to claim 1, wherein $R_3$ is H, halogen, CN, $(C_1-C_6)$alkyl, $(C_1-C_2)$alkylene-R' or NHR'';

$R_4$ is H, halogen, CN, $(C_1-C_6)$alkyl, $(C_3-C_8)$cycloalkyl, $(C_1-C_2)$alkylene-R';

$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, $NH_2$, NH—R', NH—C(O)—$(C_1-C_6)$alkyl, or $C(O)N[(C_1-C_6)alkyl]_2$;

$R_6$ and $R_6'$ are independently of each other H, $(C_3-C_8)$cycloalkyl, $(C_1-C_8)$alkyl, or $(C_1-C_3)$alkylene-R';

$R_7$ and $R_8$ are independently of each other H, halogen, CN, $NO_2$, $(C_1-C_6)$alkyl, $(C_2-C_6)$alkenyl, R', $(C_2-C_3)$alkenylene-$(C_6-C_{10})$aryl, $(C_1-C_3)$alkylene-R', NH—R', NH—$SO_2$—$(C_1-C_6)$alkyl, or $SO_2$—$NH_2$;

n is 0 or 1; and

L is O or O-methylene;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

53. The compound according to claim 1, wherein $R_3$ is H, halogen, CN, $(C_1-C_6)$alkyl, $(C_1-C_2)$alkylene-R' or NHR'';

$R_4$ is H, halogen, CN, $(C_1-C_4)$alkyl, $(C_3-C_6)$cycloalkyl, $(C_1-C_2)$alkylene-R';

$R_5$ is H, halogen, CN, $NO_2$, $(C_1-C_6)$alkyl, $(C_2-C_6)$alkenyl, R', $(C_1-C_6)$alkylene-$(C_6-C_{10})$aryl, $(C_2-C_6)$alkenylene-$(C_6-C_{10})$aryl, $(C_1-C_6)$alkylene-$(C_5-C_{10})$heterocyclyl, or NH—R';

$R_6$ is H, $(C_3-C_6)$cycloalkyl, or $(C_1-C_4)$alkyl;

$R_6'$ is H, $(C_3-C_8)$cycloalkyl, $(C_1-C_8)$alkyl, or $(C_1-C_3)$alkylene-R';

$R_7$ and $R_8$ are independently of each other H, halogen, CN, $NO_2$, $(C_1-C_6)$alkyl, $(C_2-C_6)$alkenyl, R', $(C_2-C_3)$alkenylene-$(C_6-C_{10})$aryl, $(C_1-C_3)$alkylene-R', NH—$SO_2$—$(C_1-C_6)$alkyl, or $SO_2$—$NH_2$;

$R_9$ is halogen or $(C_1-C_4)$alkyl;

n is 0; and

L is O;

or a pharmaceutically acceptable salt thereof, stereoisomeric form thereof or physiologically functional derivative thereof, pharmaceutically acceptable salt of a stereoisomeric form thereof or physiologically functional derivative thereof, or stereoisomeric form of a physiologically functional derivative thereof.

54. A pharmaceutical composition comprising an effective amount of at least one compound of the formula (I) and (I'), or a pharmaceutically acceptable salt thereof, or stereoisomeric form thereof, or pharmaceutically acceptable salt of a stereoisomeric form according to claim 1, and a physiologically tolerated excipient or carrier, or excipient and carrier and, where appropriate, a further additive or other active ingredient, or and additive and other active ingredient.

* * * * *